United States Patent
Bedzyk et al.

(10) Patent No.: US 6,617,148 B2
(45) Date of Patent: Sep. 9, 2003

(54) NATURAL PROMOTERS FOR GENE EXPRESSION AND METABOLIC MONITORING IN BACILLUS SPECIES

(75) Inventors: Laura A. Bedzyk, Odessa, DE (US); Tao Wang, Hockessin, DE (US); Rick Ye, Hockessin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/891,641

(22) Filed: Jun. 26, 2001

(65) Prior Publication Data

US 2002/0155612 A1 Oct. 24, 2002

Related U.S. Application Data

(60) Provisional application No. 60/214,967, filed on Jun. 29, 2000, and provisional application No. 60/268,320, filed on Feb. 13, 2001.

(51) Int. Cl.$^7$ .............. C12N 1/20; C12N 1/00; C12N 15/75; C12N 15/00; C12P 21/06
(52) U.S. Cl. .............. 435/252.31; 435/69.1; 435/243; 435/252.3; 435/320.1; 435/252.5; 435/832; 435/833; 536/23.2
(58) Field of Search .............. 435/68, 172.1, 435/172.3, 252.31, 320.1, 69.4, 252.5, 69.1, 252.3, 485, 243, 832, 833; 536/23.2

(56) References Cited

FOREIGN PATENT DOCUMENTS

| | | |
|---|---|---|
| EP | 0 410 228 A1 | 7/1990 |
| WO | WO 88/02025 A1 | 3/1988 |
| WO | WO 91/00913 A1 | 1/1991 |
| WO | WO 92/14826 A1 | 9/1992 |

OTHER PUBLICATIONS

Stragier, P. et al., Annu. Rev. Genet., vol. 30, pp 297–341, 1996.
Lazazzera, B. A. 2000, Curr. Opin. Microbiol. vol. 3: pp. 177:182, 2000.
Msadek, T. Trends Microbiol. vol. 7:pp, 201–207, 1999.
Nakano et al., Annu. Rev. Microbiol., vol. 52, 165–190, 1998.
Sun et al., J. Bacteriol. vol. 178: pp. 1374–1385.
DeRisi et al., Science, vol. 278: pp. 680–686, 1997.
Shimosaka et al., Appl. Microbiol. Biotechnol. vol. 54(3), pp. 354–360, 2000.
Masson et al., Gene, vol. 140(1), pp. 103–107, 1994.
Seki et al., Adv. ChitinSci., vol. 2, pp. 284–289, 1997.
Kunst et al., Nature, vol. 390(6657), pp. 249–256,1997.
Fawcett et al., The Transcriptional profile of early to middle sporulation in *Bacillus subtilis*, Harvard University, Department of Molecular and Cellular Biology, vol. 97, pp 8063–8068. Jul. 5, 2000.
Ching–Ping Tseng et al., Journal of Bacteriology, vol. 178: 1094–1098, 1996, XP002198735, Effect of Microaerophilic Cell Growth Conditions on Expression of the Aerobic (cyoABCDE and cyd AB) and Anaerobic (narGHJI, frdABCD, and dmsABC) Respiratory Pathway Genes in *Escherichia coli*.
Michiko M. Nakano et al., FEMS Microbiology Letters, vol. 157:1–7, 1997, XP002198736, Adaptation of *Bacillus subtilis* to Oxygen Limitation.
Hugo Crux Ramos et al., The Embo Journal, vol. 14:5984–5994, 1995, XP–001059088, Anaerobic Transcription Activation in *Bacillus subtilis:* Identification of Distinct FNR–Dependent and –Independent Regulatory Mechanisms.
Rowland et al., Sequence and genetic organization of a *Bacillus subtilis* operon encoding 2,3–dihydroxybenzoate biosynthetic enzyme Gene: An International Journal on Gene and Genomes, Elsevier Science Publishers, vol. 178, No. 1, Oct. 31, 1996, pp. 119–123 XP004043349.
Belinda Rowland et al., Duplicate isochorismate synthase genes of *Bacillus subtilis:* Regulation and involvement in the biosynthesis of Menaquinone and 2,3–dihydroxybenzoate, Journal of Bacteriology, vol. 178, No. 3, 1996, pp. 854–861.
Drzewiecki et al., The yvyD gene of *Bacillus subtilis* is under dual control of sigmaB and gibmaH, Journal of Bacteriology, vol. 180, No. 24, Dec. 1998, pp. 6674–6680, XP002206759.

*Primary Examiner*—James Ketter
*Assistant Examiner*—Maria Marvich

(57) ABSTRACT

Genes have been identified in the Bacillus genome that are responsive to various metabolic conditions and growth cycle changes. The new responsiveness of these genes allows for their use in regulated gene expression in Bacillus sp. and for the monitoring of bioreactor health.

7 Claims, No Drawings

SEQUENCE LISTING

<160> NUMBER OF SEQ ID NOS: 81

<210> SEQ ID NO 1
<211> LENGTH: 3687
<212> TYPE: DNA
<213> ORGANISM: Bacillus subtilis

<400> SEQUENCE: 1

```
atgaagaaaa agaaaaggag tccgttgttt aggagattga attatttctc tcctatcgaa      60
caccattcaa ataaacatag ccaaactacc cgcgaggatc gcgattggga gaatgtatac     120
agaaacagat ggcagtacac gaaagtcgtt cgctccaccc acggcgtcaa ctgtacaggg     180
tcttgcagct ggaatattta tgtgaaaaac ggaatagtca cgtgggaagg gcaaaatttg     240
aattatccat caacaggccc ggatatgcct gattttgaac cgagaggctg cccgcggggg     300
gccagttttt catggtatat ctacagcccg ctccgtgtga aatatccata cgtgcgcggt     360
gtgctgatca atttgtggcg ggaggcattg cagacgcatc aaaatccatt ggaagcctgg     420
aaatcgatcg tcgaaaaccc tgaaaaagcg aagtcctata aacaggcgag agggaaaggc     480
ggttttgtgc gcgctgaatg gccggaggtg ctgaagctga tttcagcctc tctgctgtat     540
acagtgatga aatacgggcc tgaccgaaac gtcggttttt ctccgattcc ggccatgtcc     600
atgatcagcc acgcatcagg ctcccggttt atgtcgttaa tcggaggccc tatgctcagt     660
ttttatgact ggtatgcgga tcttcctcca gcatcccgc  aaatttgggg tgaccagacg     720
gacgttccgg aaagcagtga ttggtacaat tccggctata ttatcacatg gggctccaac     780
gttccgttaa cgagaacgcc tgacgcgcat tttttggcgg aggcccgcta taaggcgct     840
```

-continued

```
aaggtcattt cgatcagtcc agattttgcg gaatcctcaa agttcgcgga tgactggctg    900
agtattcgcc aagggactga cggggcgctt gcgatggcga tgggtcacgt tattctgcag    960
gaattttacg tgaaccaaga aactgaacgt tttattgagt acgcgaagca atacactgat   1020
tttccatttc tcgtcactct gtcaaaagaa aatggcgtat acacagcggg acggtttctg   1080
catgcgaagg acatcggcg gaagacaaag catgatcagt ggaagcctgc ggtttgggat    1140
gaacagacaa gttcatttgc cataccccaa gggacaatgg gctcgcgctg ggacgggcag   1200
cagaaatgga acctgcacat gattgatgaa gaaaccgggg aaccgattga accccgtctc   1260
tctgtgctgg aatagagga cgaaatcggc acggtgcgca tcccgtattt ttcaaatgac    1320
ggaaacaaag tgctcgagcg ggatcttcct attaaaaaaa tgaacctgaa cggtgaagaa   1380
acgtacatca cgaccgtgtt tgacttgata ctggctaact acggcgtgaa ccgggcatc    1440
ggcgaacgat cggctgtctc ctatgatgac cctgagccgt ttacgcctgc ctggcaggaa   1500
caaatgacag gaatcaaaaa agaagctgtc gttaagattg ccagagagtt tgcccaaaat   1560
gcgatcgata cagacggccg gtccatgatt atcgtagggg ccggcattaa ccactggttc   1620
aactccgaca cgatctaccg agcagtgtta aatcttgttt tacttgtagg cgcccaaggc   1680
gtaaacggcg gaggctgggc ccattacgtg gggcaggaaa agctccgacc tgctgaaggg   1740
tggcagacga ttgcaactgc aaaggactgg gaaggcgtgc ccaagctgca aaatggcacc   1800
tcatttttct actttgcgac agatcagtgg cgttatgagg accagccgat cagtgatttg   1860
gcatcaccga ttgctgcttc atcccgctac aagcaccacg ctgattacaa tgtgctggcg   1920
gcgcggctag ggtggcttcc gtcttacccg actttcaatc aaaatggcat cgatctgtat   1980
aaagaagctg aaaaagcagg ggcagcaaca cctgaagacg taggtgcgta cgtggcctca   2040
cagctccaag agaaaaaact gaaattcgcg attgaagatc ctgacaatga agtgaatttc   2100
ccaaggaatc tctttgtatg gcgggcaaat ctgatctcaa gctcaggaaa agggcatgaa   2160
tattttctca agcatttgct ggggacaacg aacggtttaa tgaatgacga cagcgacagc   2220
atccgcccag aagaaatcaa atggcgggag caggcgccgg aaggaaagct cgacttatta   2280
atcaatcttg attttcgaat ggcgggtacg gcgctgtatt ccgatatcgt gctgccggcg   2340
gcgacatggt atgaaaaaca cgatctcagc agcacagata tgcatccgtt cattcatcca   2400
tttgctcctg cgatctcggc tccgtgggaa tcgaagtcag actgggatat tttcaaggcg   2460
ctgtcaaaag ccgtttccga tctggcagaa gaagtcgata tggagccggt gaaagaagtg   2520
gttgcgacac cgctgctcca cgacaccatg caggaattgg cccagccatt cggcaaaatc   2580
aatgactgga gcaaaggcga atgtgaagcc attccgggaa aaacgatgcc gaacatccaa   2640
gtcgttgaac gggattacaa acacattttt cataaaatga ctgcacttgg tccgaacgtt   2700
gctttaaagc cgagcggaac aaaagggatg agctggtcaa tagccgatga atatgaatca   2760
ctcaaacaga gactgggaga atcacctcg gacagcgtgg caagggatg tccaaatata   2820
agtgaagcaa agcaggctgc agaagcgatt ttaaccctat catccacttc gaatggaaag   2880
gtcgcagtaa aagcatggga atcacttgaa aacatcacga acctgaagct gaaagacctg   2940
gcggaagaac gcgaggaaga atgctttacg ttcgaacaaa ttacagccca gccgaaaacg   3000
gtgatcacgt ctccagcgtt taccggctct gaaaaaggag ggcgcaggta ttcgccgttt   3060
acaacgaatg ttgaaaaatt aattccgtgg cggacgctga caggcagaca atcctattat   3120
gtcgatcatg aactgatgat ggaattcggt gaaacgatgc cgacattcaa accgatcctc   3180
cagcatcgcc cgtttctgag caaacggcct gatcaagagg gaaaagaaat cgtcctcaat   3240
```

```
tatttgacgc cgcataataa atggtctgtc cacagcatgt attttgattc tctgccgatg      3300
ctgacgctgt tccgcggcgg gccgaccgtg tggatgaata agatgatgc agaggacacg       3360 gatatcaaag acaacgattg gattgaatgc ttcaaccgaa acggcgttgt cgtcgcgaga      3420
gccgttttgt ctcatcggat tcctaaagga atggcgttta tgcaccatgc ccaggaccgc      3480
cacatcaacg tgcccggcac aaagctgacg aataaccgcg gaggcaccca taacagcccg      3540
acaaggattc acgtcaagcc gacacagatg atcggtggct acgcccagct cagctacggc      3600
tttaattatt acgtccaac ggggaatcag cgcgacctga acgtcgtcat ccgcaagctg       3660
aaggaggtcg attggcttga agattaa                                         3687

<210> SEQ ID NO 2
<211> LENGTH: 1464
<212> TYPE: DNA
<213> ORGANISM: Bacillus subtilis

<400> SEQUENCE: 2
ttgaagatta aagcgcaaat cggtatggtc atgaacttgg ataaatgcat cggctgccac        60
acgtgcagcg tcacctgcaa aaacacgtgg acaaaccgtt ccggtgcgga atatatgtac       120
ttcaataatg tagaaacaaa gccgggcatc ggctacccga agcaatggga ggaccaggac       180
aaatataaag gcggctggac attgaaaaaa ggaaagctcg agctgaaatc gggctcgaaa       240
accaatcggc ttgcaggcct tttctataat ccgaatcagc cgtcaattga tgattactat       300
gaaccttgga actatgatta tgaaacatta acgaacagcc gcagaaaaa acaccagccg        360 gtagcacgcc cgaaatcgtc cttgacgggg gatttcatga atatcgaatg gggaccgaac       420
tgggaggacg atctcgcagg cggccacatt acgggacttg aagatcccaa cgtacaaaag       480
atggaggaat cgatcaaaac agaattcgat gacgtctta tgatgtattt gccccgtatt        540
tgcgagcact gcatcaaccc ggcatgcgtc tcatcctgtc catccggcgc catgtacaaa       600
cgcgaggagg acggcattgt gcttgtggat caaaacgcat gccgttcatg gagatattgc       660
gtctcatcct gtccttataa aaagtctat tttaactggc aaacgaacaa agcggaaaaa        720
tgcacactct gctttccgcg tttggaggcg ggactgccaa ccatctgctc tgagacgtgt       780
gttggcagaa tccgctacct cggcgtcatg ctatatgacg cggacaaagt ggaggaagcg       840
gcatctgttg aaaatgaaaa ggatctctac cattcccaat ggacgttttt tcttgatccg       900
aatgatcctg aggttgccaa actggcaaaa gaacaaggca ttccggctga atggatagag       960
gccgcgcagc aatcaccgat ctataaaatg atcattgact ggaagatcgc gctgccgctt      1020
catcctgagt accgcacgct gccaatggtg tggtacattc cgccgctcag cccgattatg      1080
aatctctttg aaggaaaagg cagccggcaa acggcggaag atatttttcc ggctatcgac      1140
caaatgagaa tccgcgataga ttatttggcg cagctgttaa cagccggtga tacggatcat      1200
attcggtcaa cattaaagaa aatgtctgtc atgcgccagt atatgagagc ggtccagacg      1260
aataaatcaa tcgatccgga actgatctcc agtgtcggct taacagaaca gcaaattgaa      1320
gatatgtatc ggctgcttgc gattgccaaa tatgatgacc gctttgtgat tccgagcagc      1380
catcgagaag aagtatcaga tttatacgct gaacaaggaa gctgcggctt atcattttca      1440
ggcggccccg gctcctgttt ctaa                                            1464

<210> SEQ ID NO 3
<211> LENGTH: 555
<212> TYPE: DNA
```

<213> ORGANISM: Bacillus subtilis

<400> SEQUENCE: 3

| | | | | | |
|---|---|---|---|---|---|
| atgaacacca | cagaccggca | aatcacgttc | tctgctcttt | cctgtcttct | ctcttatccg | 60 |
| gatgaagagt | ggagagccga | gcttcccgat | tggaaggctc | ttatccaaga | aatcggcaac | 120 |
| cggcaaatcc | gggagaagct | gctgcacttt | tcgagacgt | cagccagcta | ttctccggaa | 180 |
| gcgctgattg | aacactatgt | ctatacattc | gacttcggga | aaaaaacaaa | tatgtatgtc | 240 |
| acctacttta | actcaggcga | gcaaagggaa | cgcggcattg | aattgctgca | tttaaaaaac | 300 |
| acatacgagc | aatccggttt | cctgccgaca | gagaaagagc | tgcctgatta | tctgccgctg | 360 |
| atgctggaat | tgctgcgggc | tgcagaaatt | gaagcagcga | gaagcgtgtt | tgagaaatat | 420 |
| ctgtccaatg | tgagggagct | ggcatcccgt | ctcgaaaaaa | atgacagtat | atacgctgaa | 480 |
| ctgctgcacg | tgctgctggc | cgcgcttgaa | aacattggcg | tacgtgaaag | cgttgaaggg | 540 |
| gctgttcagg | catga | | | | | 555 |

<210> SEQ ID NO 4
<211> LENGTH: 672
<212> TYPE: DNA
<213> ORGANISM: Bacillus subtilis

<400> SEQUENCE: 4

| | | | | | |
|---|---|---|---|---|---|
| atgagcgggc | agatcctctg | gggtattatg | ccatacattg | tattgacaat | ctttatcggc | 60 |
| ggccatattt | accgctatca | gcatgaccaa | tttggctgga | cggcgaaatc | aagcgagctg | 120 |
| ttagaaaaga | aaaaacttgc | ggctggcagc | acactttttc | actggggact | gctgtgcgtt | 180 |
| gtcggcgggc | atgtcatggg | gattctgatc | ccagaaggcg | tgtatgcttc | ccttggcatt | 240 |
| tcagagcata | tgtatcacaa | aatggcgatt | ggcgctggct | tgccggcggg | cattgcggca | 300 |
| tgtaccggac | ttgtcatcct | gacgtacaga | aggctgtttg | acaaaagaat | ccgcaaaacg | 360 |
| agctcgccat | ccgatatcct | tacgctcctc | ctgctgctgt | tcatgatgct | gtcaggcgtt | 420 |
| gcggccacgt | ttctcaacat | tgattcgaaa | ggatttgatt | accggaccac | agtcgggccc | 480 |
| tggttcaggg | aaatcgtttt | gttcaggcct | gacgcctctt | tgatggagag | tgtcccgcta | 540 |
| tggtttaagt | ttcatattgt | gataggatac | gtcgttttta | tcctgtggcc | gtttacgaga | 600 |
| ttggttcatg | tgttcagtct | gccgctcaag | tatctgaccc | gcagctacgt | tgtatatcgg | 660 |
| aaacgctcgt | ga | | | | | 672 |

<210> SEQ ID NO 5
<211> LENGTH: 834
<212> TYPE: DNA
<213> ORGANISM: Bacillus subtilis

<400> SEQUENCE: 5

| | | | | | |
|---|---|---|---|---|---|
| atgaaaatca | gtatgcaaaa | agcagatttt | tggaaaaaag | cagcgatctc | attacttgtt | 60 |
| ttcaccatgt | tttttaccct | gatgatgagc | gaaacggttt | ttgcggcggg | actgaataaa | 120 |
| gatcaaaagc | gccgggcgga | acagctgaca | agtatctttg | aaaacggcac | aacggagatc | 180 |
| caatatggat | atgtagagcg | attggatgac | gggcgaggct | atacatgcgg | acgggcaggc | 240 |
| tttacaacgg | ctaccgggga | tgcattggaa | gtagtggaag | tatacacaaa | ggcagttccg | 300 |
| aataacaaac | tgaaaagta | tctgcctgaa | ttgcgccgtc | tggccaagga | agaaagcgat | 360 |
| gatacaagca | atctcaaggg | attcgcttct | gcctggaagt | cgcttgcaaa | tgataaggaa | 420 |
| tttcgcgccg | ctcaagacaa | agtaaatgac | catttgtatt | atcagcctgc | catgaaacga | 480 |

```
tcggataatg ccggactaaa aacagcattg gcaagagctg tgatgtacga tacggttatt    540
cagcatggcg atggtgatga ccctgactct ttttatgcct tgattaaacg tacgaacaaa    600
aaagcgggcg gatcacctaa agacggaata gacgagaaga agtggttgaa taaattcttg    660
gacgtacgct atgacgatct gatgaatccg gccaatcatg acacccgtga cgaatggaga    720
gaatcagttg cccgtgtgga cgtgcttcgc tctatcgcca aggagaacaa ctataatcta    780
aacggaccga ttcatgttcg ttcaaacgag tacggtaatt ttgtaatcaa ataa          834
```

<210> SEQ ID NO 6
<211> LENGTH: 753
<212> TYPE: DNA
<213> ORGANISM: Bacillus subtilis

<400> SEQUENCE: 6

```
atggcgaaac cactatcaaa agggggaatt ttggtgaaaa aagtattgat tgcaggtgca     60
gtaggaacag cagttctttt cggaacccct tcatcaggta taccaggttt acccgcggca    120
gacgctcaag tcgcaaaagc agcatccgag ctgcctaacg gaatcggcgg ccgtgtctac    180
ctgaacagta cgggcgccgt ttttacagct aaaatcgtgc ttcctgaaac tgtcaaaaac    240
aacgactcgg tctctactcc ctatatttat tctggcttta gggcaacaag cggaactgaa    300
gccgatatcg ggcttcagta cagcaaacaa tacaacgtct ggaagcccct catgaaggtt    360
gggtccaaaa atgaagaaac gtacatcgaa ggaaaagaca aattcacata caataaaggc    420
ttccgccctg gaagcacagt ccaaatgaca atctataaaa atttaagcgg caatacgcgc    480
atgacccttt ggggaacgaa caatgacggc tacaccggac ggattatcac agaaattcaa    540
ggaaccaaca tcggcacgat ttcaaaatgg aaaacacttg ctaccgcggc tgtttcgtat    600
gaaagccagc gtgatgcgat caaagcaacc ttttcgacct cttttaacaa catcactatc    660
gacaataaag ccgtcactcc tgtggtagat acacaggatt tcgcaaaggt ttcagttgca    720
ggaaataacg ttacgatctc tgttaataaa taa                                 753
```

<210> SEQ ID NO 7
<211> LENGTH: 570
<212> TYPE: DNA
<213> ORGANISM: Bacillus subtilis

<400> SEQUENCE: 7

```
atgaactata acatcagagg agaaaatatt gaagtgacac ccgcgttaaa ggatcatgtc     60
gagaggaaga tcggcaagct ggagcgctat tttgaccata gcgtggatgc tgatgtgaac    120
gtcaacttga agttttacaa tgacaaggag tctaaggttg aggttacgat tccgatgaca    180
gatctggcgc ttcggtccga ggtgcataac gaggatatgt acaacgcaat tgatctcgca    240
acaaacaaac tggaacgtca aatccgtaag cataaaacga agtaaaccg taaattccgt    300 gagcagggct ctccaaaata tttattggca acggtcttg gctctgatac agatattgcg    360
gttcaggatg acatagaaga ggaggagagc ttggacatct ccgtcagaa acgctttaat    420 ttaaagccga tggatagtga agaagcgatc ttgcaaatga atatgctcgg ccataatttc    480
tttgttttca caaatgcgga aacaaacctt acaaatgtcg tgtaccgcag aaatgacggg    540
aaatatggct taattgaacc gactgaataa                                     570
```

<210> SEQ ID NO 8
<211> LENGTH: 477
<212> TYPE: DNA

<213> ORGANISM: Bacillus subtilis

<400> SEQUENCE: 8

| atgactatat gtttcctatt attttcttct tattactttta gcaatatttc acctcagaat | 60 |
| ccactgttca aaaaaatttt tttgcaacaa ttgtctcccc aaggctttgg cttttatagt | 120 |
| aaaagccta cagaagaaaa catttcattt cacacaaaag aaaatttaaa gttacctaat | 180 |
| gcacttccca ataatttttt tgggataaaa agagaaggaa gagttcaggc aatagaatta | 240 |
| ggcaaaattg tagagaatat cgatccaaag aattggaaaa cttgtgaaaa caacaactcc | 300 |
| tgcacaaatt tagagaaaca aataaagcct attaaggtta taaaaatga agattatata | 360 |
| catcttagca aaggagaata cctaatatat cgccaaaaac cactctcatg gtattggata | 420 |
| gactttaagc aaactaccctc ttttgaaaga aaggtgctaa aaataaaaat agtatga | 477 |

<210> SEQ ID NO 9
<211> LENGTH: 972
<212> TYPE: DNA
<213> ORGANISM: Bacillus subtilis

<400> SEQUENCE: 9

| atgaagatat taaatagttt agaaggttat attgacacct ataatccatg gaaaaataca | 60 |
| tatgcacttt ttagaagttt acttggtttc tcaacattac tagtactatt attcaatagt | 120 |
| actgatattt tatttagtta tagtgcaaat aatgtcacat gtgaaaatgt ctatatccct | 180 |
| accgctttt gttttgctaa agaatatagt atcaattttg agattataag atacttaatg | 240 |
| atttttatat taaccttagt ggttataggg tggagaccta gatttaccgg tttatttcac | 300 |
| tggtatattt gctatagtat tcaaacttca gctttaacta tcgatggtgg agagcaaatt | 360 |
| gcaactgttc tttcttttct tatattacct gttacattat tagattcaag gcgaaatcat | 420 |
| tggaatataa agaaaacaa taatgaatct ttcacaaaga agacagtatt gttttatata | 480 |
| atgacaataa ttaaaattca gttttttatc atttatttaa acgcagcttt agagcgattg | 540 |
| aaaaataaag agtgggcaga aggaacagca atttactatt tcttttctga tccggtgttt | 600 |
| ggattacctg aatatcaact taacttaatg aatccactac ttgaaagcaa tttatttgtt | 660 |
| gtcatcactt ggttagtaac tatttttgag ttgttcttag cagcaagcat aatttcaaat | 720 |
| atcagaataa agagaattgc ccttgttttg ggaatattat ttcatattgg gataatattc | 780 |
| agcattggta ttgtaagttt tggcttgatc atgatatcag cattaattat atatctgcat | 840 |
| cctgtacaac aaaatatcac tatgaattgg tgttctcctt tatttaaata tatatatgta | 900 |
| aaaggaaaga gaaatttcaa agaataggga ggtgaatcag tcaagtttct tacaaaattg | 960 |
| tttcatagct aa | 972 |

<210> SEQ ID NO 10
<211> LENGTH: 612
<212> TYPE: DNA
<213> ORGANISM: Bacillus subtilis

<400> SEQUENCE: 10

| ttgaaaagta aattacttag gctattgatt gtttccatgg taacgatatt ggttttttca | 60 |
| ttagtaggac tctctaagga gtcaagtaca tctgctaaag aaaaccatac attttctgga | 120 |
| gaagattact ttagaggact tttatttgga caagggaag ttggtaaatt aatttcaaac | 180 |
| gatttggacc ctaaactcgt aaaagaggca atagtacga aggtaaaaa gttagtaaat | 240 |
| gatgtagtca aatttataaa aaaagatcaa ccacaatata tggatgaatt gaaacaatcg | 300 |

-continued

| | |
|---|---|
| attgacagca aagaccctaa aaaactcatt gaaaatatga ccaaagcaga ccaacttatc | 360 |
| caaaaatatg ctaagaaaaa tgaaaacgta aaatactctt ctaataaagt tactccatct | 420 |
| tgtgggcttt atgccgtctg tgtagcagct ggatatttat atgttgtggg cgttaacgca | 480 |
| gttgcattac aaacggctgc cgcagtaaca actgcagtgt ggaaatacgt tgccaaatat | 540 |
| tcctcttcag cttctaataa ttctgattta gaagcggctg ctgcaaaaac cctaaaattg | 600 |
| attcatcaat aa | 612 |

<210> SEQ ID NO 11
<211> LENGTH: 1041
<212> TYPE: DNA
<213> ORGANISM: Bacillus subtilis

<400> SEQUENCE: 11

| | |
|---|---|
| atgaaggcag caagatggca taaccaaaag gatatccgta ttgaacatat cgaagagcca | 60 |
| aaaacggagc cgggaaaagt aaagatcaaa gtcaaatggt gcggcatctg cggaagtgat | 120 |
| ttacacgaat atctgggcgg cccgatcttt attccggttg acaaaccgca cccattaaca | 180 |
| aatgaaacgg cacctgtcac aatggggcat gaattctccg gtgaagttgt cgaagtcgga | 240 |
| gaaggcgttg aaaattataa agttggagac gcgttgtag tcgagccgat ttttgctaca | 300 |
| cacggccacc aaggcgccta caaccttgat gaacaaatgg gattcctcgg cttagccggc | 360 |
| ggaggcggcg gtttctctga atacgtctct gtggatgaag cttttgttt caaacttcct | 420 |
| gatgaattat catatgaaca aggcgcgctc gttgaaccttt ctgcagttgc tctatacgct | 480 |
| gtccgctcaa gcaaactcaa gcaggcgac aaagcggctg tattcggctg cggcccgatc | 540 |
| ggacttcttg tcattgaagc gctgaaggct gccggtgcaa ctgatattta cgctgttgag | 600 |
| ctttctcctg aacgccagca aaagctgag gagcttggcg cgatcatcgt tgatccgtct | 660 |
| aaaacagacg atgtagtcgc tgagattgca gaacgtacag gaggcggtgt tgacgtagca | 720 |
| ttcgaagtca ctggtgtccc agtggtgtta cgacaagcca tccagtccac tacaattgcc | 780 |
| ggtgaaaccg tcatcgtcag catttgggaa aaaggtgctg aaatccatcc gaacgatatc | 840 |
| gtaatcaaag aacgtacagt aaaaggaatt atcggatacc gcgacatctt cccggctgta | 900 |
| ttgtcattaa tgaaagaagg ctatttctca gccgacaaac tcgtaacgaa aaaaatcgta | 960 |
| ctagatgatt tgatcgagga aggcttcggg gctcttatta aagagaaaag ccaagtcaaa | 1020 |
| atccttgtta gacctaacta a | 1041 |

<210> SEQ ID NO 12
<211> LENGTH: 171
<212> TYPE: DNA
<213> ORGANISM: Bacillus subtilis

<400> SEQUENCE: 12

| | |
|---|---|
| atggaaaagc tatttaaaga agttaaacta gaggaactcg aaaaccaaaa aggtagtgga | 60 |
| ttaggaaaag ctcagtgtgc tgcgttgtgg ctacaatgtg ctagtggcgg tacaattggt | 120 |
| tgtggtggcg gagctgttgc ttgtcaaaac tatcgtcaat tctgcagata a | 171 |

<210> SEQ ID NO 13
<211> LENGTH: 414
<212> TYPE: DNA
<213> ORGANISM: Bacillus subtilis

<400> SEQUENCE: 13

```
atgaaaaagt ggattgtttt atttcttgtt ttaatagcag cagccattag tatttcgtt      60 tatgtttcta caggtagcga aaacctttt tataatgata taaatttaac tcaatatcaa     120
aaagaagtag actctaaaaa acctaaattt atttatgttt atgagacaag ttgtcctcct    180
tgtcaagaaa taaaacctga gttaaatgaa gtaattaaaa agaaaagtt aaaagtacag     240 gctttaaata ttgaagaaaa ggaaaattat aacactgaat ttttagataa atataatttg    300
aataaaactc caacgattct ctattacaaa gatggcaaag aaaaagatcg gttagagggc    360
tatagaagtg caagccaaat agaaaagttc tttgataaaa atggtgatag ataa           414
```

<210> SEQ ID NO 14
<211> LENGTH: 1269
<212> TYPE: DNA
<213> ORGANISM: Bacillus subtilis

<400> SEQUENCE: 14

```
atgaaactga gtgatatttta tttggaatta aagaaaggct atgccgattc tttattgtat    60
tcagatttgt cattgttggt taatataatg gaatatgaaa aagatattga tgtgatgtca    120
attcaatctt tggttgcagg ttatgaaaaa tcagatactc ctacaataac atgcggtatt    180
atagtttata cgaaagcaa agaattaaa agtgttttaa atagtgttaa agatgatttt      240
aacgagatta ttgttctaga ttcatactcc actgatgata ccgttgatat tattaaatgt    300
gattttcctg atgttgaaat taaatatgaa agtggaaga atgattttc ctatgctaga      360 aataaaatta tagagtatgc tacttccgaa tggatttatt ttattgatgc agataattta    420
tactctaaag aaaacaaagg gaaaatagc aaagtagcta gagttttaga gtttttttct     480
attgattgtg tagttagtcc atatataga gaatatactg gacatctata ttctgataca    540
cgaagaatgt tcggctcaa tggtaaagtt aaatttcatg ggaaagtgca tgaagaacct    600
atgaattata atcatagtct accttttaat ttcattgtga accttaaggt ttaccataat   660
ggatataatc cttcagagaa taatataaaa tcaaaacac gaaggaatat aaatctcaca    720
gaagaaatgt taagattgga gccccgaaaac ccaaaatggt tattctttttt cggcagagaa  780 ctacatttac ttgataaaga tgaagaagca attgattatc tgaaaaaatc aataaacaac   840
tataaaaaat ttaatgatca aagacatttt atagatgctt tagtgctatt atgtactttta    900 ttattgcaga gaataattaa tgttgactta actttatatt tggatataatt ggaaactgaa    960 tatccaagat gtgttgatgt tgattacttttt agatctgcaa ttttgttagt agatatgcaa   1020
aataaactta cttcttttaag caatatgatt gatgaagctc ttacagacga gagatacagt   1080 gctataata caacaaaaga tcactttaaa agaattttaa taagccttaa tattcaactc     1140
gaaaattggg aaagagtaaa agaaatatca ggggaaatta aaatgataa tatgaaaaaa    1200 gaaattaaac aatatcttgc caactcactc cacaatattg aacacgtcct gaaaggaatt   1260
gaagtatga                                                            1269
```

<210> SEQ ID NO 15
<211> LENGTH: 447
<212> TYPE: DNA
<213> ORGANISM: Bacillus subtilis

<400> SEQUENCE: 15

```
atgaatacaa gatatgtaaa atcattttt ttattactgt ttttctctc tttctttggc      60 acaatggcta gtttattcta cagtgagatc atgcatttca aaccatgtgt ctatgttgg    120 tatcaaagaa tatttctata tcctataccct attatcttac taataggctt attaaaaaaa  180
```

```
gatcttaatt cgatatttta tgttgttttc ctttcatcaa ttggattgat tattgcgttt    240
tatcattata ttatccaact tacacaaagc aaaagtgtcg tatgtgaaat tggaaccaac    300
agctgcgcaa aaattgaagt agagtatcta ggctttatta cattaccctt aatgagttca    360
gtatgttttg cattgatatt tggtatagga ctgaaattaa ttatcaaaag caagaaatta    420
aaacaaaatc aacatgtata taattga                                       447
```

<210> SEQ ID NO 16
<211> LENGTH: 954
<212> TYPE: DNA
<213> ORGANISM: Bacillus subtilis

<400> SEQUENCE: 16

```
atgaaaaga tatctcttac cttattaatc ttacttctcg cgctgacggc ggcagcttgc      60
ggcagcaaaa atgaatcaac tgccagcaag gcaagcggca cagcatctga aagaagaaa    120 attgaatacc ttgataaaac atatgaagta actgtaccga cagacaaaat tgccattacg    180
ggaagcgttg aatcaatgga agacgcgaaa ttgcttgacg ttcatccgca aggcgcaatt    240
tcattctccg gcaaattccc tgatatgttc aaagacatca ctgataaagc cgaaccaacc    300
ggagaaaaaa tggagccaaa tattgaaaag attcttgaaa tgaagccaga tgttatcctt    360
gcttcaacaa gtttccgga aaaacgctg caaaaaatca gcacagcagg cacgacgatc      420
ccagtttctc atatctcttc aaactggaag gaaaacatga tgcttcttgc ccagctgact    480
ggaaaagaga aaaagcaaa gaaattatt gcagactatg aacaggatct aaaagaaata      540
aaaacaaaaa tcaacgataa agcgaaagat tcaaaagcgc ttgtcatcag aatcagacaa    600
ggcaacattt acatttaccc tgaacaggtg tatttcaact ccacactata cggtgattta    660
ggccttaagg cgccgaacga agtaaaggct gcaaaagcgc aagagctgag ttcattagaa    720
aaattaagtg aaatgaaccc ggaccatatt ttcgtccaat tttctgatga tgaaaatgca    780
gacaaacctg atgccttaaa agatttagag aaaatccaa tctggaaaag ccttaaagca     840
gtcaaagaag accatgtgta tgtcaactca gtggaccctc tcgcacaagg cggcacagct    900
tggagcaaag tccgtttcct gaaagcggct gctgaaaaat gacacaaaa ctaa           954
```

<210> SEQ ID NO 17
<211> LENGTH: 1005
<212> TYPE: DNA
<213> ORGANISM: Bacillus subtilis

<400> SEQUENCE: 17

```
atgtattcaa aacagtggac acgtatcata ttgattactt ctccatttgc tatagcgctg     60
tcacttttgc tttcaatcct ttatggggca aagcatctca gcacagatat tgtttttaca    120
tctcttattc atttcgatcc gggaaacaca gaccatcaaa ttatatggca ttcccggatt    180
ccaagggctg ccggcgctct gctcataggg gcagcccttg ctgtttctgg agcgcttatg    240
cagggcatta cgcgcaatta tttagcttcg ccatccatta gggtgtttc agatggttca    300 gcgtttatca ttacgctttg catggttctg ctcccgcaat catcttcgat gaaatgatg    360 atatactctt ttatcggctc agcgttagga gcggtgttag tattcggcct tgccgccatg    420
atgccaaacg gatttacccc cgtgcagctc gccatcatcg gcacagtcac aagcatgctg    480
ctcagcagct tatcagcggc catgtcgatt tattttcaaa tttctcagga tctcagtttc    540
tggtacagtg ccagacttca tcaaatgagt ccagatttcc tgaagcttgc cgctccgttt    600
```

| | |
|---|---|
| ttcctgattg gcattataat ggccatttct ctcagcaaaa aggtaaccgc tgtatcatta | 660 |
| ggggacgaca tttctaaaag cctggggcaa agaaaaaaa ccattaaaat catggcgatg | 720 |
| ctttccgtca tcattctaac cggcagtgcc gtagcgctgg ccgaaaaaat tgcgtttgtc | 780 |
| gggttggttg ttccgcatat cacgagattt ctcgtcggct ctgattacag caggctgatt | 840 |
| ccgtgttcct gtattttggg cggaatcttt ttaaccctgt gtgatctcgc aagcagattt | 900 |
| atcaactatc cgtttgaaac accgattgag gtcgtaacat ccattatcgg cgtacctttc | 960 |
| ttcctttatt taattaaacg aaaggaggg gagcaaaatg ctaa | 1005 |

<210> SEQ ID NO 18
<211> LENGTH: 1185
<212> TYPE: DNA
<213> ORGANISM: Bacillus subtilis

<400> SEQUENCE: 18

| | |
|---|---|
| atggctaaaa aatatgcatt gttcatcgct ttgattcttg ttgtcagcta tttcagctta | 60 |
| acgagcggat cattttctgt tcgtcctgct gagctgctct ccactctttt tcaaatcgac | 120 |
| ccgaatccgc agtatgaaat tttgctgttc gatttaagac tgccgcgggt tgtcatggct | 180 |
| gctattattg gactcggtct tggcattgca ggcgctgtta ccaggccat cacgagaaac | 240 |
| gggcttgctg accctggaat tctcggaatc aacgcagggg caggagctgg cattgtagcg | 300 |
| tttatgctct tattccaagg ccagaaggaa gtgacatcca tagctgcagc gatgggaatg | 360 |
| ccgctctttg gattgatagg cggctcatc gcggcgatcc tgatttacat atttgcatgg | 420 |
| cacagaggca atttagattc aggaagaatt attttggtag ggattgcgat caattcagga | 480 |
| ttcagcgccc tgtctttgtt tttatctta aaaatggacc cgcaagacta tcaaatggcc | 540 |
| atggtgtgga aaacggaag catctggtct gccaactgga cgtatattac agctgtactc | 600 |
| ccatggatgc tgctgtttat accgattctt atcggcaaat cccgcctgct cgacaccatt | 660 |
| cgttttgatg aagacacagt cagaagcctc ggtatttcat caaataaaga aaaaaccatc | 720 |
| cttctcgttg cctgtgtagc aatcatcagc gcctgtgtct ccgtagcggg aagtatggcg | 780 |
| tttgtcggct taattgctcc ccatatctca cggagactgg ctggcgtcga acatcgctat | 840 |
| atcctgccac tgagcggttt aatcgggatg cttcttgtga taagcgcaga cttgccggaa | 900 |
| aaactgtttt tcagcccgc agaagtgccc gcagcatcat tttggcgatc ctcggagttc | 960 |
| cttatttctt tatctgctt ttcaagcaaa aaaggggga gaatgcttga aggatctct | 1020 |
| ttcagaacac aaagccggca acaggaggtt cacgctgtac ctccctcctt cctacagcac | 1080 |
| agacagcggg ggatttcctg ctgtttacgt gcaggatggc agttctttgt tccaaaacca | 1140 |
| aatcgaatta ctagaaagcg cctttcaaca gcaaaggctc cctga | 1185 |

<210> SEQ ID NO 19
<211> LENGTH: 477
<212> TYPE: DNA
<213> ORGANISM: Bacillus subtilis

<400> SEQUENCE: 19

| | |
|---|---|
| atggctaaag ccttgattac atatgccagc atgtcaggaa atacagaaga cattgccttc | 60 |
| ataataaaag atacgcttca ggaatatgag ttggatatcg attgtgtcga gataaatgat | 120 |
| atggatgcgt cttgttttaac ctcctatgat tatgtactga ttggcaccta tacatggggg | 180 |
| gacggcgatt tgccctacga agcggaggat tttttcgaag aggtcaaaca gattcagctt | 240 |
| aatggtttaa aaacagcctg cttcgggtct ggcgattatt cttatccaaa gttttgcgaa | 300 |

```
gcggtgaatt tgttcaatgt catgctgcaa gaggcgggag ctgctgttta ccaggaaaca    360
ctaaaaattg aattagcgcc tgaaacagat gaagatgtgg aaagctgccg agcgtttgcg    420
agaggttttc ttgcatgggc agattatatg aacaaggaaa aaatccatgt ttcataa      477

<210> SEQ ID NO 20
<211> LENGTH: 894
<212> TYPE: DNA
<213> ORGANISM: Bacillus subtilis

<400> SEQUENCE: 20
atgtttcata aagggcaacc cgctgttacg gcatcggcgt tttctggata ttttgtggcg     60
gtacaaagag aaggcatttt tcattactct ttggagcagg gctggagaaa gcttttttcgt   120 ttgaaaagta agatacactg tatcagctac atagggcctt acttatttgg cgttggtgaa   180
aagggaacag tcattcgttc ggctgatgaa gggaaaacct ggacgatgtc gagctttccg   240
acaaatgcaa cagtgtgggc gattaccggc agaaacaacg ggtttgtctg cgcccacggt   300
aagcattgta tttatgtatc ggatgatttt ggtgtctcat ggcgcgtagc caaaccttt    360 gccgaatttc ataatccccc tgttatccgg tcgttatgcc ttcacgggg caatctcttt    420 atcggcacgc aaatacacga atattttggc ggcatttggg cttacgacat taagcgtgac   480
actgtccaag ttgtcaaaaa agaaaaaaac cggatgacgg catccatgct cgtgttcaat   540
gaaaattggc tggtggcggc gatgggttct gtgaaaggaa agcacggtgc tgtcactgta   600
aggaatcttt tgaatggtga agaattcacc atacaatcca gtatgatcag aaatgaagaa   660
tcatttcttg atctttcaga ggatgatggc attatatatg tcactacaac acaagatgaa   720
aatggttttt cgagaattta ccaggttgat ctcgaagccc ggtcgttaaa atggttcgat   780
accattaagg gacatggatg gagagtggcc aatcagaaag agaatttctt ttgcgcaggc   840
ttgtatgaat gtaaatttgt ccagccgtac gaagtttcag caatgattca ttag        894

<210> SEQ ID NO 21
<211> LENGTH: 537
<212> TYPE: DNA
<213> ORGANISM: Bacillus subtilis

<400> SEQUENCE: 21
ttggcgaaga ttttgctcgt ttatgcaaca atgtcaggca acactgaagc tatggcagat     60
ttgattgaaa agggcttca ggaggcgtta gcagaagtag accgtttcga agcaatggat    120
attgatgatg cccagctgtt taccgattat gaccatgtca taatgggaac ctacacgtgg   180
ggagacggag atctgcctga tgaatttta gatcttgttg aagacatgga ggagattgat   240
ttttccggca aaacatgcgc tgtattcggt tccggtgata cagcatatga attttttctgc  300 ggagcggttg atacgctaga ggcaaaaata aagaacgcg gtggagacat tgtgctgcct   360
tcggtaaaaa tcgaaaataa tccagaaggt gaagaagagg aagaattaat aaacttcggg   420
agacaattcg caaagaaaaa gcgggtgcgc tgtctgatca ctcactggga actgctaaaa   480
cggctgttcc tttttttctt gtctttgtat ctttcctttg atacagtaat gaggtag     537

<210> SEQ ID NO 22
<211> LENGTH: 786
<212> TYPE: DNA
<213> ORGANISM: Bacillus subtilis

<400> SEQUENCE: 22
```

```
atgaatgcaa agggtataga gggaaaaatt gcttttataa caggggctgc ccaaggaata      60
ggcgaagctg ttgcgcggac gcttgccagt caaggcgcac atattgcggc agttgattat     120
aatcctgaaa agctggaaaa ggttgtgagc agcctcaaag cagaagcccg ccatgcagaa     180
gcttttcctg cggatgtgag agacagcgcg gcgattgacg agatcacggc gcgcatcgaa     240
cgtgaaatgg ggccgattga tattttagtg aatgtagcgg gtgtccttcg cccgggactg     300
atccattcgc ttagcgatga ggaatgggag gcgacgttct cagtgaattc gactggcgta     360
tttaacgcct cgcgttcagt cagcaaatat atgatggacc gagatcgggt tcgattgta     420 acagtcggat cgaatcctgc cggtgtacca agaacatcta tggcggcata tgcgtcttca     480
aaggctgcgg ctgtgatgtt tacgaaatgc cttggccttg agcttgcaga atacaatatt     540
cgctgcaaca ttgtatctcc cggatcaacg gaaacagaca tgcagtggtc attatgggcc     600
gacgagaatg gagcggagca agtcataaaa ggatcacttg agacatttaa aacagggatc     660
ccgctcaaaa aactagccaa gccttcggat attgcggatg cggtgctctt tttggtttct     720
ggccaggcag ggcatattac gatgcataat ttatgcgtag atggcggggc gaccttaggc     780
gtgtaa                                                               786

<210> SEQ ID NO 23
<211> LENGTH: 939
<212> TYPE: DNA
<213> ORGANISM: Bacillus subtilis

<400> SEQUENCE: 23
atggctatac ctgccattca gccgtatcaa atgccgacag catctgatat gccgcaaaac      60
aaagtatcat gggtgcctga tccgaatcgg gctgtcttgt taatacacga tatgcaaaac     120
tattttgttg atgctttcac agcgggagcg tctccggtaa cagagctttc agcgaatata     180
cgaaagctga gaatcaatg tgttcagctt gggattcctg ttgtctatac cgcacagccg     240
ggaagccaaa tccggatga ccgtgcgctg ctgacagact ttgggcccg gggattaaac      300 agcggtcctt atgaggagaa aattataacc gagctggcac cagaggatga tgatcttgtg     360
ctgacaaaat ggagatacag cgcgtttaag agaacgaatc tgcttgaaat gatgcgcaaa     420
gagggacgcg atcagctgat cattacagga atttacgccc atatcggctg tcttgttaca     480
gcatgtgaag catttatgga ggatattaaa gccttttttg tgggagatgc agttgctgat     540
ttttcattag aaaaacatca aatggcgctg aatatgcgg ctggacgctg tgcgtttacc      600
gtgatgactg acagtcttct tgatcagctg cagaatgcgc cggcagacgt tcaaaaaacg     660
tcagcaaaca ctggcaaaaa gaacgtgttt acatgtgaga atatccgtaa acaaattgct     720
gagcttctac aagaaacacc ggaagacatc acagatcaag aggatttgct cgatcgtggt     780
cttgattcgg taaggatcat gacattggtg aacaatggc gccgtgaagg ggcagaggtg     840
actttcgtgg aattggctga acgcccaacg atcgaagaat ggcagaaatt gctcacaact     900
cgcagccagc aagtgctgcc aaacgcggat tatttataa                           939

<210> SEQ ID NO 24
<211> LENGTH: 1197
<212> TYPE: DNA
<213> ORGANISM: Bacillus subtilis

<400> SEQUENCE: 24
atgttggatc aaaacgttat aacagaaaca aaagcggagc atttgcttca tgaatatcag      60
ccgggcgcct ttttcttagc gtctcctcat cgtgtactgt tagcgaaagg catatgtgaa     120
```

```
attgtaccgg aggcagacgg gcaaaaccaa atggaaaccc tttctggccg aattgcagag      180
gcgttacgtc aggcaaaaca atcagggcaa agccggccgc ttgttgtcgg ggccgttcct      240
tttgatcaag taaaagcagc gcggctcgtt gtacctgaag aagtgcgctg gtcaggaccg      300
cttcaatttg atcatgagga aaaggaacag caggctgggc atacatacca cataaagcct      360
gttcctgaac ctgaggatta taaaaatggt gttgaacaag ggctggcacg cattgccgat      420
ggaacactca gcaaaatcgt cctgtccaga tcgctgcatt tgacatcgcc tgaaccgatt      480
cagacggatg aattgcttcg ccatctggct cagcataact cgcatggcta cacgtttgcc      540
gcagacgtgt ccagtcagga ggaaacgtct ccccgcagaa cattgctcgg agcaagtccg      600
gagcttctcg tttcaaggat gggaacacag gtcgttccca cccattagc cggctcaaga       660 ccgcgcagta atgatcctgt gaagaccag cgccgggcag ctgaattgct ttctcccgca       720
aaggatcttc atgagcacgc ggttgtcgct gacgcggttg cggcagcgct gagacctttc      780
tgccggacgc tggaggttcc ggagaagcct tcactgatca aaacggaaac gatgtggcac      840
ctgtccagcg tgattaaggg agagcttttcc gacccgtctg taaccgcact gaattggcg       900 gcggcgctcc acccgacgcc agccgtctgc ggaacaccga ctgatcttgc aagagaagcg      960
attctcagca ttgaaccatt tgaccgcggt ttctttaccg gcatggtcgg atggtgtgac      1020
gatgccggtg acggagaatg gatcgtgacc atccgttgtg cagaagcaga gaacgctca      1080 ctccgcctgt atgctggagc tggtgttgtg gccggttcaa agcctgagga cgagcttcag      1140
gagacgtccg caaagtttcg gacaatgctg cgggcaatgg gcgtggatca catatga        1197

<210> SEQ ID NO 25
<211> LENGTH: 1488
<212> TYPE: DNA
<213> ORGANISM: Bacillus subtilis

<400> SEQUENCE: 25
atgagttctt taacgatgca agtgacgaaa aggctggaga catttttaca gggaacaaag        60
aagctttata ttgacggaaa gtttgttccg agtgcctcag gggcaaccctt tgacactcca      120 aacccggcga ccggcgaaac cttgatgacg ctgtatgaag cccaggctgc ggatgtggac       180
aaagctgtta agctgcccg gaaagccttt gaccaaggtg aatggagaac aatgtctcca       240
gcttcgagaa gcagactgat gtataagctg gcagacttaa tggaagagca taaaactgag      300
cttgctcagc ttgaaacact tgataatggg aaaccgatca atgaaacgac taatggagat      360
attccgctgg ctattgagca tatgcgctat tacgccggct ggtgtacaaa ataacagga       420 cagacgattc cggtttccgg cgcttatttt aattatacgc gtcatgagcc tgtcggtgtc      480
gtcggccaga tcattccatg gaatttcccg ctcctgatgg cgatgtggaa atgggcgcg       540 gcacttgcaa caggctgtac aatcgtcctc aaaccggcta acaaacacc gctttcagct       600 ctttatttgg cagaattaat tgaccaagcc ggtttccctg ccggtgtaat caacatcatc      660
ccaggattcg gtgaagatgc gggagaagcg ctgacgaacc acgaagcggt tgataaaatt      720
gcctttaccg gttccactga atcggaaag aaaatcatgt ccaccgcagc gaaaagcatt       780
aagcgtgtga cattggagct gggcgaaaa tcgcctaata ttcttctgcc ggatgcgaat       840
ttaaaaaaag ccatcccggg cgctttaaac ggtgtgatgt taaccaggg ccaagtctgc       900 tgtgcgggct cacgtgtctt cattcataaa gaccaatatg atgaagttgt tgatgaaatg      960
gcatcctatg ctgagtcact ccgccaagga gcgggactcc ataaagatac tcaaatcggg      1020
```

```
cctctcgtaa gcaaggaaca gcatgagcgc gttctttcct atattcaaaa aggaaaagat    1080
gaaggagcaa aagcagtgac cggcggaagc tgtccttttg aagcaggata ttttgtcgca    1140
ccgactgtgt ttgcgaatgt tgaagacgaa atgaccatcg caaagaaaga aattttcgga    1200
cccgtgctga ctgcaattcc gtacgaaaca gtcgatgaag ttattgaacg ggcaaaccat    1260
tcagaatatg gcttgcagc cggactatgg acagagaacg tcaagcaggc tcactatatc    1320
gcggaccgac ttcaagccgg aaccgtttgg gtcaactgct ataatgtgtt tgacgcggcg    1380
tctccatttg gcggttataa acagtcagga ctcggacgag aaatgggatc atatgccttg    1440
gataattaca cagaagtcaa aagtgtatgg gtaaaccttg aagactaa                 1488

<210> SEQ ID NO 26
<211> LENGTH: 1146
<212> TYPE: DNA
<213> ORGANISM: Bacillus subtilis

<400> SEQUENCE: 26
gtgacaggtg tcatatcttc ttcttccatc ggagaaaaga ttaacgaatg gtatatgtac      60
atacgccgat tcagcatacc cgatgcagaa tatttgcgac gagaaatcaa gcaagagctg    120
gatcaaatgg aagaagatca agaccttcat ttgtactatt cactgatgga gtttcggcac    180
aacctaatgc ttgagtacct tgaaccgtta gaaaaaatga ggattgagga acagccgaga    240
ctgtctgatc tgctgcttga gattgataaa aaacaggctc gtttaactgg tctgcttgag    300 tactattta acttcttcag aggcatgtac gagctggacc agcggaata tctgtcggct    360 attaaatttt tcaaaaaggc cgaaagcaag ctgatattcg ttaaggatcg gatagagaaa    420
gctgagtttt tctttaagat gtctgaatct tattactata tgaaacaaac gtattttca    480 atggactatg cacggcaagc atatgaaata tacaaagaac atgaagctta taatataaga    540
ttgctgcagt gtcattcttt atttgccacc aatttttttag atttaaaaca gtatgaggat    600
gccatctcac atttttcaaaa agcttattct atggcagaag ctgaaaagca gccccaatta    660
atggggagaa ctttgtacaa tatcgggctt tgtaaaaaca gccaaagcca atatgaggat    720
gccataccct atttcaaaag agcaatagct gttttttgaag aatcaaatat tcttccttcc    780
ttacctcaag cgtattttt aattacacag atccattata aattaggaaa atagataaa     840 gctcatgaat atcatagtaa gggaatggct tattcacaaa aggccggaga tgtaatatat    900
ttatcagagt ttgaattttt gaatcttta tacttatcag gcccggatga agaagcaatt    960
caaggatttt tgatttttct cgaaagtaaa atgttgtatg ctgatcttga agattcgct     1020 attgatgtgg caaatattat tcatgaacgt aaaaattttc aaaaagcttc tgcttatttt    1080
ttgaaggtgg aacaagtaag gcaacttat caaggaggag tgagtttgta tgaaattgaa    1140
gtctaa                                                                1146

<210> SEQ ID NO 27
<211> LENGTH: 1098
<212> TYPE: DNA
<213> ORGANISM: Bacillus subtilis

<400> SEQUENCE: 27
atgaataaga tcgcacccgc agaaatcgct agcatgctca acgattggta ccttgccatc      60
aagaaacatg aagttgaaga atcctcccgt ttatttgaag aagtgaagcc tttattggat    120
gacatggaag aggatcagga ggtgcttgcc tacttctcct tattggaact gcgccacaag    180
gttttgcttc acgaggcgag aggacagggc tttcagcatg aggagccttc tcatatgaat    240
```

-continued

```
gctacgtctg acatgctgaa atattacttt tttctgtttg aaggcatgta tgaggcctat      300
aaaaataatt atgacattgc cattgggctg tataaagatg cagagcagta tctcgacaac      360
attcccgatc cgattgaaaa agccgaattt cacctgaagg tcggtaagct ctattataag      420
ctgggacaaa atattgtgtc cctcaatcat acacggcaag cagtcaaaac attcagagaa      480
gagacagatt ataaaaagaa gctggcttca gccctgatta ccatgtcagg caattttaca      540
gagatgagcc agtttgaaga agctgaggct tatttggacg aagcaattcg gatcacgagt      600
gaattagagg atcatttttt tgaagcccag cttttgcata acttcggcct tctacatgcg      660
caaagcggca aatcagaaga agcggtttcg aaattagagg aggctctaca gaacgatgag      720
tatgcccgct ccgcctatta ttatcattct gcctacttgc tgatacgaga gctgtttaag      780
atcaaaaaga aagaacaggc cttatcttat taccaagacg tgaaggaaaa attgactgct      840
gagccgaata gaatatgtga ggcaaaaata gacattttat atgccattta tgcagaaggg      900
ggtcatgcgg aaacgtttca cttatgcaaa aacatatgg atgacttgtt gtccgagaaa      960
gagtatgaca gtgtaagaga actttccatt ttggctggcg aacggtatag ggaacttgag     1020
ctttacaaag aagctgccca cttttttat gaagcattac agattgaaga actgattaaa     1080
cgaacggagg ttatataa                                                   1098
```

<210> SEQ ID NO 28
<211> LENGTH: 1296
<212> TYPE: DNA
<213> ORGANISM: Bacillus subtilis

<400> SEQUENCE: 28

```
ttgagtcaag ccataccgtc ttcgcgtgtt ggtgttaaga ttaatgaatg gtataaaatg      60
attcgccagt tcagtgttcc ggatgctgag attctgaaag cggaggttga gcaggacatt     120
cagcagatgg aagaagatca ggatttactg atctattatt ctctgatgtg ttttcggcac     180
cagctgatgc ttgattattt ggagccggga aaaacatacg ggaatcgccc tacagtgaca     240
gagcttcttg aaacgatcga gacccctcag aaaaaactca caggtctttt gaaatactac     300
tctttgtttt tccgcggcat gtatgaattt gaccaaaaag aatatgtgga agcgatcgga     360
tattatcgcg aggcggagaa agaactgccg tttgtgtcag atgatattga gaaagcggaa     420
ttccatttta aagtggcaga agcgtattat cacatgaagc aaacccatgt gtcgatgtat     480
catattcttc aagccttgga catttatcaa aaccatcctc tatacagcat tagaacgata     540
caaagcttgt ttgtgatcgc cggcaactat gatgatttca acattatga taaagcgctc     600 ccgcatttag aggcggcgct ggaattggca atggacattc aaaatgacag gtttatcgcc     660
atttctctat tgaacattgc aaacagctat gacagatcag gagacgatca gatggctgta     720
gaacatttcc aaaaagcggc gaaagtaagc agagagaaag tgcctgatct gcttccgaaa     780
gtcttgtttg gattaagctg gacattatgt aaagcgggcc aaaacacagaa ggcgtttcag     840 ttcatagagg aaggattaga ccatatcaca gcacgttctc acaaattta taagaattg      900 tttctgttct tgcaggccgt gtacaaggag actgttgatg aacgaaaaat tcatgatctt     960
ttaagctatt tcgaaaaaaa gaacctgcac gcttacattg aagcatgtgc ccggagtgct    1020
gccgctgttt ttgaaagcag ctgtcacttt gaacaagcag ctgcgtttta tcggaaagtg    1080
ctgaaagccc aagaagatat tctaaaaggg agagtgttta tatgcctatt aagaaaaaaa    1140
gtgatgatgt gtctggctgt tactctagtt ttcggaagca tgtcgtttcc aaccctgaca    1200
```

-continued

| aactccggtg gatttaagga atcgacagat cgaaatacga cgtatatcga tcattcccct | 1260 |
| tacaaactta gtgatcagaa gaaagccctt agctag | 1296 |

<210> SEQ ID NO 29
<211> LENGTH: 1116
<212> TYPE: DNA
<213> ORGANISM: Bacillus subtilis

<400> SEQUENCE: 29

| atgagtaaga tcgcttctga agttgtcgct actacactga atgactggta cattgctata | 60 |
| aaaaaacaaa aggttgatga atcaataaaa tattattcag agataaagaa acttttttgat | 120 |
| gaaatggaag aagatcaaga agttcttgcg tattatagtc tattagaaga agacataaaa | 180 |
| atgttgctgc attcttcacg aggagagcct ttacaaaagc acacctattt tactgaagac | 240 |
| aatcaaaact tcataacaaa aacaaatgat aaattagaat acaacttta tttatttgaa | 300 |
| gcaatgtacg aggcatacaa caaaaactat gatcgagcaa ttaacctata tggattagct | 360 |
| gagaaaaagc ttgcagaaat tccagatgaa attgaagcag ctgaatttta ctctaaagtc | 420 |
| tcttacttat atactcttgt taaacaaagc attgtggcac aacattatat aaaaaatgca | 480 |
| atttcaatat ataagcgaca ccctgattat aaatgcaaac tagctacatc aacaatgatt | 540 |
| gcagctgcaa actatgctga tatgaaacga tttgaggaag cagaacaata ttacttagaa | 600 |
| gcaattgata ttgcaaaaga aacaaaagat gaatttttaa aagctcaatt atttcacaat | 660 |
| cttagtatcg tttattctga ttggaacaaa cctgataaat gcattgaatc tcttgaaaaa | 720 |
| gcaataggaa atgaatcttg gttacattcg atttattata taaattcttt attcatgatg | 780 |
| attaaagaac tctttaaaat tgacgaaaaa atgaaagcca ttaatttta caataaagca | 840 |
| caggaaagac tcatattaat ggagaataaa gtatacgaag ccaaaatcag catcctgtat | 900 |
| aacctttatt gtgggaatt aaaaaataat ttcaataatt gtattagtaa tattgagttt | 960 |
| ttaaaacagc aaaatgaact tgaaagtgta gatgaattgt cctacatagc tgcaaaaagg | 1020 |
| tttgaatcaa taggtgcttt tgaagaagca acgagctttt tcaatgcgaa aatttgggct | 1080 |
| gaacagaaaa tgaatcaggt ggagggaatc ttatga | 1116 |

<210> SEQ ID NO 30
<211> LENGTH: 1089
<212> TYPE: DNA
<213> ORGANISM: Bacillus subtilis

<400> SEQUENCE: 30

| atgctgaaaa gaacgccgtt atttgacctg tataaggaat atggaggaaa aacgattgat | 60 |
| ttcggaggct gggagcttcc tgttcaattt tcttctataa aaaaagaaca cgaggctgtc | 120 |
| cgaactgcag ccggtttgtt tgatgtatct catatgggag aagtcgaagt gtcagggaac | 180 |
| gacagtctgt cttttttgca aagattgatg acaaatgatg tttccgcgtt aacgccaggc | 240 |
| cgtgctcaat atacagcgat gtgttacccg gatggcggaa ccgtcgatga tttgcttatc | 300 |
| tatcaaaaag gagagaaccg ctatctgctt gtcattaatg cttctaatat agataaagac | 360 |
| ttggcttgga tgaaagaaca tgcagcaggt gatgtgcaga ttgacaatca gtcagatcaa | 420 |
| atcgcgctct ggctgtaca gggaccgaaa gcagaagcga tcttaaaaaa tctgacagat | 480 |
| gcggatgtgt ctgcattaaa gccgtttgcg tttattgatg aagccgatat cagcggccgc | 540 |
| aaagcactta tttcacgcac tggctatacg ggagaagacg ggtatgaaat ttactgccgc | 600 |
| agtgatgatg ctatgcatat ttggaaaaaa atcatcgatg caggggatgc atacggattg | 660 |

```
attccatgcg gtctcggtgc acgtgataca ctccggtttg aagcgaacgt cccgctctac      720
ggtcaggagc tgacccggga tattacaccg attgaagcag gtataggctt tgctgtaaag      780
cacaaaaagg agtctgactt tttcggtaag tcagtattga gtgaacaaaa agaaaacgga      840
gcgaagcgca aacttgtcgg tctcgaaatg attgaaaaag ggataccgcg gcacggatat      900
gaggttttcc aaaatggcaa gtctgtcgga aaggtgacaa ccggcacgca gtcaccgaca      960
ttaggaaaaa acgtcggcct tgccttaatt gattcggaaa cgagtgagat cgggactgtt     1020
gtagatgtag agatacgcaa aaaattagtg aaagcaaagg ttgtcaaaac accatttat      1080 aaacgctaa                                                            1089
```

<210> SEQ ID NO 31
<211> LENGTH: 1347
<212> TYPE: DNA
<213> ORGANISM: Bacillus subtilis

<400> SEQUENCE: 31

```
atgaagcacc gttatttgcc cgcaacagaa aaggataaac aggagatgct tgctactatc       60
ggcgtaagca gcatcgatga tttatttgct gatataccgg aaaacgtcaa atataaaaaa      120
gagcatcaaa tcaaaaaagc gaaatcgag acagaattaa caagagaact gacaaagctg       180
gcctctaaaa atcgtgatac cgtacaatac gcttcttttct taggagcggg tgtatatgac      240
cactatcagc ctgtcattgt ggatcatgtc atttcgcgct ctgagtttta taccgcatat      300
acgccttatc agccagagat tcacaagga gagctccagg ctattttga attccaaacg       360 atgatctgtg aactgacagg catggatatc gccaactcct cgatgtatga cggcggaaca      420
gccttggcag aagcagcaat gcttgcttca ggccacacga aaagaaaaa aattgttgtg      480 tcaaaaaccg tgcatcctga atcgcgagag gtgctgaaaa cttacgcaaa aggtcagtat      540
attgatgttg ttgaagtacc cgctgcggat ggcgttacgg atcttgatgc attgcgccaa      600
accgtttgcg agaacacagc cgcagtgatc gttcagtacc cgaattttt cggcaggatc      660 gagccgctaa aggatattga gcctatcgct catcaaggga atccatgtt tattgtttca      720 gccaacccgc tggcgctagg tcttctcact ccgccgggca agtttcagtc tgatatcgtc      780
gtcggtgatg cgcaccgttt cggcattcct tcagcatacg gcggcccgca ttgcggcttt      840
tttgccgtta ctaaaaaatt aatgagaaag gtgccgggcc gtctcgtcgg acaaacggaa      900
gacgaaaacg gaaaaagagg ctttgtgctt accctgcaag ccagggagca gcatatccgc      960
cgggataaag caacatcaaa tatatgctcg aaccaagctt taatgcgct ggcagcatca     1020 gtggccatga ctgctctcgg aaaaaacggc gtaaagata tagcccgcca aaatctctta     1080
aaagccaact atgcaaagca agaagcaaaa aagcaggcc ttactgttat gtttgacggg     1140
ccgatgttta atgaatttgt catcaaactg atgagccgg tgagagctgt gaacaagcgt     1200
ttgctggcaa aaggcatgat tggcggatat gatcttgggt tgacgtatcc agagctggac     1260
tgccatatgc tgattgctgt aacagagctg agaacaaaag aagaaattga cgcactcatt     1320
caggaattgg gggatcgcca tgagtaa                                        1347
```

<210> SEQ ID NO 32
<211> LENGTH: 705
<212> TYPE: DNA
<213> ORGANISM: Bacillus subtilis

<400> SEQUENCE: 32

-continued

```
atgaatgaga atatgagttt caaagaatta tatgcgattg tcagacacag attcgtgctg      60
attctgctca tcacaatcgg cgtcacccct tattatgggtt ttgtgcaatt taaggtcatt    120
tcaccgacct accaggcgtc gacacaggtg ctggttcatg aatcagacgg tgaagaaaac    180
tcgaatctca gtgacatcca gcgaaatctt cagtatagca gcacgttcca atcgattatg    240
aaaagcactg ccttgatgga agaagttaag gcggaattgc acctatctga atcggcttcc    300
tcgctgaaag gaaagtggt taccagcagt gaaaatgaat cagaaataat caacgttgcc    360
gttcaggatc acgatccggc gaaagcagct gagattgcga cacgttagt gaacaagttt    420 gaaaagaag tagatgaaag aatgaatgta caaggcgtac atatattatc agaggcgaag    480
gcttcggaaa gcccgatgat caagccggcc aggctgcgaa atatggtcat ggcttttggc    540
gctgctgtca tgggcggcat tacactggca ttttttctgc attttctcga tgatacatgc    600
aaaagcgcac ggcagctcag cgagagaacc ggattgccat gcttaggctc cgttcctgat    660
gtccacaaag ggcggaatcg cgggataaaa catttcgggg agtga                    705

<210> SEQ ID NO 33
<211> LENGTH: 684
<212> TYPE: DNA
<213> ORGANISM: Bacillus subtilis

<400> SEQUENCE: 33
gtgatcttta gaaaaagaa agcaaggcga ggtttggctc aaatatctgt tttacacaat      60
aaatcagttg ttgcggaaca atatcgcacc attcggacaa acattgagtt ctcatctgtc    120
cagaccaact tgcgatctat cctcgtcacc tcctctgtgc ctggtgaagg taaatcgttc    180
agtgcagcga atcttgcggc tgtctttgcg cagcagcagg aaaagaaagt actgctggtg    240
gatgccgatt taagaaagcc gaccatcaat cagacgtttc aggttgataa tgtaaccggg    300
ctgacaaatg tgctggtcgg caatgcttca ctcagtgaga cggtgcaaaa gacgccgatc    360
gataacttat atgtactgac aagcgggccg accccgccaa accggcagaa actgttgtct    420
tcaaaagcaa tgggagattt aatatctgag atctatgaac aattcagcct cgtcatcttt    480 gattccctc ctcttttggc tgttgcagat gctcagattc tagcaaatca gacagacggc    540
agcgtgctcg tcgttttaag cggaaaaaca aaaaccgata ccgttctgaa agcaaaagat    600
gcactggaac aatccaatgc gaagctgtta ggcgtctttt aaacaaaaa gaaaatgaaa    660 aaatcggaac actattccta ctag                                            684

<210> SEQ ID NO 34
<211> LENGTH: 1797
<212> TYPE: DNA
<213> ORGANISM: Bacillus subtilis

<400> SEQUENCE: 34
atgattattg cgctggatac ttacctcgtt ttaaattcag ttattgcagg atatcaattt      60
ttaaaagatt cctatcaatt ttatgactcc ggagcattac tgcttaccgc tgtcagcttg    120
ctcctcagct atcatgtgtg tgctttcctg ttcaatcagt ataaacaggt gtggacatac    180
accgggcttg gcgagctgat tgtcctgctt aagggcatta cgctttcagc cgctgtgacc    240
ggcgtcattc agtatgctgt gtatcacacg atgttcttcc gtctgttaac cgcgtgctgg    300
gtgcttcagc ttttgtctat tggagggacc cgtatttat ccagagtatt aaacgaaagc    360
atcaggaaaa aacgctgcgc ctcgtcccgc gcgctgatta tcgggcgggc tcaggtgggg    420
actctgatgg tcaggcagct gctttcgaaa gatgaacctg atatcatacc tgtcgctttt    480
```

```
attgatgacg accaaacgaa gcataaatta gaaattatgg ggctgcccgt aatcggcgga      540
aaagaaagta tcatgcctgc ggtgcaaaag ctcaaaatta attatattat tattgccatt      600
ccttcactcc gcacccatga gcttcaggtg ttatataaag aatgtgtgcg aaccggagta      660
agcattaaaa ttatgcctca ttttgatgaa atgctgcttg cacacgaac tgccggacaa       720 atcagagatg taaaagctga ggacttgctc ggcagaaagc cggtaaccct cgacactagc      780
gaaatttcga accgcatcaa aggaaaaaca gttctcgtca cgggagcggg cggatcaatc      840
ggctcggaaa tctgccgtca gatcagcgcg tttcagccta aggaaatcat tctgctcggc      900
catggggaaa acagcattca ttcgatttat acagagctga acggacgatt cggcaaacac      960
attgtgttcc atacggaaat cgctgatgtg caggaccgcg ataaaatgtt taccttgatg     1020
aaaaaatacg agccgcatgt tgtctatcat gcagctgccc ataagcatgt gcctttaatg     1080
gaacacaatc agaagaggc ggtcaaaaac aatattatcg gaacaaaaaa tgtcgcggaa      1140
gcagccgata tgtcgggaac tgagacattc gtgctgattt catcggacaa agcggtgaac     1200
ccagccaacg taatggggc gacaaaacga ttcgcagaga tgattattat gaatcttggg      1260
aaagtcagca gaaccaaatt tgttgctgtt cgcttcggca atgtactcgg gagccgcggc     1320
agcgtcattc aatttttcaa aaaacagatt gaaaaaggcg gcccggtgac agtaacacat     1380
ccggcaatga cccgctattt catgacgatt cccgaggcat caaggcttgt gattcaggct     1440
ggggcactgg cgaaagggcg tcaaattttc gttctcgata tggagagcc cgtaaagatt     1500 gtggatcttg ccaaaaacct cattcatttg tccggctaca cgactgagca ggttccaatc     1560
gaattcacag gcattcgtcc gggcgaaaaa atgtatgaag aattgctgaa caaaaatgaa     1620
gtccatgctg aacaaatctt tccaaaaatt cacatcggta aagcggtgga cggcgattgg     1680
ccggtgctga tgcgctttat cgaggatttt catgagctgc cggaagccga cctgagagcg     1740
aggctgtttg cggcaatcaa tacatcagaa gaaatgacgg ctgccagcgt tcattag       1797
```

<210> SEQ ID NO 35
<211> LENGTH: 1146
<212> TYPE: DNA
<213> ORGANISM: Bacillus subtilis

<400> SEQUENCE: 35

```
atgacgaaaa agatattgtt ttgcgcgact gttgattatc atttttaaggc ctttcacctc      60 ccttatttta aatggttcaa gcaaatgggc tgggaggttc atgtcgccgc gaacggacaa     120
accaagctgc cgtatgtgga tgagaaattc tccatcccga ttcgcaggtc accttttgac     180
cctcagaacc tggccgttta taggcagctg aagaaagtga ttgacactta tgaatacgac     240
attgtccatt gccatacacc ggtcggcggc gttctcgcca gactggcgg gaggcaggca     300 cggcggcacg gaacaaggt gctgtacaca gcgcacggat ttcacttctg caaggggca      360 ccgatgaaaa attggcttct ttactatccg gttgagaaat ggctttcagc atatacagac    420
tgcctgatta cgattaatga gaggattac atacgggcga aaggacttca aaggccgggc     480
ggaaggacgc agaaaattca cggcattggc gtcaataccg agcgtttccg gcctgtcagt   540
ccgatagagc agcaaagact cagagaaaag cacgggttcc gtgaagatga ttttatattg     600
gtttatccgg ctgagctcaa tctgaacaaa accagaagc agttaattga agccgcagcc      660
ttgctaaaag aaaaaattcc ctcactccgc cttgtgtttg ccggggaagg ggcaatggaa   720
catacgtatc aaacgttagc tgaaaagctt ggtgcctccg cccatgtctg ttttttacggc     780
```

-continued

| | |
|---|---|
| ttttgcagcg acatacatga gttgattcag cttgcggatg tatctgtcgc atccagcatt | 840 |
| agagaaggcc tcggtatgaa tgtgcttgag ggaatggcgg cagaacaacc ggcgatcgcc | 900 |
| acagataatc gcgggcatcg ggaaatcatc cgcgacggag aaaacggttt tctgatcaaa | 960 |
| atcggtgaca gtgctgcttt tgcccgccgg attgaacagc tttaccataa gccggagctc | 1020 |
| tgccgaaagc tgggacagga aggccgaaaa acagccttgc gcttctcgga ggcgcgaacg | 1080 |
| gtggaagaaa tggcagatat ttattccgcg tacatggata tggatacaaa ggagaaaagc | 1140 |
| gtatga | 1146 |

<210> SEQ ID NO 36
<211> LENGTH: 837
<212> TYPE: DNA
<213> ORGANISM: Bacillus subtilis

<400> SEQUENCE: 36

| | |
|---|---|
| atgaactcag gaccgaaagt ttctgtcatt atgggcattt ataattgcga acgcactttg | 60 |
| gcagaaagca tagaatccat actcagccaa tcctataaaa attgggagct gattttgtgc | 120 |
| gatgatgcgt caacagacgg cacgctccgt atcgcgaagc agtatgccgc tcattacagc | 180 |
| gaccgcatca aactgattca aaacaaaaca aataagcggc ttgccgcatc attaaatcat | 240 |
| tgtctttcgc atgcgacagg cgattatatc gaacgtcagg acggagatga cctttcgttt | 300 |
| ccgcgccgtc tggaaaagca ggtcgcgttt ttagaaaagc accgacacta tcaggtggtt | 360 |
| ggcaccggca tgcttgtgtt tgatgaattt ggcgtaagag gcgcccgcat tctgccttct | 420 |
| gttccggagc cgggcatcat ggcaaaaggg actccatttt gccacggcac gattatgatg | 480 |
| agagcgagtg cctaccgcac gctgaaaggc taccggtcgg tgcggcggac gagacgaatg | 540 |
| gaagatattg atttgtggct tcgctttttt gaagagggct tcaggggcta taatcttcag | 600 |
| gaagccttgt ataaagtgag ggaagacagc gatgcattca acggcggtc atttacgtat | 660 |
| tcaatcgaca atgccattct tgtctatcag gcgtgcagac gcttgaagct tcctttatct | 720 |
| gattacatat atatcgcaaa accgttaatt cgcgccttta tgcctgcagc tgtgatgaat | 780 |
| cgctaccata aaaaaagagt gatgaaccaa aggaagggc ttgtcaagca tgaatag | 837 |

<210> SEQ ID NO 37
<211> LENGTH: 1155
<212> TYPE: DNA
<213> ORGANISM: Bacillus subtilis

<400> SEQUENCE: 37

| | |
|---|---|
| atgaatagca gccaaaagcg cgtgctccat gttctcagcg gcatgaacag gggcggcgcg | 60 |
| gaaaccatgg taatgaattt atatcggaag atggacaaaa gcaaagtgca atttgatttt | 120 |
| ttaacgtatc gaaatgatcc gtgcgcttat gatgaagaga ttttatcttt aggcgggcgg | 180 |
| ctttttttatg tcccgagcat tgggcaaagc aatcccctta catttgtgag gaatgtgaga | 240 |
| aacgcgataa agaaaatgg gccgttcagc gccgttcatg cgcacacgga tttccaaacg | 300 |
| ggtttatcg cccttgcggc aaggctcgcc ggagtgccgg tcagggtatg ccactcccac | 360 |
| aatacgtctt ggaagaccgg cttcaactgg aaggatcgat tgcagctgct cgtgttcagg | 420 |
| cggctcattt tggcaaatgc gacagcgctg tgtgcctgcg gagaggatgc gggcaggttt | 480 |
| ttatttggac agtccaatat ggagcgggag cgtgttcacc ttcttcctaa cgggattgac | 540 |
| cttgagttgt tcgccccaaa tgggcaggcg gctgatgaag aaaaagcagc acgcggcatt | 600 |
| gcagccgacc ggctcatcat tggccatgtg gcccggtttc atgaagtgaa aaaccacgcg | 660 |

-continued

| | |
|---|---|
| ttcctgttga agcttgccgc acatctcaag gaaagaggca ttcgctttca gctcgttctg | 720 |
| gcgggagacg ggccgttgtg cggggagata gaggaggagg cgcggcagca gaatttgcta | 780 |
| tcagacgtcc tcttttagg cacggaagaa cggatccatg aactgatgcg aacattcgat | 840 |
| gtatttgtca tgccgtctct gtacgaaggc ttgccggttg tgcttgtgga agcgcaggcg | 900 |
| tcgggcttc catgcatcat ttcagacagc attacagaaa aagtcgacgc cggtctcggg | 960 |
| cttgtcacaa gattaagtct ttctgagccg atcagcgtct gggctgaaac cattgcaagg | 1020 |
| gcggccgccg caggcaggcc gaagcgtgag ttcatcaaag aaacactcgc tcaacttggc | 1080 |
| tacgatgcac agcaaaatgt aggagcgctg ctgaatgtat acaacatcag cacggaaaag | 1140 |
| gaccataacc gatga | 1155 |

<210> SEQ ID NO 38
<211> LENGTH: 1104
<212> TYPE: DNA
<213> ORGANISM: Bacillus subtilis

<400> SEQUENCE: 38

| | |
|---|---|
| atgattgtat atgccgtcaa tatggggatt gtatttattt ggtcttggtt cgctaaaatg | 60 |
| tgcggcggcc gtgatgattc gcttgccacg gggtatcggc cgaataagct tttgatctgg | 120 |
| attccgctcg cttcacttgt gctcgtgtca ggtctccgct atcgagtcgg cacggatttt | 180 |
| cagacgtaca cgctgttgta cgaattggcg ggcgattatc aaaatgtgtg gcagatattc | 240 |
| ggtttcggca cagcgaaaac agcgacagat ccggggttta ccgcactcct ttggctgatg | 300 |
| aatttcatca cggaagatcc tcaaatcatg tatttttacgg tggcggtcgt gacctacagc | 360 |
| tttattatga agacactcgc cgactatggc aggccgtttg agctgagtgt cttttattt | 420 |
| ttgggaacct ttcattatta cgcatctttt aacggcatca ggcaatacat ggtggcagct | 480 |
| gttttgtttt gggcgatccg ttatatcatt agcgggaact ggaagcgata tttcctgatt | 540 |
| gtgctggtca gctcgctctt tcattcgtcg gcgctgatta tgattccagt gtactttatt | 600 |
| gtcagaagaa aagcctggtc accggcgata ttcggcctat ccgctttatt tctcggcatg | 660 |
| acatttttat atcaaaaatt tatttctgtg tttgtcgttg tacttgaaaa cagctcatac | 720 |
| agccattatg aaaaatggct catgacgaac acaaatggaa tgaatgtgat caaaatcgct | 780 |
| gttttggttc tgccgctgtt ccttgcattt tgctataaag aacgactgcg gagtctgtgg | 840 |
| ccgcaaattg atattgtcgt caatttgtgc ctgctaggtt ttttgttcgg ccttttggcc | 900 |
| acaaaggacg tgattttgc cagattcaat atttatttcg gtctgtatca aatgatccta | 960 |
| gtcccttatt tcgtcaggat atttgatgaa aaatcgaacg ctcttatcta tatcgctatc | 1020 |
| gttgtttgtt attttctta cagttatttg cttatgccgg tcgattcatc ggttctgcct | 1080 |
| tacagaacga ttttttcccg gtaa | 1104 |

<210> SEQ ID NO 39
<211> LENGTH: 1077
<212> TYPE: DNA
<213> ORGANISM: Bacillus subtilis

<400> SEQUENCE: 39

| | |
|---|---|
| atgtcgttac aatcgttgaa atcaattttt gcagaatggc tgctgctaaa ggtcaaatac | 60 |
| ccgtcccaat attggctggg agcggcagat caaccggtaa aggccgcagc acatcagaaa | 120 |
| aaaatcatac tgaccctgct gccgtcccat gacaatttgg gagatcacgc aattgcttat | 180 |

-continued

| | |
|---|---|
| gccagcaagg catttcttga gcaagaatac ccggactttg acatcgtcga ggtcgatatg | 240 |
| aaggacattt acaaatcagc aaaaagcctg atccgctcgc gccatccgga ggatatggtc | 300 |
| tttatcatcg gcggcggaaa catgggggat ttataccgtt atgaggagtg gacgcgccgc | 360 |
| ttcatcatta aacattcca tgactatcgg gttgtccagc ttccggcaac ggctcatttt | 420 |
| tctgacacga aaaagggcg caaagagctg aaacgggcac agaaaattta taatgcgcac | 480 |
| cccggcctat tgctgatggc gcgggatgaa acaacgtatc aatttatgaa acagcatttt | 540 |
| caagaaaaaa caattttgaa gcagccggac atggtgctgt atttagacag aagcaaggct | 600 |
| cccgcagaac gcgaaggggt ttatatgtgt ttgcgcgagg atcaggaaag cgtgcttcag | 660 |
| gaggagcaga ggaaccgggt caaggctgcg ctatgtgagg aattcggcga gatcaaatcc | 720 |
| tttacgacaa cgatcggccg ccgggtcagc cgcgatacac gcgaacatga acttgaagca | 780 |
| ctgtggtcta agctgcaaag cgcagaagcc gtcgtcactg acaggcttca tggcatgatt | 840 |
| ttttgcgcgc tgacaggaac gccgtgtgtt gtcattcgct cctttgacca taaggtgatg | 900 |
| gagggctatc aatggcttaa agacatcccg ttcatgaagc tgatagaaca tccgagcca | 960 |
| gagcgcgtaa cagccgcagt caatgagctt ttaacaaaag aaacatcccg tgcaggcttt | 1020 |
| ccgagagatg tgtattttaa aggtctgcgt gacaaaatca gcggtgaagc gcaatga | 1077 |

<210> SEQ ID NO 40
<211> LENGTH: 1035
<212> TYPE: DNA
<213> ORGANISM: Bacillus subtilis

<400> SEQUENCE: 40

| | |
|---|---|
| atgatcccgc tcgtcagcat tattgtcccg atgtataatg ttgaaccatt tatagaagag | 60 |
| tgcattgatt ctttgcttcg tcaaacgctt tctgatattg aaatcatcct cgtgaatgac | 120 |
| ggaacaccgg atcgttcagg cgaaattgca gaggactatg caaaacggga tgcgagaatc | 180 |
| cgggtcattc atcaggcaaa cggcgggctt agttcagcgc gaaatacggg aataaaggcc | 240 |
| gcgcggggca cttacatcgg ctttgtagac ggagacgatt atgtatcatc cgccatgttc | 300 |
| cagaggctga ctgaagaagc ggagcaaaat cagcttgaca tcgtcggatg cggttttttac | 360 |
| aagcagtcat cggacaggcg gacatatgtg ccgccgcagc ttgaggcaaa ccgcgtgctg | 420 |
| acgaaaccag aaatgactga acagcttaaa catgctcacg aaacgagatt tatctggtat | 480 |
| gtatggcgtt atctttaccg tcgtgagctt tttgaaaggg cgaatctgct gtttgatgaa | 540 |
| gacatccgtt ttgctgaaga ctctcccttt aatttgtccg cttttcgcga agcggagcgg | 600 |
| gtgaaaatgc ttgatgaagg attgtacatt tatcgtgaaa acccgaacag cctgacagaa | 660 |
| atcccttata agccggcgat ggatgaacat cttcaaaaac aatatcaggc taaaatcgca | 720 |
| ttctacaatc actacggctt agcaggcgca tgtaaagaag atttgaatgt gtacatttgc | 780 |
| aggcaccagc ttccgatgct tttggcaaat gcctgtgctt ctccgaattc gccgaaagac | 840 |
| atcaaaaaga agatcagaca gattttatcc tatgacatgg tgcggcaggc tgtcagacat | 900 |
| acaccgtttc agcatgagaa attattaaga ggagagcgtt tggtattagc actgtgtaaa | 960 |
| tggcggctca cttttctcat caagctgttt ttcgagcagc gggggacaat gaaaggcagt | 1020 |
| gcgaagcagg catga | 1035 |

<210> SEQ ID NO 41
<211> LENGTH: 1002
<212> TYPE: DNA
<213> ORGANISM: Bacillus subtilis

<400> SEQUENCE: 41

```
atgaaattgt taaaacgaga aggcttgtca ttaactgagg aaaaagcgct gtggatgtac      60
caaagatgc tggagatcag ggctttgaa gacaaagtgc atgaactgtt cgcccaggga      120
gtgcttccg gattcgttca tttatatgcc ggtgaggaag ccgtggctgt agggtgtgc      180
gctcatttac atgatggcga cagcattaca agcacccaca ggggacatgg acattgtatc    240
gccaaaggct gtgacctgga cggcatgatg gcggaaattt tcgggaaagc gaccggattg    300
tgcaaaggca agggcggttc tatgcacatt gcggatcttg ataaaggcat gttaggcgca    360
aatggaatcg tcggggcgg ctttacgctc gcatgcggat cagcgctcac ggctaaatat    420
aaacagacta aaaatgtaag cgtttgcttt tcggggacg gggcaaataa ccaaggtacc    480
ttccacgaag ggctgaattt agcggctgta tggaaccttc ctgtcgtatt tgttgctgaa    540
aacaacggct atggcgaagc taccccattt gagtacgcat cagcctgtga ttcaatcgcc    600
gatcgggcgg ctgcttataa catgccgggg gttacagttg acggcaaaga tattttagca    660
gtttaccagg cagccgagga agcgatagaa agagcaagaa acggcggcgg cccgtctttg    720
attgaatgta tgacctacag aaactacggc catttcgaag gagatgccca aacctataaa    780
acgaaggatg aaagagttga gcaccttgaa gaaaaagatg ccattcaagg ttttaaaaac    840
taccttttaa agaaacaga tgctaataag ctgtcagaca ttgaacagcg tgtcagcgaa    900
tcgattgaaa aagccgtctc gttcagcgaa gacagcccat atccaaaaga ttcggagctg    960
ctgacagatg tgtatgtgtc atatgaaaaa ggaggaatgt aa                     1002
```

<210> SEQ ID NO 42
<211> LENGTH: 1029
<212> TYPE: DNA
<213> ORGANISM: Bacillus subtilis

<400> SEQUENCE: 42

```
atggcgagag tcataagcat gtcagacgcg atcaatgaag caatgaagct tgcgatgaga      60
aaagacgaaa atgtgctttt gatcggtgag gatgtcgccg ggggagcggc ggtcgatcat     120
ttgcaggatg atgaagcatg gggcggtgta ttagggggtca caaagggact cgtacaggaa    180
ttcgggcgta caagagtgct ggacactccg atttctgagg caggctatat gggagcggct    240
atggctgcgg catcaaccgg tttgagaccg attgccgagc tgatgtttaa cgattttatc    300
ggcacgtgct ttgatcaggt gatcaaccaa ggggcgaaat tccgttatat gttcggcgga    360
aaagcgcaag tgccgattac cgtccgcacc acatacggag cagggttccg ggccgctgcc    420
cagcattcac aatcgctgta tggccttttc acgagcatcc ctggactgaa gacagttgtt    480
ccatccaatc cgtatgatgc caaggtgctt ttgcttgcag caatagaaga taatgatccg    540
gtgttttcct ttgaagacaa aacgtcctac aacatgaagg gcgaggtgcc ggaagattat    600
tatacaattc ccctcggaaa agcggatatc aaacgcgaag gcaatgatgt tacgctcttt    660
gcagtcggca agcaggtcaa tactgcgctt gaagcggctg cacagctttc agagaggggc    720
atcgaagccg aggtccttga tccccgcagt ctgtctcctc tggatgagga tgcgattttc    780
acatcgttag aaaaaacaaa ccggctgatc atcattgatg aagccaatcc gcgatgcagc    840
attgccacgg atattgctgc gcttgtcgct gacaagggct ttgatttgct tgatgcgccg    900
attaaacgga ttcagcgcc gcatacaccg gttccgtttt caccagtgct tgaagatcaa    960
tatttgccga caccagataa aattgtcagc gtcacgcttg aattgcttgg cgagccggca   1020
```

-continued

| | |
|---|---|
| ttgaattaa | 1029 |

<210> SEQ ID NO 43
<211> LENGTH: 1197
<212> TYPE: DNA
<213> ORGANISM: Bacillus subtilis

<400> SEQUENCE: 43

| | |
|---|---|
| atggcggtaa aagtagtgat gccaaaattg gaatggcca tgaaacaagg ggaagtatcg | 60 |
| atatggaata aaaagtagg cgacccggtt gaaaagggag aaagcattgc cagcattcaa | 120 |
| tcggagaaaa ttgaaatgga gatcgaagcg cctgaaaaag gaacgctgat cgatatcaaa | 180 |
| gtgaaagagg gagaagaggt tccgcccggc acagctatct gctatatcgg ggacgccaat | 240 |
| gagtcggtgc aggaagaggc gggggcgcct gttgctgaag acaatatgcc gcaagccgtc | 300 |
| cagcccgtca aacaagaaaa caaacccgca gcctccaaaa aagatcgaat gaaaatatct | 360 |
| ccagtcgcca ggaaaatagc agaaaaagca ggattagacc taaaacaact gaaaggaact | 420 |
| ggaccaggcg gacgaatcgt gaaggatgac gtaacaaagg ctcttgctga acagaaaaaa | 480 |
| gatcaagcaa agcctgtttc ggagcagaaa gcgcaggaaa tcccggtgac aggcatgaga | 540 |
| aaggtcatcg ctgcccgaat gcaggaaagc ctggcaaaca gcgcgcagct gacgatcacg | 600 |
| atgaaagctg atatcaccaa gcttgccact cttcaaaaac agctttcacc aactgcggaa | 660 |
| gagagatacg gcacaaaact gacgatcact cattttgtct caagagccgc cgttctcgct | 720 |
| ctgcaagctc accctgtgct gaacagcttt tatcaaaatg agcgcatcat cacacatccc | 780 |
| catgtgcacc ttggtatggc tgtagccttg gaaaatggct tagtggtgcc tgtcatccgc | 840 |
| catgctgaaa agctatcgct gattgaactg gctcaatcca tctcagaaaa tgccaaaaaa | 900 |
| gcacgcgagg gacgtgcggg aagcgaagaa ctgcaaggat ctactttctc cattacaaac | 960 |
| cttggcgcgt ttggagttga gcatttcaca ccgatactaa atccgccgga acaggcatt | 1020 |
| ctcggcatcg gagcaagcta tgacacaccg gtgtatcaag gggaggagat cgtcagaagc | 1080 |
| acgatcctgc cactcagcct gacatttgat cacagagcgt gtgacggcgc ccctgccgct | 1140 |
| gcattcctga aggcgatgaa acatatttg gaagaacccg cagcattaat tttatag | 1197 |

<210> SEQ ID NO 44
<211> LENGTH: 1377
<212> TYPE: DNA
<213> ORGANISM: Bacillus subtilis

<400> SEQUENCE: 44

| | |
|---|---|
| atgacattag ccattatcgg cggcggacct gcaggctatg cggctgcggt ttccgcggca | 60 |
| cagcagggca gaaacgtgct gctcattgac aaaggcaagc ttgggggac ctgcctgaat | 120 |
| gaaggctgca tccgacaaa gtctttgtta gaaagcgcaa acgttcttga taaaatcaag | 180 |
| catgccgaca gctttggaat cgaacttccg gcaggtgcga tatcagtcga ttggagtaaa | 240 |
| atgcaaagcc gaaacaaca ggttgtcagt cagcttgtcc aaggcgttca gtacctaatg | 300 |
| aagaaaaatc aaatacaggt tgtaaaggga acagcctcct ttctttctga agaaagctc | 360 |
| ttgatcgaag gagaaaacgg aaaagaaatc agagaggcgg accaagtatt gattgcctcc | 420 |
| gggtcagagc caatcgagct gccttttgcc ccatttgacg gcgaatggat cctcgacagc | 480 |
| aaagacgcgc tttctctttc cgagattccg tcttcactag tcattgtcgg cggcggtgtc | 540 |
| atcgggtgtg agtatgcagg gctgttcgcc agattggat cgcaggtgac catcattgaa | 600 |
| acagcggacc ggctgatccc ggctgaagat gaagatattg cccgtctctt tcaggagaaa | 660 |

-continued

```
cttgaggaag acggtgtcga agtgcatact tcatccagat tagggcgggt ggatcaaacg    720
gccaaaacgg caatatggaa aagcggtcag cgagagttta aaacgaaggc cgattatgtg    780
ctggtggcga tcggcagaaa accccgtctt gacggattgc agctggaaca ggccggagtt    840
gattttctc caaagggcat tccggtgaat gggcacatgc agacgaacgt gcctcatatt    900
tacgcgtgcg gagatgctat aggggcatt cagctcgcgc atgccgcttt ccatgagggc    960
atcatcgctg cttctcatgc ttccggaagg gatgtcaaaa tcaatgagaa acatgtgccg   1020
cgctgcatct atacgtcccc ggaaatcgcg tgtatcggaa tgacagaacg acaggcaaga   1080
agcatatacg gggatgtgaa gatcggcgaa ttttcatttt ccgcaaacgg caaggcgctc   1140
attaaacagc aagcggaagg aaaggtcaaa atcatggctg aaccggaatt cggcgaaatc   1200
gtgggtgtct cgatgattgg cccggatgta accgagctca tcggccaagc ggcagcgatc   1260
atgaatggtg agatgacggc agatatggcg gagcatttta tcgccgccca tccgacttta   1320
tcggaaacat tgcatgaggc gctgttaagc acgatcggcc ttgcggtaca tgcataa      1377
```

<210> SEQ ID NO 45
<211> LENGTH: 582
<212> TYPE: DNA
<213> ORGANISM: Bacillus subtilis

<400> SEQUENCE: 45

```
atgacagccg tttgtttagt aagacatgga gaaaccgatt ggaacctgca gcaaaaatgc     60
caaggcaaaa ccgatatccc gctaaacgca acaggtgaac gccaagcaag agaaaccgga   120
gaatatgtaa aggactttc ttgggatatt attgtgacga gcccgctgaa aagagcgaaa    180
agaaccgcgg aaattattaa tgaatatctg catcttccga tagtcgagat ggatgatttt    240
aaggaacgcg attacggcga cgcggagggc atgccgctgg aggaacggac aaagcgctat    300
ccagataaca tctatccgaa tatggaaacc ttagaagaac tcactgacag gctgatgggc    360
ggtttggcaa aagtgaatca ggcgtatcca aacaagaagg tgctgatcgt ggcgcacggt    420
gcggcaattc acgccctgct gacagaaata tccggcggtg acccggagct tcaaagcacc    480
cgtctcgtca acgcctgcct cagcaacatt gaatttgcag aagaaaaatg gcggataaaa    540
gactataata tcaacagcca cttatccggc tttatcaaat aa                       582
```

<210> SEQ ID NO 46
<211> LENGTH: 1095
<212> TYPE: DNA
<213> ORGANISM: Bacillus subtilis

<400> SEQUENCE: 46

```
atgaatgcgg ttattgttga tgcaaaacga acgatctttg gaaatcaaaa cggactgctg     60
aagcccttcc tgccggagga tttggcggct cccatcatcc gctgtctcag ccgaaagcta   120
gaggatcaag ttgacgaggt cattctcgga aacgctactg cagaggcgg caacctggcc    180
agactgtcag cccttcaagc cggactgcct ttatcggttc ccggaatgac aattgacaga   240
cagtgcggct ccggccttga agctgtgcgc tatgcctgca gccttattca gcgggagcc    300
ggcacgatgt atatcgcggg cggctcagaa agcagcagcc aatccccttt ttcagaacgg   360
gctcgctttt ctccagatgc gatcggcgat ccagacatgg gcattgcggc agaatatacg   420
gctgcacgct attccatcag cagaagcatg caggatgagt acgcgcttct cagccatcaa   480
cgcagcagga acgcgcatga tgaaggattt taccgtgaag aagttgttgc tctcggggaa   540
```

-continued

| | |
|---|---|
| ttggagacgg acgaagcatt tttgaaaacg cggccaatag aagcgattat tccccgtgca | 600 |
| aagccggttt tcgacaccag ctccggaaca gtcacagcag ccaacagcag tggcatagca | 660 |
| gacggagcag ccgctctttt ggtaatggaa gaagaaaaag cagcagccct gggacttaag | 720 |
| cctgtgcttc ggtttatcgg cagcgctgtc agcggcattc accccaactt tccgcccgcg | 780 |
| gcaccggttg tcgcgattcg tcagctctta catacacacg atgtaacacc tgatgatatc | 840 |
| gatttatttg aaatcaatga agcctttgcc gtcaaaattt gtgtctgctc gcaagaactc | 900 |
| ggcattccct tttcaaaaat caatgtgcgc ggcggcgcct tagctcttgg ccatccgtac | 960 |
| ggtgcatcag gtgcagctct ggtaaccaga ttgttttatg aagcgaaaag acggccagac | 1020 |
| tgtcaatatg ctgttgcagc catcggaagc ggcggcggaa tcggactggc tttattattt | 1080 |
| gaagttcttg catag | 1095 |

<210> SEQ ID NO 47
<211> LENGTH: 1440
<212> TYPE: DNA
<213> ORGANISM: Bacillus subtilis

<400> SEQUENCE: 47

| | |
|---|---|
| atgacaatta ctcataccta ttcatctact gccgaaacat cgcccggccg tgtagcgatc | 60 |
| cagactgaat cggagcaaat cacgtaccat gattgggatc ggcttgtctc tcaaaccgca | 120 |
| aattggctgc ggtcacagcc gagcatgccg aatcgtgtgg cgatcctgct cccaaatagt | 180 |
| ctcgcgtttt tacagctgtt tgccggagcc gcagcggctg gatgtacggc cattcccatc | 240 |
| gacacacgct ggagcccggc tgaatgtaag gagcggctgt ccataagcaa tgcggatctt | 300 |
| gtggttactt tagccttttt caaaaacaaa ctgacagata gccagacacc tgttgtattg | 360 |
| ctggataact gtatggcaga tatttctgag gcagccgctg atcccttgcc taccattgat | 420 |
| ccggagcacc cttttatat gggatttacg tcgggctcga caggaaaaacc gaaggccttt | 480 |
| acgcgatctc accgctcatg gatggagagc tttacctgta cagaaacaga ttttttcgatt | 540 |
| tcatcagatg ataaggttct gattcccgga gcgttaatgt cctctcactt cctatatggg | 600 |
| gctgtcagca ctttgtttct cggaggaacc gttttgtttgc tgaaaaagtt ttctcctgcc | 660 |
| aaagcgaagg aatggctgtg ccgtgaatcc atcagtgttc tctataccgt accgacgatg | 720 |
| acagacgccc tcgcaaggat tgagggtttt cccgacagtc ccgtcaaaat catttcatcc | 780 |
| ggcgcagact ggccggcaga atccaagaag aagcttgccg ctgcatggcc tcatctcaag | 840 |
| ctgtacgatt tttacggcac atcagagctt agttttgtga cgttttcttc accggaagac | 900 |
| agcaaacgga agccgcattc agcgggccgc cctttcata atgtccggat cgaaatccgc | 960 |
| aacgctggag gagaacgctg ccagccagga gaaatcggaa aaatatttgt caaaagcccg | 1020 |
| atgaggtttt ccggctatgt gaacggcagc acaccagatg aatggatgac agtagatgat | 1080 |
| atgggctacg ttgatgaaga gggctttcta tacatatcag gaagagaaaa cgggatgatc | 1140 |
| gtgtacggag gattaaatat ttcccagaa gaaattgaac gtgtgcttct cgcctgccca | 1200 |
| gaggttgaaa gcgcggctgt cgttggcatt cccgacgagt attggggaga atcgctgta | 1260 |
| gctgtcattc ttgaaacgc taatgccaga acactgaaag cctggtgtaa acagaaatta | 1320 |
| gcctcctata aaattccgaa aaaatggtg tttgcagaca gcttgccgga aacgagcagc | 1380 |
| ggaaaaattg cccgttccag agtgaaaaaa tggctggaag agagtgtaca gtataaatga | 1440 |

<210> SEQ ID NO 48
<211> LENGTH: 561

-continued

```
<212> TYPE: DNA
<213> ORGANISM: Bacillus subtilis

<400> SEQUENCE: 48
atgctgaaat taatcgacat gatgcatatt gcgattttca ccgcgctgat ggcagtgctc      60
ggctttatgc cccctctctt cttatccttt acacccgttc cgattacatt gcaaacgctt     120
ggtgtcatgt tggcaggcag cattctcagg ccaaagtctg ctttcttaag ccagcttgtc     180
tttttgctgc tcgtcgcctt cggagcgccg ctgttgcccg gcggacgagg cggttttggt     240 gtgttttcg gaccgagcgc aggcttttg attgcttatc ccctcgcttc atggctgatc      300
agtttagccg ctaacaggct gcggaaggtg acagtattgc gtctcttttt cactcatatc     360
gtattcggca tcatctttat ttatctgctt ggtataccgg tacaagcttt tatcatgcat     420
attgatttgt cacaggccgc cttcatgagc cttgcatatg tgcctggtga tttgataaaa     480
gcggctgtat ctgcatttct ggcgataaaa atcactcaag ccttgtctct ttctgatacg     540
atgtttacaa aaggaggatg a                                               561

<210> SEQ ID NO 49
<211> LENGTH: 1299
<212> TYPE: DNA
<213> ORGANISM: Bacillus subtilis

<400> SEQUENCE: 49
ttgttattta aaaagacag aaaacaagaa acagcttact tttcagattc aaacggacaa       60
caaaaaaacc gcattcagct cacaaacaaa catgcagatg tcaaaaaaca gctcaaaatg     120
gtcaggttgg gagatgctga gctttatgtg ttagagcagc ttcagccact cattcaagaa     180
aatatcgtaa atatcgtcga tgcgttttat aaaaaccttg accatgaaag ctcattgatg     240
gatatcatta atgatcacag ctcagttgac cgcttaaaac aaacgttaaa acggcatatt     300
caggaaatgt ttgcaggcgt tatcgatgat gaatttattg aaaagcgtaa ccgaatcgcc     360
tccatccatt taagaatcgg cctttttgcca aaatggtata tgggtgcgtt tcaagagctc     420
cttttgtcaa tgattgacat ttatgaagcg tccattacaa atcagcaaga actgctaaaa     480
gccattaaag caacaacaaa aatcttgaac ttagaacagc agcttgtcct tgaagcgttt     540
caaagcgagt acaaccagac ccgtgatgaa caagaagaaa agaaaaacct tcttcatcag     600
aaaattcaag aaacctctgg atcgattgcc aatctgtttt cagaaacaag cagatcagtt     660
caagagcttg tggacaaatc tgaaggcatt tctcaagcat ccaaagccgg cactgtaaca     720
tccagcactg ttgaagaaaa gtcgatcggc ggaaaaaaag agctagaagt ccagcaaaaa     780
cagatgaaca aaattgacac aagccttgtc caaatcgaaa agaaatggt caagctggat     840 gaaatcgcgc agcaaattga aaaatcttc ggcatcgtca caggcatagc tgaacaaaca     900
aaccttctct cgctcaatgc atctattgaa tccgcccgcg ccgagaaca cggcaaaggc     960 tttgctgtcg tggcaaatga agtgcggaag ctttctgagg atacgaaaaa aaccgtctct    1020
actgtttctg agcttgtgaa caatacgaat acacaaatca acattgtatc caagcatatc    1080
aaagacgtga atgagctagt cagcgaaagt aaagaaaaaa tgacgcaaat taaccgctta    1140
ttcgatgaaa tcgtccacag catgaaaatc agcaaagagc aatcaggcaa atcgacgtc    1200 gatctgcaag cctttcttgg agggcttcag gaagtcagcc gcgccgtttc ccatgtggcc    1260
gcttccgttg attcgcttgt catcctgaca gaagaataa                           1299

<210> SEQ ID NO 50
```

<211> LENGTH: 1350
<212> TYPE: DNA
<213> ORGANISM: Bacillus subtilis

<400> SEQUENCE: 50

| | | | | | |
|---|---|---|---|---|---|
| atgaagaaaa | aatcattctc | aatcgtaata | gcgggcggag | ggagcacttt | cactccaggg | 60 |
| atcgtactca | tgctcttgga | ccatttggag | gagtttccga | tcagaaagct | gaagctgtat | 120 |
| gataatgata | aggagagaca | ggatcgaatt | gcaggcgcct | gtgacgtttt | tatcagagaa | 180 |
| aaagcgccgg | atattgaatt | tgcagcgacg | actgacccgg | aagaagcttt | tacagatgtc | 240 |
| gattttgtta | tggcgcacat | cagagtaggg | aaatacgcga | tgcgcgcgct | tgatgagcaa | 300 |
| attccgttaa | agtacggagt | tgtcggccag | gagacgtgcg | ggccgggcgg | gatcgcatac | 360 |
| ggtatgcgtt | cgatcggcgg | tgtgcttgaa | atattagatt | acatggaaaa | atactcgcct | 420 |
| gatgcgtgga | tgctcaatta | ttccaatccg | gcggcaattg | tggctgaagc | tacgagacgc | 480 |
| cttagaccga | attctaaaat | tctcaatatc | tgtgatatgc | cggttgggat | cgaagaccgg | 540 |
| atggcgcaaa | tcttggcttt | atcctcaaga | aaagaaatga | aggtccgcta | ttacggattg | 600 |
| aatcatttcg | gctggtggac | atcgattcag | gatcaagagg | gcaacgattt | aatgccgaag | 660 |
| ctgaaggaac | atgtatccca | atacggttat | attccgaaaa | cagaggctga | agctgtggag | 720 |
| gcaagctgga | atgacacgtt | cgccaaagcg | cgtgacgtgc | aggctgcaga | tcctgacaca | 780 |
| ctgccgaata | cgtatttgca | atattatttg | ttcccagatg | atatggtgaa | aaaatcaaat | 840 |
| ccgaatcata | cgcgggcgaa | tgaagtcatg | gaagggcgcg | aagcttttat | tttcagccaa | 900 |
| tgtgacatga | tcacacgtga | acagtcctcg | gaaaacagcg | aaattaaaat | cgatgaccac | 960 |
| gcatcgtata | tcgttgatct | tgcccgggcg | attgcctaca | cacaggtgaa | agaatgctg | 1020 |
| ttgattgttg | aaaataacgg | tgcaattgcg | aactttgacc | cgactgcgat | ggttgaggtg | 1080 |
| ccatgcatcg | tcggctcaaa | tggacctgaa | ccgattaccg | ttggcaccat | tccgcaattc | 1140 |
| cagaaagggc | tcatggagca | gcaggtatcc | gttgagaagc | tgactgttga | agcgtgggca | 1200 |
| gagaaatcgt | tccaaaagct | gtggcaggcg | ctgatcctgt | caaaaacagt | gccgaacgcg | 1260 |
| cgtgtggcaa | gactcattct | tgaggattta | gtggaggcca | acaaagactt | ctggcctgag | 1320 |
| cttgatcaaa | gcccaacccg | catatcataa | | | | 1350 |

<210> SEQ ID NO 51
<211> LENGTH: 1584
<212> TYPE: DNA
<213> ORGANISM: Bacillus subtilis

<400> SEQUENCE: 51

| | | | | | |
|---|---|---|---|---|---|
| atgatgcaaa | aaattcagcg | ctttggaagc | gcgatgtttg | tgcctgtttt | attattcgcg | 60 |
| ttcgccggca | ttatcgtcgg | tatcagcacg | ctctttaaaa | ataaaaccct | catgggaccg | 120 |
| ctcgccgatc | ctgacggttt | ttggtatcag | tgctggtata | tcattgagca | gggcggctgg | 180 |
| actgttttta | accaaatgcc | gctcttattc | gccattggca | tcccggttgc | tttggcgaag | 240 |
| aaagctcagg | cacgcgcctg | tttggaagcg | cttactgtct | acctgacatt | caactatttt | 300 |
| gtcagcgcga | tattgacggt | atggggagga | gcatttggcg | tcgacatgaa | tcaagaggtc | 360 |
| ggcggaacga | gcgggttaac | gatgattgcg | ggcataaaaa | cgctcgatac | caacatcatc | 420 |
| ggagccatct | ttatttcttc | gattgtcgtc | tttttgcata | atcgctattt | tgataaaaaa | 480 |
| ctgcccgatt | ttctcggcat | ctttcaaggc | tcaacatata | tcgtgatgat | ttccttcttt | 540 |
| attatgatcc | caattgcgtt | ggctgtgtct | tatatttggc | cgatggttca | atcgggaatc | 600 |

-continued

```
ggctcgcttc aaagcttcct ggttgcttct ggggcggtgg gcgtttggat atacacgttt       660
ttggaacgga tttttaattcc gaccggcctt catcactttta tttacacgcc gtttatttat     720
ggcccggctg tagcggaagg cgggatcgtc acgtattggg cacagcatct cggcgaatat      780
tcgcaaagcg ccaaaccgct gaaggagctc tttccgcaag gcggattcgc gcttcacggc      840
aactcgaaaa tcttcggtat tccgggtatc gccctggctt tttatgtgac agccaaaaag     900
gaaaagaaaa aactcgtcgc agggctgctg attcctgtca cactgacagc gattgtcgcc     960
ggtattacag agccgattga gtttacgttc ttattcattt cacctttctt atttgcggtt    1020
cacgccgtgc ttgccgccac aatgtcgaca gttatgtata tggccggcgt cgtcggaaat   1080
atgggaggcg gactgattga ggcggtaacc ttgaactgga ttccgctctt tggcagccac   1140
ggtatgacat atgtgtatca aattttgatc gggctctcgt ttacagcaat ttattttttc   1200
gtcttcagat ttttaatcct caaattcaat atcgctacac caggacggga aaaggatgaa   1260
cagcaggaaa caaagctata ttcgaaaaag gaatacagag aacgaaaaaa caaggatgaa   1320
acggcctccg ctgctgaaac ggctgatgac accgcttttc tgtatattga agcgctgggc   1380
ggaaaagaca acatcactga agtcacaaac tgcgccaccc gcctcagagt cagtgtcaag  1440
gatgaaacaa aggttgaacc cgacagcgta ttccgcgcgc ttggcgcaca cggcgttgtc  1500
aggaacggga aggcgtttca ggtaattatc ggattaagcg tgccgcagat gcgggagcgt  1560
gtggaaaaaa tattgaatca ataa                                         1584

<210> SEQ ID NO 52
<211> LENGTH: 1365
<212> TYPE: DNA
<213> ORGANISM: Bacillus subtilis

<400> SEQUENCE: 52
gtggaactga tcatcattct attggcgtta ggtttgctga tgtttacggc gtatcgggga      60
ttttctgtca tattgtttgc gccgatttgc gcgttattcg cggtgctgct gacagatcca    120
agccatgtgc ttcctttttt ttcatcaatt tttatggaga agatggcggg ttttattaag    180
ctgtatttcc cagtgttttt gctcggtgct attttttggaa aggtcgttga aatggccggg    240
cttgcggcat caatcgcgaa acaattgtc cggcttgtcg gggcaaaaag agcgatactt    300
gccattgtgc tgatgggtgc tgtcttgacg tacagcggtg tcagcctgtt tgttgtcgta    360
tttgctgtat atccttttgc gaaaaacatg ttccaagaag caaacatacc aaaacgcctc   420
atcccgggta cgattgcttt aggagctttt acgtttacga tggacgcact tccgggaacg   480
ccgcaaatcc aaaatgtcat cccgacgtcg tttttcaaaa cagacattta tgccgcccct   540
tggctgggtt tgatgggcgc agtgattgtg ctggcagctg ggatgctcta tttggaatca   600
aggcggaaga aagcgcaggc atctggcgaa ggctatggcg gtttttgattc gcagaatgct   660 cctgctcctg aatcgattga gtccgcggct gaaccggaca aaagcccgat tcggcacgcc   720
cttgcctttg tcccgcttat cctcgtcggt gcagtgaata aatatttcac catttacctg   780
ccaaagtggt atccgaatgg atttaatttt ccttccatag gattaaagga gttcggcagg   840
cttgatattt cttcagcggc tgctatttgg tcggtggaga ttgctttagt gattggcatc   900
atcacaacga tattttga ttggagaagt gtgtttgccc aattgaagga agggctgaat    960
gaaggaattg gcggcgcctt gctggcatct atgaatacgg gtgctgagta cgggttcggc   1020
ggcattatcg ccgcgctgcc ggggtttcat aagctgagca gcggaatttc acatactttt   1080
```

-continued

| accgatccgc | ttgtaaatgg | cgccgttacg | acaactgcgc | tggcgggaat | caccggctcg | 1140 |
| gcttcgggag | gaatgggcat | tgcgttaagc | gcgatgtcag | aacaatactt | acaggcgatt | 1200 |
| caggcttaca | atattccgcc | agaggtgatg | catcgggtca | tttcaatggc | atcaggcggg | 1260 |
| atggatacac | tgccgcataa | tggcgccgtt | atcacgcttt | ctggccgtga | cgggtttgac | 1320 |
| ccaccggcaa | tcctatcgcg | atattttgc | gatcacgctc | attaa | | 1365 |

<210> SEQ ID NO 53
<211> LENGTH: 717
<212> TYPE: DNA
<213> ORGANISM: Bacillus subtilis

<400> SEQUENCE: 53

| atgggaaaag | tgctgtcatc | aagcaaggaa | gctgcgaaac | tgattcatga | tgggggatacg | 60 |
| ctgatcgcgg | gagggtttgg | gctgtgcggc | atccctgaac | agctcatttt | gtctataaga | 120 |
| gatcaggag | taaaggattt | aaccgttgtc | agcaataact | gcggagtcga | tgactggggg | 180 |
| cttggtttgc | ttctggctaa | caagcaaatc | aagaaaatga | tcgcttccta | tgtcggtgaa | 240 |
| aataaaattt | ttgagcggca | gttttaagc | ggagagcttg | aggtagagct | tgttccccaa | 300 |
| ggaacgctcg | ctgagagaat | tcgtgcaggc | ggtgcaggca | taccgggatt | ttatacggcg | 360 |
| acaggcgtcg | gcacctccat | agccgaggga | aaagaacata | aaacattcgg | cggccggact | 420 |
| tatgtgctgg | agcgaggcat | taccggcgat | gtggcgatcg | tcaaagcgtg | gaaagcggac | 480 |
| accatgggca | atttgatttt | taggaaaacg | gcgagaaatt | tcaatcccat | tgccgccatg | 540 |
| gcaggcaaga | tcacgattgc | cgaggcggaa | gaaatcgtgg | aagcaggaga | gctcgatcca | 600 |
| gatcacatcc | atacgccggg | aatttacgta | cagcatgtcg | tgcttggcgc | gagccaagaa | 660 |
| aaacggattg | aaaaacgaac | agttcagcaa | gcatcgggaa | agggtgaggc | caagtga | 717 |

<210> SEQ ID NO 54
<211> LENGTH: 651
<212> TYPE: DNA
<213> ORGANISM: Bacillus subtilis

<400> SEQUENCE: 54

| gtgaaggaag | cgagaaaacg | aatggtcaaa | cgggctgtac | aagaaatcaa | ggacggcatg | 60 |
| aatgtgaatc | tcgggattgg | aatgccgacg | cttgtcgcaa | atgagatacc | cgatggcgtt | 120 |
| cacgtcatgc | ttcagtcgga | aaacggcttg | ctcggaattg | gccctatcc | tctgaaagga | 180 |
| acggaagacg | cggatttgat | caatgcggga | aaggaaacga | tcactgaagt | gacaggcgcc | 240 |
| tcttattttg | acagcgctga | gtcattcgcg | atgataagag | gcgggcatat | cgatttagct | 300 |
| attctcggcg | gaatggaggt | ttcggagcag | ggggatttgg | ccaattggat | gatcccgggc | 360 |
| aaaatggtaa | aagggatggg | cggcgccatg | gatctcgtca | acggggcgaa | acgaatcgtt | 420 |
| gtcatcatgg | agcacgtcaa | taagcatggt | gaatcaaagg | tgaaaaaaac | atgctccctt | 480 |
| ccgctgacag | gccagaaagt | cgtacacagg | ctgattacgg | atttggctgt | atttgatttt | 540 |
| gtgaacggcc | gcatgacact | gacggagctt | caggatggtg | tcacaattga | agaggtttat | 600 |
| gaaaaaacag | aagctgattt | cgctgtaagc | cagtctgtac | tcaattctta | a | 651 |

<210> SEQ ID NO 55
<211> LENGTH: 774
<212> TYPE: DNA
<213> ORGANISM: Bacillus subtilis

<400> SEQUENCE: 55

```
atgagaaaac aagtcgcttt ggtgacaggg gctgccggcg gaatcagatt cgaaatcgca      60
agagaattcg cccgggaagg tgccagcgtc atcgtttcag acctccgtcc ggaagcatgt     120
gaaaaagcag cctccaagct tgcagaagaa ggctttgacg cggcggccat tccgtatgat     180
gtgacaaagg aagcgcaagt tgctgatacg gtgaacgtca tccaaaaaca atacggccgc     240
ttggatattc tggtgaacaa tgccggtatt cagcacgtcc ctccgattga agagtttccg     300
acagacacct ttgaacagct gatcaaggtc atgctgacgg ctccctttat tgcaatgaag     360 catgttttc cgatcatgaa aaaacagcag tttggcagaa tcattaatat tgcgtctgtt     420
aatggattag tgggctttgc agggaaatcc gcttataata gcgccaagca cggcgtcatt     480
ggactcacaa aagtaggggc gctggaaggc gcgccccacg gcataacagt caatgcgctc     540
tgtccgggtt atgtcgatac ccagcttgta cgcaatcagc ttagcgatct atcgaaaact     600
agaaatgtcc cttacgactc tgtacttgaa caagtcattt ttccgcttgt gccgcaaaag     660
cgactgcttt ccgtcaagga aattgcggat tatgccgtgt ttttggcaag cgagaaggcg     720
aagggcgtca ctgggcaggc tgtcgtcctt gatgggggct acaccgcaca atga           774
```

<210> SEQ ID NO 56
<211> LENGTH: 1788
<212> TYPE: DNA
<213> ORGANISM: Bacillus subtilis

<400> SEQUENCE: 56

```
atgtcacggc tccttgtgac cttatgccaa agcagagga actggccgca gccatttctg      60
ccaacggacc gatcgctgtc cgtcaggcta aatttgcaat caataaagga ttggagacag     120
atcttgctac aggccttgcg attgaacaaa aagcgtatga acaaaccatc ccgacaaaag     180
acaggagaga agggcttcag gcctttcaag aaaaaagacg ggccgtatac aagggaatat     240 aaagggagg caatgctgat ggattatgaa aaggaacgaa cagaacgggc tgaacggatt     300
cgaaaaggcg gagcggaaaa gtatcatcaa agcaatcggg aaaaaggcaa gctctttgtc     360
agagagcggc tttcccttct ctttgacgat gacattgagc tagaagacgc tttttttgcg     420
gaatgtatgt cagacgggct tcccgctgac ggagttgtaa ccgctatcgg caaaatcggc     480
ggccaaaccg tttgcgtcat ggcgaatgat tcaacagtga agcggggtc atggggagca     540 aaaacagttg aaaaaatcat cagaattcaa gaaatcgccg aaaaattaaa ctgtccgctc     600
atttatttag tcgattcggc aggcgcccga attaccgacc aaatcaatgt cttttccaggg     660 agacgcggtg caggaagaat ttttttacaat caagtcaaat tatcgggacg cattccgcaa     720
atctgtctgc ttttcggacc atctgcggca ggaggcgctt atattccggc cttctgtgat     780
atcgtcgtta tggtagacgg taacgcctcc atgtatttag gttcgccaag gatggcggaa     840
atggttattg gagaaaaagt gtctctcgaa gaaatgggtg gcgcccgtat gcattgctca     900
atctccggct gcggagatat tcttgcagaa actgaagaag aagccataca gctggtgcgg     960
gcttatttgt cttactttcc ggcaaatttt caagaaaaag cgcccattca tgagaaacgc    1020
ccgccaaaac acttcgaaac tccgcttgcc gacgtcattc cgcaaaatca aaacgcacct    1080
tttgatatgc atgagctcat tgagcgggtc atagatgaag actcattttt tgagatcaaa    1140
gccttatttg caccggaatt attgacgggc ctcgcacgaa tccacggaca gcctgtcggc    1200
attgttgcaa accagccgaa ggtaaaagga ggcgtcttat tccacgattc agcagacaaa    1260
gcggctaagt ttattaccct tatgtgacgct tttcatatcc cattgctgtt cttagccgat    1320
```

```
atccccggtt ttatgattgg cacaaaagta gaacaggctg ggattatcag acacggagcg    1380
aaaatgattt ctgcgatgtc ggaggcaact gttccaaaac tctctgtcat tgtccgaaaa    1440
gcttacgggg cggggttgta tgcaatggca gggccggcat ttgaaccgga ttgctgtcta    1500
gcgctcccaa ccgcccaaat cgccgtcatg ggccctgagg ccgctgtaaa cgctgtctac    1560
gctaaaaaaa tcgccgagct gccagaagaa gagagagccg catttatcag cagcaaacgg    1620
gaggaataca agaggacat caatatctac cgtctggctt cagaaatgat cattgatgct    1680
gttatcccag ccaattcgct gcgtgatgag ctggccaaac ggctcaaggc atacatgaca    1740
aaggaaatga catttaccaa tcgaaagcat ccggtttatc cggtgtaa                1788

<210> SEQ ID NO 57
<211> LENGTH: 783
<212> TYPE: DNA
<213> ORGANISM: Bacillus subtilis

<400> SEQUENCE: 57
atgggagatt ctattctttt tactgttaaa aatgaacata tggcgttgat caccttaaac      60
aggcctcagg cagcaaatgc tctttcagcg gaaatgctta gaaacctgca atgattatc     120 caggaaattg aatttaactc aaacatccgt tgcgtcatcc tcacaggcac cggtgaaaaa    180
gcgttttgtg caggggcaga cctgaaggaa cggataaaac tgaaagaaga tcaggttctg    240
gaaagtgtat ctctcattca agaacggcg gctttacttg atgccttgcc gcagccggtc     300
atagctgcga taaatggaag cgcattaggc ggcggactag aattggcatt ggcatgcgac    360
cttcgaatcg caactgaagc agctgtgctg ggacttccgg aaacagggtt agctattatc    420
ccgggcgctg gagggaccca aaggctgccc ggctgattg gcagaggaaa agcaaaagaa     480 ttcattttata caggcagacg cgtgaccgca cacgaagcaa agaaatcgg ccttgtagag    540 catgtcacgg ctccttgtga ccttatgcca aaagcagagg aactggccgc agccatttct    600
gccaacggac cgatcgctgt ccgtcaggct aaatttgcaa tcaataaagg attggagaca    660
gatcttgcta caggccttgc gattgaacaa aaagcgtatg aacaaaccat cccgacaaaa    720
gacaggagag aagggcttca ggcctttcaa gaaaaaagac gggccgtata caagggaata    780
taa                                                                   783

<210> SEQ ID NO 58
<211> LENGTH: 900
<212> TYPE: DNA
<213> ORGANISM: Bacillus subtilis

<400> SEQUENCE: 58
atgccatatc ctaaaaaagt gacaatcaaa gaagtcggcc cgcgtgatgg cttacaaaac      60
gagcccgttt ggatcgcaac agaggataaa ataacctgga tcaaccagct ttcccggaca    120
gggctgtcgt atattgaaat cacatccttc gttcacccga atggattcc ggcgcttcga      180 gatgctatcg atgtagcaaa aggcatcgac cgagaaaaag gggtaacgta cgcggcactt    240
gtcccgaatc aaagaggact ggagaatgca cttgaaggag gcattaacga ggcttgcgtt    300
tttatgtccg ccagcgagac gcacaacaga aaaacatca ataaatccac ttctgaatcc     360
ctccatatac tcaaacaagt aaacaacgac gcacaaaaag caaacctcac aacaagagcc    420
tacctctcga ctgttttcgg ctgtccgtac gaaaaagatg tccccattga caagtcatt     480 cgcctttcag aagctctatt tgaatttggg atttctgaac tgtcgcttgg agatacgatt    540
ggagcagcta atcccgccca agtggaaact gtacttgaag ctcttttggc acgattcccg    600
```

```
gctaatcaaa ttgccctgca ttttcatgat acgagaggaa ccgctctggc caacatggtc      660
acagcactcc aaatgggcat cacggtgttc gacggctcgg caggcgggct tgggggatgc      720
ccatatgcgc caggttcatc aggaaacgcc gcaactgagg atatcgtgta catgcttgaa      780
cagatggata tcaaaacaaa tgtaaagcta gaaaaactgc tatctgcggc caaatggatt      840
gaagaaaaaa tgggcaaacc gctgccgagc agaaatttac aggtgtttaa atcatcttga      900

<210> SEQ ID NO 59
<211> LENGTH: 1335
<212> TYPE: DNA
<213> ORGANISM: Bacillus subtilis

<400> SEQUENCE: 59
atgtttacaa aagtactgat cgccaaccgc ggtgaaattg caatgagaat tatccgaaca       60
tgcagccgtc tcggcattaa aacggtcgct gtttattcag aagcagacaa ggacgcgccc      120
catacaaaag ccgctacaga ggcatatttg atcggggaat cgagagtcag tgaaagttat      180
ttaaatatag agagaatcat aaagacggcg aaaaaagcaa aagccgacgc gatccacccg      240
ggatatggat tgttatcaga aacagccgg ttcgctgaac gctgcaagca agaaaacatc      300
gtgtttatcg gaccttcccc tgatatcatc gcaaagatgg gcagcaaaat tgaagcgcga      360
aaagcaatgg aggctgcagg tgtccctgtg gtgccgggcg tttctgaatc cctcggagat      420
atagaggcag cctgccgcac cgcaagtcaa atcggctatc ctgtcatgct gaaagcttca      480
gcgggcggag gcggcatcgg aatgcagcgt gttgaaaatg aagaagcatt aaaaaaagcg      540
tacgagggaa acaaaaagcg cgcagcgat tttttcggtg acgggtctat gtatatagaa      600
aaagttattg aacatgcgcg ccacatcgag gttcagcttt tggccgatca acacggccat      660
acagtacatc tgtttgaacg tgattgctct gttcagaggc gccaccaaaa agtcattgaa      720
gaagcaccgt ctccatttgt agacgatgaa ctaagaatga agatcggtca aacagcggta      780
aaagcagcga aggcaatcgg ctatacgaac gcaggcacca tcgaatttat agttgaccag      840
aaacaaaatt tttatttcct cgaaatgaat acgagactgc aagttgaaca ccccgtgact      900
gaagaaataa caggcctgga cttagttgag cagcagctgc ggattgctgc gggccataca      960
ctcacattct cccaaaaaga catccaacgg aacgggcatg cgatagaggt tcgaatatac     1020
gcggaagatc ccaagacctt cttcccgtca ccaggtacga tcactgcgtt ttcacttcct     1080
gaccaaaaag gagtcagaca cgaatgtgcg gtagcaaaag acagcaccgt tacccctttt     1140
tatgacccga tgatcgctaa gatgattgtc aaaggccaaa ccagaacaga agcaattgaa     1200
aaactagaga cagcgcttcg cgactatcgt gtagaggaa tcaaaacaaa ccttccgctc     1260
ctcatacagg ctgcggcaac aaaggcattt aagaagggg atgtcacgac tgactttttg     1320
aaacagcacc tataa                                                      1335

<210> SEQ ID NO 60
<211> LENGTH: 1650
<212> TYPE: DNA
<213> ORGANISM: Bacillus subtilis

<400> SEQUENCE: 60
atggctgaac tcatccattc cacaatcggc aggctgctgg aacaaacagc tgatgcgtat       60
cccgatcgag atgctgttgt gtatccagac cgaaatatcc gctatacgta cgctcaattt      120
gacagtctgt gccgtcaaac cgctaaaggt ctcatgcgga tggggattgg aaaaggagac      180
```

-continued

```
cacgtcgcca tatgggcttc taatatctct gaatggcttg ccgtccagtt cgcaactgcg      240
aagatcggag ccgtgctcgt gaccgtcaat accaattatc aagcacatga gcttgattac      300
ttgttaaagc aatcggatgc cgcggcgctt attatcatgg attcatacag ggcacttct       360 tatccagaca tcgtgaacag tttaattcca gaactgcaag aagcaaagcc cggccaactg      420
aaatctgaac gctatccctt tttaaaaacg ctgatctata ttggcaataa cgattgtct       480 ggcatgtatc attgggacga tacagagata ttggcgaaaa cagtgacaga tgctgagctt      540
gaagagagaa tgaacagcct ggataaagac aatgtgatta atatgcaata cacatcagga      600
acgacagggt ttccaaaagg cgtgatgctg acccatttca atgtcatcaa taacgctgct      660
aatatcgctg aatgtatggc tttaacctct caagaccgca tgtgcatccc tgttccgttt      720
tttcactgct ttggatgcgt ccttggggtt ttggcatgtg tatccgtcgg ggcagccatg      780
atacccgtgc aagaatttga tcccgttacc gtccttaaaa cggtagaaaa agagaaatgc      840
acagtgctcc atggtgtgcc taccatgttt atcgccgagc tgcatcatcc ggattttgat      900
gcatatgatc tatcgacgct ccgaacagga atcatggccg ctctccctg tccaagtgaa       960 gtgatgaaag ctgtgattga aggatgggc atgaaagaca ttacgatcgc ctatggacaa       1020
accgaagcct cgccagtcat tacacaaacg agagcaaatg attccttcat aagaagagtc      1080
gaaacaaccg gccgtgccct gccacatact gaggtgaaaa ttgtagaacc cgggacatgt      1140
caagaagttc aaagaggcat gcagggagaa ctgtgcaccc gtggctatca cgtcatgaaa      1200
ggctattata aagacaaaga tgcgaccaga aaagcaatca atcatgacgg atggctgttt      1260
accggagatc ttgctgtcat ggatgaagac gggtactgcc gcatcaccgg aagattaaaa      1320
gatatgctca tcagaggcgg cgagaacatt tatccgcggg aaattgaaga attttatac       1380 cagcatcccg ctgttttaga tgtacaggtg gttggtgtgc ctgacgccaa attcggggag      1440
gaagctgcag cctggattaa actgaaagac ggtaaaagcg tttcacctga tgagcttaaa      1500
gcctattgca aagggaaaat cgcccgccac aaaattccgc gttatgttat ttttacggat      1560
gactatccga tgacggcctc aggcaaaatt caaaaatata aactgcgaga aaaaacgatt      1620
gaaatgttca acttatcatc aagtcaatga                                       1650
```

<210> SEQ ID NO 61
<211> LENGTH: 1014
<212> TYPE: DNA
<213> ORGANISM: Bacillus subtilis

<400> SEQUENCE: 61

```
ttgaaaacga taacaattgc agctgaagaa gcaaaggaac tcgtttggca aaagctggac       60
ggtgccggtt tgaatgaacg agatgctgaa aaagtggcag atgttctcgt gcacgctgat      120
ttgcgcaatg tacattcgca tggcgtgctg cacacagaac actatgtgaa caggctttta      180
gcgggaggga tcaatcctgg ggcacagcct gttttttaaag agacggggcc tgtgaccggg      240
gtgcttgacg gagacgatgg tttcggtcat gtgaattgcg acatggcgat ggaccatgca      300
attgacatgg cgaagaaaaa aggagtcggc atggtcacgg ccgtaaacag cagccattgc      360
ggagcgctaa gctattttgt gcaaaaagcg gctgacgaaa agctgatcgg aatggcaatg      420
acgcatacag acagtatcgt tgtcccattt gggggggagga ctcctatttt agggacaaat      480
ccgattgctt acggagttcc ggctaagcat aaaaaaccgt ttatcctaga tatggcgaca      540
tccaaagtgg cttttgggaa gattctgcag gcccgtgaag agggcaaaga aattcctgaa      600
ggatggggag tcgatgaaaa cggagaagca gtaactgatc ctgacaaggt cgtctcactt      660
```

```
tcaacattcg ggggcccgaa aggctatgga ctatcgattg tagtggatgt gttttccgga    720
ttgctggcgg gcgcggcttt tggccctcat attgccaaaa tgtacaacgg ccttgatcaa    780
aaaagaaagc tggggcatta cgtttgcgcg atcaatccat ccttttttac tgactgggat    840
acgttttag agcagatgga tgccatgatt gatgaactgc agcaatcacc gccggctgtt    900
ggattcgaaa gagtgtatgt gcccggcgag atcgagcagc tgcatgaaga agaaataag    960
aaaaacggaa tttctatcgc ccggagcgtg tatgaattct aaaaagcag gtga          1014
```

<210> SEQ ID NO 62
<211> LENGTH: 1020
<212> TYPE: DNA
<213> ORGANISM: Bacillus subtilis

<400> SEQUENCE: 62

```
atgaaagcgg ttcaagtgcg aaaagcgtat gatctggtga cagcggaggt gaagaagcca     60
gttcttcaa aggatgatga agtgctcgtg aaagtcaagc gagtcggcat ttgcggttca    120
gacatgcaca tttatcatgg aacgaatccg ctcgctaccc tcccgagagt catcggacac    180
gaggtaacgg acaagtgga ggcagttggt gcgaatgtac agagcctaaa acccggtgat    240
catgtggtga ttgagccgat ttcttattgc ggatcgtgct atgcctgccg caaagggcgg    300
ccgaatgttt gcgccaagct ttctgtattt ggcgtacatg aggacggagg catgcgggaa    360
tatattgtgc ttccggaaag acagcttcac gcggtctcaa aggacttgcc ttgggaggaa    420
gcagtcatgg ccgagcctta tacgataggc gcccaggcag tgtggagagg ccaggtggaa    480
aaaggtgata ccgtcctgat ccagggagcg gggcccatcg ggatctgtgt gttaaaaatg    540
gcaaaactgg cgggcgctgc tgtcatgatg actgacttga caacgagcg gctggcattt    600
gcgaaagaaa acgcgccga tgctgttgta aatgtccaag cagaacatgt tgccgagcgg    660
gtccttgaat ggactgggaa tgaaggagca aacgtggtca ttgatgctgt ttgcctgccg    720
gagacttttg cactttcaat tgaggctgtg tcaccggcgg acatgtggt tgtgcttgga    780
tttgatgaaa gagcggctca gatttctcag ctgccaatta caaaaaaaga agtcacgata    840
accggatccc gattgcagac caatcagttt ccaaaagtgg tagagctttt gaatggaggc    900
cggttaatgc ataacgggct ggtgacccat acattttcag ttgatgacgt tcatcatgca    960
tttcagttta ttaaggagca tccagatcag gtgcggaaag ccgtcatcac gtttgattaa   1020
```

<210> SEQ ID NO 63
<211> LENGTH: 1080
<212> TYPE: DNA
<213> ORGANISM: Bacillus subtilis

<400> SEQUENCE: 63

```
atgaatatga cattccgatg gtatggacga ggcaacgata cagtcacact tgaatacgtg     60
aagcaaattc ccggtgtcaa aggcatcgtt tgggctctcc atcaaaagcc cgtcggcgac    120
gtgtgggaaa aagaagaaat cagagccgaa actgaatata ttcaatccta tggttttcat    180
gctgaagttg tagaaagcgt gaatgttcac gaagcgatta acttgggaa cgaagaacgc    240
ggccggtata ttgaaaacta caagcaaacg atccgcaacc ttgccggatt tggcgtgaaa    300
gtgatctgct ataatttttat gccggttttt gattggacac gcacggacat gttccggccg    360
ctagaagatg gatcgaccgc tctgtttttt gaaaaggcca aggtggaaag ccttgatcct    420
caagagctga ttcggacggt ggaggaagca tccgacatga cactgccggg gtgggagccc    480
```

-continued

```
gaaaaattgg ctcggatcaa agagcttttt gctgcctaca gaacggtcga tgaagaaaag      540
ctatgggaca atttatcatt cttttttgcag gaaattcttc ctgttgctga ggcctatggt     600
gttcaaatgg ccattcatcc ggatgacccg ccgtggccga ttttcggact gccgcgcatt     660
atcacaggag aggcaagcta taagaaactg cgggcgatat cagattcacc gtctaattgt     720 atcaccettt gtacaggttc aatgggagcc aatcccgcta cgacatggt ggagatcgct      780 aaaacgtatg ccggcatcgc tccattttca catattcgca atgtgaaaat ttatgagaat     840 ggcgattta ttgaaacatc tcatttaaca aaggatggtt cgatcaacat tcaaggcgtg     900
atggaagaac tgcataagca ggattacgaa ggatatgtca gaccggatca tgggcgccat    960
ctttggggcg agcaatgccg cccgggatat ggcttatacg atcgggcact ggcatcatg     1020 tatttgaacg ggctgtggga cgcttatgaa gcaatggcaa aaaagaggt gggcatatga   1080
```

<210> SEQ ID NO 64
<211> LENGTH: 837
<212> TYPE: DNA
<213> ORGANISM: Bacillus subtilis

<400> SEQUENCE: 64

```
atgatcccgc tgcatgagaa cctggctggt aaaacggctg tcatcactgg cggcagcggc      60
gtgctttgct ctgcgatggc ccgggagcta gcccgtcatg gcatgaaggt ggcgattttg    120
aatcggacgg ctgaaaaagg ccaagcggtc gtgaaggaga taacggcgg tggcggcaca    180 gcgtgcgctg ttgctgcgga tgtgctgac aggatgtcac tggagcgggc aaaggaagac     240
atccttggcc aatttggcgc tgttgatctg ttaattaacg gggctggcgg caatcatcct    300
gacgcgataa ccgatgtgga gacatatgaa gaagcggag aaggccaatc cttttttgat    360
atggatgaga gggctttct aactgtattc tccaccaact tcaccggtgc gtttctggcc    420
tcgcaagtgt ttggtaaaga actgctgaag gcggattcac ccgcgatcat caacctttct    480
tccatgagtg cttattcacc tatgacgaag gttccggcat acagtgctgc gaaagcatcc    540
atcaataatt ttacgatgtg gatggctgtt cattttgccg aaaccgggct gcgggtcaat    600
gcgattgccc aggcttcttt tctgacaaaa caaaatcatg atctgctgat caaccaagac    660
ggaacgttca ccagccgatc tcacaaaatt attgcgggaa caccgatgaa gcgcttcgga    720
aaaccggagg atttgctcgg tacgctcctt tggctggcgg atgaatccta ttccggtttt    780
gtcactggga tcaccgttcc tgtcgatgga ggattatgg cttattcagg tgtgtaa        837
```

<210> SEQ ID NO 65
<211> LENGTH: 1269
<212> TYPE: DNA
<213> ORGANISM: Bacillus subtilis

<400> SEQUENCE: 65

```
atgttttcaa aagataagct tcccgttatc cttttttgt tcctggcagg ggtgattaat       60
tacctggatc gctcggcgct ttccattgca gctccttta ttcaggatga tctcacattg     120
tctgccacac aaatgggctt gattttcagc agttttttcga taggttatgc cattttaat    180 tttcttgggg gcgtggcatc cgaccgctat ggggcaaagc tgaccttgtt tgtcgcgatg    240 gttgttttggt cgctgtttag cggagcagtc gccctcgctt ttggctttgt cagcctgctg    300
attatacgca ttctcttcgg aatgggagaa ggccgctttt cggcgaccat caacaagatg     360
gtgaacaact ggttcccgcc gacccagcgg gcgtccgtta tcggtgtaac caacagcggc    420 acgccctcg ggggagccat ttccggcccg atagtcggca tgatcgcagt ggcgttcagc    480
```

```
tggaaggtat ccttcgttct cattatgatt attggattga tatgggcagt gctctggttc    540
aagtttgtca agaaaagcc gcaagagacg atcaaggaag caccggcaat aaaagcagaa    600
acgtctcccg gagaaaaaat tccgctcacc ttttacctga agcaaaaaac agtcctgttc    660
acggcgttcg cttttttcgc ttacaactac atcctcttct tcttttttgac atggtttccg    720 agctatcttg tcgacgagcg gggattaagt gttgaatcga tgagtgtcat cacggtcata    780
ccgtggattt taggatttat cgggctggct gcgggggggat tgtttctga ctatgtgtac    840 aaaaaaacgg cccgaaaagg tgtgctgttc tcgcgcaagg ttgtgcttgt cacgtgtttg    900
ttttcatcag ctgtcctgat tggttttgcc gggcttgtgg caacgactgc ggggggctgtc    960 actcttgtcg ctctgtcagt gttctttctt tatttgaccg gtgctatcta ttgggctgtc   1020
attcaagatg tggttgatca aaacaatgtc ggttctgttg gcggcttcat gcatttcctc   1080
gccaacacgg caggaattat cggcccggct ttaaccggat ttattgttga ccaaacaggc   1140
acgttttctg gagcattttt gcttgccggt gggctggctg tcttcgcttc acttgctgtg   1200
attcgttttg tccgtccaat cattggtaag ccagcgggaa cagaagctga gaatcctgtg   1260
tcttattaa                                                            1269

<210> SEQ ID NO 66
<211> LENGTH: 705
<212> TYPE: DNA
<213> ORGANISM: Bacillus subtilis

<400> SEQUENCE: 66
gtgcgcatcg ggggttttgg gacaggacgt atcgccgcgg gcattgattt cagcttgatc     60
cgcaaacacc ctaaaatctt ttgggggatac agcgatatta cgttttttaca tactgccatt    120 catcaaaaca caggtcttgt cactttccat ggcccgatgc tcagcacgga tattggcctt    180
gacgacgttc acccgctgac aaaagcgtca tataagcagc tcttccagga gacggaattc    240
acctatacag aagagctttc tccgctgacc gagcttgttc ctggaaaagc ggaaggcgag    300
cttgtcgggg gaaatctgtc tttgctgacg tctacactgg gcacgccatt tgaaattgat    360
acgagaggaa agcttctgtt tattgaagat attgacgagg agccttatca aatcgaccgg    420
atgctgaatc agctgaaaat ggggggggaag ctgacgacg cggcgggaat tctagtttgt    480
gattttcaca attgtgtccc ggtgaagcga gagaagtctc tctcgcttga gcaggtgctg    540
gaagactata ttatttctgc gggcaggcct gctctgagag gatttaaaat cggccactgc    600
tcgccaagta ttgccgttcc gatcggtgcg aaagctgcta tgaatacagc agaaaaaaca    660
gccgtaatag aggcgggcgt ttcagaaggg gcgctgaaga catga                    705

<210> SEQ ID NO 67
<211> LENGTH: 1101
<212> TYPE: DNA
<213> ORGANISM: Bacillus subtilis

<400> SEQUENCE: 67
atgaaaatca ttcgaatcga aacaagccga atcgctgtcc cgctgacaaa gccgtttaaa     60
accgcacttc gcactgtgta tacggctgaa tcagtcatag taaggattac ttatgacagc    120
ggtgcagtcg gatggggaga agcaccccg acgttagtga ttacaggaga cagcatggat    180
agcattgaaa gtgccatcca ccatgtgttg aagccggcat tgcttggaaa aagcctggcg    240
ggctatgagg ccattctgca cgacatccag catcttctta caggaaatat gagcgcgaag    300
```

-continued

| | |
|---|---|
| gctgctgtag aaatggctct atacgacggc tgggcgcaga tgtgcgggct gccgcttat | 360 |
| caaatgcttg gcggatatcg agatacgctg gaaacagatt atactgtcag tgtcaactca | 420 |
| cctgaagaga tggcagctga tgccgagaat tatctcaaac aaggctttca aacgctgaaa | 480 |
| ataaaggtcg gaaaagatga tattgcaaca gatatcgccc gtatccagga atcagaaaa | 540 |
| cgtgtcggat cagctgtgaa actgcgttta gacgctaatc aggggtggag ccgaaggaa | 600 |
| gcggtaactg ccattcggaa aatggaggat gcgggcctag gcattgagct tgtcgagcag | 660 |
| cctgtccata aagatgatct cgctgggctt aaaaaggtga cagatgcaac agatacgccg | 720 |
| attatggctg atgaaagtgt ttttacaccg cgccaggcgt tcgaagttct gcaaacccgg | 780 |
| agcgcagact tgatcaatat taaattgatg aaagcgggcg gcatcagcgg agcagagaaa | 840 |
| attaatgcca tggcggaggc ctgcggggtg gagtgtatgg tcggcagcat gatcgaaacg | 900 |
| aagctgggca ttacgccgc ggcgcatttt gcggcaagca agagaaacat cacacgcttt | 960 |
| gattttgacg cgccgctgat gctgaaaaca gatgtattca atggcggcat aacatatagc | 1020 |
| ggcagcacga tttcgatgcc tggcaaaccg ggcctcggaa tcatcggggc tgcgcttttg | 1080 |
| aaaggggaaa aagagcaatg a | 1101 |

<210> SEQ ID NO 68
<211> LENGTH: 891
<212> TYPE: DNA
<213> ORGANISM: Bacillus subtilis

<400> SEQUENCE: 68

| | |
|---|---|
| atgatgcaca ctgtcatatc agcagtggcc aacatctgga cagcgcctga ttcacctcgt | 60 |
| ccgtctgatc aattcatgct tcaaccgact gtaatgatca gagactggct ggagcgcatg | 120 |
| acgtatgatg aacggcttgg attatgtaca gacaatgtaa tccaaactca ggttctcttt | 180 |
| ggcgaaaagg tacttgtgac ggcggaacag ggggaatggg tttctgtgat cgtgcctagc | 240 |
| cagccatccc gaaaggatcc gcgcggatac ccgggctgga tgaaaaagta ccagctggaa | 300 |
| aaaacaaagc ccatccatac acaacacgat gtgatgatca gcaaacctgc tgccttttg | 360 |
| tacagaagca atggggaaaa ggagatcgaa ttaagctttt tgacagttct gcccccttatt | 420 |
| gcaaaagaaa acggatattt taaggtttcg accgtttttg gggaaaggtt tgtgaggcaa | 480 |
| agtgatgcag tgcctgtcag ccaacagaaa gggactgctg aagacatcat tcaaacgggt | 540 |
| gcgtttttc ttggccttcc ctacctgtgg ggagggatca gcgggtttgg gtttgattgc | 600 |
| tccggattta tgtacagtat atttaaggcg aatggataca gcatcccccg tgatgcggga | 660 |
| gatcaggcta aggcagggaa ggttgtcccg cttgatgata tgaaagccgg tgatctgctg | 720 |
| ttttttgctt atgaggaagg aaaaggagcg attcatcacg tcggtctgta tgtaggcggc | 780 |
| gggaaaatgc ttcattctcc aaagacaggg aagtcaatcg aaatcctcac attaacagag | 840 |
| acaatctatg aaaaagaatt atgtgcggtg cgccgctgtt tttcagaata a | 891 |

<210> SEQ ID NO 69
<211> LENGTH: 984
<212> TYPE: DNA
<213> ORGANISM: Bacillus subtilis

<400> SEQUENCE: 69

| | |
|---|---|
| atgaggcgac tgcctttgtt agaggtcagc cagctgaaaa tgcattttga cgcagggaaa | 60 |
| aagcggacag tcaaagctgt cgacgggtc acctttcaga ttcgtgaagg agaaacgttc | 120 |
| gggctagtcg gggaatcagg gtgcgggaaa tcaaccttgg ggagagtgct gatgcgcctt | 180 |

```
tatcagccga cagaaggaag cgtgacatac cgcggcacaa atcttcatgc actaagtgaa      240
aaagagcagt tgccttcaa ccgcaaactg cagatgattt tcaggaccc  ttatgcttca      300 cttaacccgc gcatgaccgt tcgagaaatt attttggagc cgatggagat tcataatctc     360
tacaataccc ataaagcacg gctttccgtc gtggacgagc tgcttgaggc agttgggctt     420
caccccgatt ttggcagccg ttatccgcat gaattcagcg gcgggcaaag gcagagaatc     480
gggattgcga gagcactgtc gctgaatcct gaatttatcg tggcggacga accgatttct     540
gcacttgatg tctctgttca agcgcaggtg gtcaacctgc tgaagcggct tcaaaaagag     600
aaagggctta cgttttta tt cattgcccat gatctttcga tggtgaagca tatcagtgac     660
aggatcggtg ttatgtactt aggacacatg atggaaatta cagagagcgg caccttgtat     720
cgtgaaccgc tccatcccta tacaaaggcg cttttgtcct cgattccgat tccagatcct     780
gaattggagg acaagcgtga gcgtattctc ttgaaagggg agctgccgag cccggtcaat     840
ccgccaagcg gctgcgtgtt tcgtacccgc tgtccggagc gatgcctgaa tgtggagaat     900
ctcgtcccca gcttcaagaa atcgaacccg gccgttttgt cgcttgccat ttgtatcgaa     960
atgctgaaac gaaggaaaaa gtaa                                             984

<210> SEQ ID NO 70
<211> LENGTH: 1416
<212> TYPE: DNA
<213> ORGANISM: Bacillus subtilis

<400> SEQUENCE: 70
ttgaaaaaca aatggtataa accgaaacgg cattggaagg agatcgagtt atggaaggac       60
gttccggaag agaaatggaa cgattggctt tggcagctga cacacactgt aagaacgtta      120
gatgatttaa agaaagtcat taatctgacc gaggatgaag aggaaggcgt cagaatttct      180
accaaaacga tcccccttaaa tattacacct tactatgctt ctttaatgga ccccgacaat     240
ccgagatgcc cggtacgcat gcagtctgtg ccgctttctg aagaaatgca caaaacaaaa     300
tacgatctgg aagacccgct tcatgaggat gaagattcac cggtacccgg tctgacacac     360
cgctatcccg accgtgtgct gttcttgtc acgaatcaat gttccatgta ctgccgctac     420
tgcacaagaa ggcgcttttc cggacaaatc ggaatgggcg tccccaaaaa acagcttgat     480
gctgcaattg cttatatccg ggaaacaccc gaaatccgcg attgtttaat tcaggcggt      540 gatgggctgc tcatcaacga ccaaattta gaatatattt taaaagagct gcgcagcatt     600
ccgcatctgg aagtcatcag aatcggaaca agagctcccg tcgtctttcc gcagcgcatt     660
accgatcatc tgtgcgagat attgaaaaaa tatcatccgg tctggctgaa cacccatttt     720
aacacaagca tcgaaatgac agaagaatcc gttgaggcat gtgaaaagct ggtgaacgcg     780
ggagtgccgg tcgaaatca ggctgtcgta ttagcaggta ttaatgattc ggttccaatt     840
atgaaaaagc tcatgcatga cttggtaaaa atcagagtcc gtccttatta tatttaccaa     900
tgtgatctgt cagaaggaat agggcatttc agagctcctg tttccaaagg tttggagatc     960
attgaagggc tgagaggtca tacctcaggc tatgcggttc ctacctttgt cgttgacgca    1020
ccaggcggag gaggtaaaat cgccctgcag ccaaactatg tcctgtcaca aagtcctgac    1080
aaagtgatct taagaaattt tgaaggtgtg attacgtcat atccggaacc agagaattat    1140
atccccaatc aggcagacgc ctattttgag tccgtttttcc ctgaaaccgc tgacaaaaag    1200
gagccgatcg ggctgagtgc cattttttgct gacaaagaag tttcgtttac acctgaaaat    1260
```

```
gtagacagaa tcaaaaggag agaggcatac atcgcaaatc cggagcatga acattaaaa    1320 gatcggcgtg agaaaagaga tcagctcaaa gaaagaaat ttttggcgca gcagaaaaaa    1380
cagaaagaga ctgaatgcgg agggattct tcatga                              1416
```

<210> SEQ ID NO 71
<211> LENGTH: 828
<212> TYPE: DNA
<213> ORGANISM: Bacillus subtilis

<400> SEQUENCE: 71

```
atgctcaagt caataaagag tagcggtgtc acagcagttt tggaccatga cggctttaat    60
aaacgaatca gagtggttcg ttatgacgga gccattgaga aggccctgcc ggatatcgtg   120
gcagcggcaa aagaagagaa tgcagaaaaa atcattgtct atgcgaagca gcatgatgag   180
ccgatccttg ccaaacaatt atttgcgccg gagggctatc taagggcta ttatctcggc    240 cattcggctt gtgtcatggt acgttacctt tcagaaagcc ggagacaaac agattcttat   300
acagaggaac aggagatcat cgaagccata tatcgcacag cgccccgtct tcgcaacgac   360
agtacacccg tttttacgat gagaaaagca gaaacaaacg acatgtacca gctatcgatg   420
ctgtataaaa aagtattccg cacgtaccca accccggtat ttgaccccgc ttatattgaa   480
aagacgatga atgcaaatac ggtgtattat atcatgcttg atcatgaccg cctgatcagc   540
gcagcaagcg cagaaatcaa tccagagctt gggcatgcag aaataaccga ttgcgctgtg   600
ctgccggaat atcgcggcca ttcgttaaca agcttttaa tcgaggcgtt agaaaaagaa    660
atggctggag aggatatcgt tcatgtgttt tctctcgccc gtgcttcgtc ttttgggatg   720
aatgctgtgt tgtaccattc aggttatcag tatggcggaa ggctgatcaa taattgcttt   780
atagccgaag gccttgaaaa catgaatatt tggtgcaagc aactgtaa                828
```

<210> SEQ ID NO 72
<211> LENGTH: 654
<212> TYPE: DNA
<213> ORGANISM: Bacillus subtilis

<400> SEQUENCE: 72

```
atgggcttgg gagtagcaga aagagaacag attgcaaaac gcgctgctac tgaaattaag    60
cagggcatga ttgtgaatct cggtatcggt atcccttcct tggtaccgaa cttttttgaag   120 cctgacatgc aggtcatgtt tcaagcggaa acggtgtcc ttggcattgg agaaagtccc    180
gaaaagggag aagaggatgc gcatttatgc aacgccgcgg gatatcctgt ccgcgctgta   240 aaagggctt cttattttga tacaaccatg tcttttgcga tgatcagaaa aggcaaaatt    300
gacattacga ttttaggcgc cctgcaggtg agccaatcag gagatttggc aaattggctt   360
gttccgggaa aaaggtgcc tggtatgggc ggggcgatgg agcttgccca aaagcgaaa    420 aagtggttg tcgtcatgag tcatacagat caaagggaa ggcctaaatt aacagaaaga   480
tgtacgctgc cattaactgc tgcaggctgt gtagattga ttattaccga aaagcggtt    540 cttgaggtcg atagccatca cttcatttta aaagagctga tgaatggctc gacaatcgat    600
gaggtgacga ggctgacaga agctgaaatc aaaatagata tgccttttc ttaa           654
```

<210> SEQ ID NO 73
<211> LENGTH: 690
<212> TYPE: DNA
<213> ORGANISM: Bacillus subtilis

<400> SEQUENCE: 73

```
atggcgccat ttcaaaaagc aatcagcatt gacacagcaa ttgcagatgt tcgggatgga    60
tcggttctga tgtttggcgg ttttgggggga gtcgggtcgc ctccttcatt gattgaagcg   120
atattggaca gcggtgtaac ggatttgact gtgatttgca atgacgccgg tttcccggat   180
atcggaatcg gcccgcttat tgttaatcaa cgggtcaaaa ccctgatcgc ctcgcatatc   240
ggttccaatc cagtagccgg aaaacagatg acagagggga cgttagaggt tcaattttca   300
cctcagggaa cgcttgcgga acggattcgc gccggcggag cggggcttgg cggtatttta   360
accgacgtgg gcattgataa tcaaatggtt tgcgaaaaaa aggacatcgt aacagtggcg   420
ggaaaacgat acttgattga agaggcgctg actgctgatt ttgctttcat caatgcttac   480
attgcagatg aattcggcaa tctaacgtat gacaaaaccg cgcgcaatat gaacccgctt   540
atggcaatgg ccgccaggag aacctttgcc gaagctgagc gtatcgttcc gatgggggag   600
atttctgaag aaatgattgt cacaccgggg gttttttgttg aggggggttgt acgaagcgag   660
ggagtgaagt ggaaatgggc ttgggagtag                                    690

<210> SEQ ID NO 74
<211> LENGTH: 1335
<212> TYPE: DNA
<213> ORGANISM: Bacillus subtilis

<400> SEQUENCE: 74
atgagcagtt atttgattaa gccagagctt agctcggcct atccggttgt cagttatgcg    60
aagggttcat atgtttatga tcagaccgga aaaaaatatc tcgacggctc gtcaggtgcg   120
gtgacatgta atatcggcca cggagttcgt gatgtgactg agaagctgaa agaacagctt   180
gatcaggtgt cttttgctta ccgctcacag tttacgagtg agcccgccga gcaattagcc   240
gctctcttgg cacaggagct gcccggagat gtgaattggt cttttttttgt caacagcgga   300
tcagaagcga tagaaacagc tatgaaaatc gccattcagt attggcagga aaaaaagcaa   360
acacaaaaat ccatcttttt gtctcgatgg agcagttacc acggaataac tttgggagcg   420
cttttcattgt ctggttttta tgaaaggaga taccggttca cccatctcat tgagcggtat   480
ccagctatct cagctccaca tatttatcgg ctgaatcacg agacggaaga agactttgtt   540
cagactgcag ctgatgaact ggacaccatg attaaagaa tcggaagcca attcatcgcc   600
ggctttgtgg ctgagcctat tattggtgct gcaggagcag cgattactcc gcctccggga   660
tattatgaga gattaagtga ggtatgccgc acacacgatg tgcttttttat tgcagatgaa   720
gtgatgacgg ggcttgggag aacaggaagg atgctcgcga cagagcattg ggataccgta   780
cctgatattg ctgtactggg gaagggactc ggtgcgggt atgcacctat tgctgctgcc   840
gtcgtatctg attctattat tgaaaccata aacaagggt caggtgtgat tatgagcggt   900
cacacatata gtgcacatcc ctattcagcc aaagctgctc ttgaagtttt tgcgatatgtg   960
ttaaagcacg gcttgatcaa acaatcagaa aaaaagggcg ctgtgctgaa gaagaagctt  1020
gatgaggcg catctcaaag cggcattata ggtgaggtgc gcggaaaagg actgctatta  1080
ggcattgaat tgtgtggcaga ccaaaaaacg aagaaagtgt tccgccaga gcaggcgata  1140
acccagctta ttgtcagcga ggcgaaaaaa cgcgggctga ttgtttatcc ttccaaagct  1200
ggaatagaca gtggagaagg agatgctgtc attattgctc ctccttttac tatttcagac  1260
ggtgaaatgg aagagcttat ctctatttttt tcagaaacag ttgcagcggt cgaaaaaaac  1320
ttaaaaaagg attga                                                   1335
```

-continued

<210> SEQ ID NO 75
<211> LENGTH: 912
<212> TYPE: DNA
<213> ORGANISM: Bacillus subtilis

<400> SEQUENCE: 75

| | | | | | |
|---|---|---|---|---|---|
| gtgatcacaa | gagatttttt | cttattttta | tccaaaagcg | gctttctcaa | taaaatggcg | 60 |
| aggaactggg | gaagtcgggt | agcagcgggt | aaaattatcg | gcgggaatga | ctttaacagt | 120 |
| tcaatcccga | ccattcgaca | gcttaacagc | caaggcttgt | cagttactgt | cgatcattta | 180 |
| ggcgagtttg | tgaacagcgc | cgaggtcgca | cgggagcgta | cggaagagtg | cattcaaacc | 240 |
| attgcgacca | tcgcggatca | ggagctgaac | tcacacgttt | cttttaaaaat | gacgtcttta | 300 |
| ggtttggata | tagatatgga | tttggtgtat | gaaaatatga | caaaaatcct | tcagacggcc | 360 |
| gagaaacata | aaatcatggt | caccattgac | atggaggacg | aagtcagatg | ccagaaaacg | 420 |
| cttgatattt | tcaaagattt | cagaaagaaa | tacgagcatg | tgagcacagt | gctgcaagcc | 480 |
| tatctgtacc | ggacgaaaaa | agacattgac | gatttggatt | ctttaaaccc | gttccttcgc | 540 |
| cttgtaaaag | gagcttataa | agaatcagaa | aaagtagctt | tcccggagaa | aagcgatgtc | 600 |
| gatgaaaatt | acaaaaaaat | catccgaaag | cagctcttaa | acggtcacta | tacagcgatt | 660 |
| gccacacatg | acgacaaaat | gatcgacttt | acaaagcagc | ttgccaagga | acatggcatt | 720 |
| gccaatgaca | agtttgaatt | tcagatgctg | tacggcatgc | ggtcgcaaac | ccagctcagc | 780 |
| ctcgtaaaag | aaggttataa | catgagagtc | tacctgccat | acggcgagga | ttggtacggc | 840 |
| tactttatga | gacgccttgc | agaacgtccg | tcaaacattg | catttgcttt | caaggaatg | 900 |
| acaaagaagt | aa | | | | | 912 |

<210> SEQ ID NO 76
<211> LENGTH: 1548
<212> TYPE: DNA
<213> ORGANISM: Bacillus subtilis

<400> SEQUENCE: 76

| | | | | | |
|---|---|---|---|---|---|
| atgacaacac | cttacaaaca | cgagccattc | acaaatttcc | aagatcaaaa | ctacgtggaa | 60 |
| gcgtttaaaa | aagcgcttgc | gacagtaagc | gaatatttag | gaaaagacta | tccgcttgtc | 120 |
| attaacggcg | agagagtgga | aacggaagcg | aaaatcgttt | caatcaaccc | agctgataaa | 180 |
| gaagaagtcg | tcggccgagt | gtcaaaagcg | tctcaagagc | acgctgagca | agcgattcaa | 240 |
| gcggctgcaa | agcatttga | agagtggaga | tacacgtctc | ctgaagagag | agcggctgtc | 300 |
| ctgttccgcg | ctgctgccaa | agtccgcaga | agaaaacatg | aattctcagc | tttgcttgtg | 360 |
| aaagaagcag | gaaagccttg | gaacgaggcg | gatgccgata | cggctgaagc | gattgacttc | 420 |
| atggagtatt | atgcacgcca | aatgatcgaa | ctggcaaaag | gcaaaccggt | caacagccgt | 480 |
| gaaggcgaga | aaaaccaata | tgtatacacg | ccgactggag | tgacagtcgt | tatcccgcct | 540 |
| tggaacttct | tgtttgcgat | catggcaggc | acaacagtgg | cgccgatcgt | tactggaaac | 600 |
| acagtggttc | tgaaacctgc | gagtgctaca | cctgttattg | cagcaaaatt | tgttgaggtg | 660 |
| cttgaagagt | ccggattgcc | aaaaggcgta | gtcaactttg | ttccgggaag | cggatcggaa | 720 |
| gtaggcgact | atcttgttga | ccatccgaaa | acaagcctta | tcacatttac | gggatcaaga | 780 |
| gaagttggta | cgagaatttt | cgaacgcgcg | gcgaaggttc | agccgggcca | gcagcattta | 840 |
| aagcgtgtca | tcgctgaaat | gggcggtaaa | gatacggttg | ttgttgatga | ggatgcggac | 900 |
| attgaattag | cggctcaatc | gatctttact | tcagcattcg | gctttgcggg | acaaaaatgc | 960 |

-continued

```
tctgcaggtt cacgtgcagt agttcatgaa aaagtgtatg atcaagtatt agagcgtgtc    1020
attgaaatta cggaatcaaa agtaacagct aaacctgaca gtgcagatgt ttatatggga    1080
cctgtcattg accaaggttc ttatgataaa attatgagct atattgagat cggaaaacag    1140
gaagggcgtt tagtaagcgg cggtactggt gatgattcga aaggatactt catcaaaccg    1200
acgatcttcg ctgaccttga tccgaaagca agactcatgc aggaagaaat tttcggacct    1260
gtcgttgcat tttgtaaagt gtcagacttt gatgaagctt tagaagtggc aaacaatact    1320
gaatatggtt tgacaggcgc ggttatcaca acaaccgca agcacatcga gcgtgcgaaa    1380
caggaattcc atgtcggaaa cctatacttc aaccgcaact gtacaggtgc atcgtcggc    1440
taccatccgt ttggcggctt caaaatgtcg ggaacggatt caaaagcagg cgggccggat    1500
tacttggctc tgcatatgca agcaaaaaca atcagtgaaa tgttctaa                1548

<210> SEQ ID NO 77
<211> LENGTH: 1398
<212> TYPE: DNA
<213> ORGANISM: Bacillus subtilis

<400> SEQUENCE: 77
atggagtctt ttttcaatag tttgattaat attccaagtg atttcatctg gaaataccta     60
ttttatattt taatagggct tggattattt tttaccatac gttttggttt tatccaattc    120
cgttatttta ttgaaatgtt cagaatagta ggggagaagc cggaaggaaa taaggtgtt    180
tcatctatgc aggcattctt tatttcggcc gcatcccgag tcggcacagg gaatttgact    240
ggtgtagcct tagcaattgc gacaggcgga ccaggcgctg tattttggat gtgggtagtg    300
gctgcagtag gcatggcttc aagctttgtc gaaagtacat tagcacagct ttataaggta    360
agagacgggg aggatttccg cggagggccg gcctactata ttcaaaaggg tcttggtgcc    420
agatggcttg gcatcgtttt tgcaatctta attaccgtct cattcggctt gatttttaac    480
gctgttcaaa caaatacaat tgctggagca ttggatggcg cattccatgt aaataaaata    540
gttgtagcca tagttctggc ggttttaact gcgtttatca ttttcggcgg tttaaaacgt    600
gttgtcgctc tttcacagct aattgtgccg gttatggcag gcatttatat tcttatcgct    660
ttatttgttg tcatcacgaa tattacggct ttccctggcg ttatcgctac aattgttaaa    720
aatgctttag gttttgaaca agtcgtcggc ggcggaatag gcggcatcat cgttatcggt    780
gcgcaacgcg gacttttttc aaacgaagca ggaatgggga gcgcaccaaa cgcggctgcg    840
acggctcatg tatcccatcc ggcaaagcaa ggctttattc aaacattagg cgtatttttc    900
gatacattta tcatatgtac gtccacagca tttattattt tgctgtacag tgtaacgcca    960
aaaggcgacg gcatccaagt cacacaggct gctcttaacc atcacattgg aggctgggcg   1020
ccgactttca tcgcagtcgc aatgttcttg tttgcattca gttcagttgt cggcaactat   1080
tattatggcg agacaaacat tgaatttatt aaaacaagca aaacatggct gaacatttac   1140
cgtatcgctc ttattgctat ggttgtgtat ggatctttat caggcttcca aatcgtttgg   1200
gatatggcgg acctctttat gggtatcatg gcgctgatca acttaattgt gattgcgctg   1260
ctgtcaaacg ttgcttacaa agtgtataaa gattacgcga acagcgtaa gcaaggactt    1320
gatcctgtgt ttaaagcgaa aaacatccca gggctgaaaa acgctgaaac atgggaagat   1380
gagaaacaag aagcataa                                                 1398

<210> SEQ ID NO 78
```

<211> LENGTH: 675
<212> TYPE: DNA
<213> ORGANISM: Bacillus subtilis

<400> SEQUENCE: 78

```
atgaacacga ttgattggga attcatgata tcagcgttcc cgactttaat tcaggccctt      60
ccgatcacct tgtttatggc aatagcagct atgattttg ccattatcgg aggacttatt     120
ctcgcactca ttacaaaaaa caaaattcca gtgcttcatc agctgtcaaa gctgtatata     180
tcctttttcc gaggcgtgcc gacacttgta cagctgttct taatctatta cgggctgccg     240
cagctatttc cagagatgag caaaatgaca gctctcacag ctgccatcat cgggttaagc     300
ttaaaaaacg cagcttattt ggcagaaatc ttccgggccg ccctcaattc tgttgatgac     360
gggcagctgg aggcgtgcct gtctgtcggt atgacaaaat ttcaggcata cagacggatt     420
attttgccgc aagcgatccg aaatgcgatt ccggcaacgg caatacatt tatcgggctc     480
ctgaaagaaa cgtcactggc ctttacatta ggggtcatgg agatgttcgc caagggaag     540
atgtacgctt caggaaaccct caaatatttt gagacgtatt tggcggttgc gatcgtctat     600
tggttctta ccattatcta cagcattttg caggacttgt ttgaacgtgc catgagcaag     660
ccataccgga cttag                                                       675
```

<210> SEQ ID NO 79
<211> LENGTH: 795
<212> TYPE: DNA
<213> ORGANISM: Bacillus subtilis

<400> SEQUENCE: 79

```
atgaagatga aaaatggac agtgctggtc gttgctgcat tattagcggt gctctcagct      60
tgcggcaatg gaaacagcag cagtaaagag gatgacaatg tgcttcatgt cggtgcgaca     120
ggacaaagtt acccatttgc ttataaagaa acggaaagc tgacaggctt tgacgtggaa      180
gtgatggaag cagtcgctaa gaaaattgac atgaaactgg actggaagct gcttgaattc     240
agcgggctga tgggagagct tcaaacaggc aagcttgaca ccatttccaa ccaggtagct     300
gtgacagacg aacgtaagga acgtataac tttacgaaac catacgctta tgcgggaaca     360
cagattgtcg tcaaaaaaga caatacagac atcaaatcag tagacgattt aaaaggcaag     420
acagtcgcag ccgttctcgg ttcaaaccac gcgaaaaacc ttgaaagcaa agatcctgat     480
aaaaaaatca atatcaaaac gtacgaaaca caagagggta cgctgaagga tgttgcgtac     540
ggccgtgtag acgcttatgt caacagccga actgtattga tcgcgcaaat caagaagacc     600
ggtttgccat aaagcttgc aggagatccg attgtttacg aacaggttgc attcccattt     660
gccaaggacg atgcgcacga caagctccgc aaaaaagtca taaggcct agatgaattg     720
cgtaaagacg gaacactgaa aaaactctct gaaaatact ttaatgaaga tatcacagta     780
gaacagaagc attaa                                                      795
```

<210> SEQ ID NO 80
<211> LENGTH: 498
<212> TYPE: DNA
<213> ORGANISM: Bacillus subtilis

<400> SEQUENCE: 80

```
atgaagccac gataccgcct tgcagttgaa cgtgatgccg aacagcttct cgagctgaca      60
ttgcgggctt atgaaccgat tcgaaagctc ggcattcgtt ttgctgctgc tcatgcggat     120
ttggatttgg tgctgaaaaa tattcgggaa aatgcttgct acgtcatgga agaagacggg     180
```

```
cggatcatcg cgaccatcac cttgagaatg ccttggggaa aacagccggg accgtatggc    240
gttccgcata tctggtggtt tgctgtggac cccgacaccg gtaaaaaagg aatcggtaca    300
aagctgcttc aatggctgga ggaaacaatc cttcgcgata cgttaaaggt tccgtttgtt    360
tcactcggaa cagcggataa gcatccgtgg ctgattgaga tgtacgaacg aaaaggatat    420
gtccgctcag gtgaacaaga ccttggaaaa gggcatatca cagtctatat gaaaaaacaa    480
ttgggacatg atctataa                                                 498

<210> SEQ ID NO 81
<211> LENGTH: 1326
<212> TYPE: DNA
<213> ORGANISM: Bacillus subtilis

<400> SEQUENCE: 81
atgacaagca aaaagaaaca aatcaaatta ggggtatttt tagcaggtac aggccatcat     60
gttgcgtctt ggcggcaccc ggacgcgccg tcagatgcga gcatgaattt ggattatttt    120
aaagagcttg cgaaaacagc ggagcgaggc aagctggata tgctgttttt agcggacagc    180
ctttcaattg acagcaaatc acatccaaat gtattaacaa ggtttgagcc attcaccctg    240
ctctctgctt tggcgcaggt cacatcaaaa atcggactga cagcaacagc ctccactaca    300
tacagcgagc cattccatat tgccagacag tttgcgtcat tggatcatct gtccaatggc    360
cgtgccggat ggaacgtcgt cacttcatct attgaatcaa cagcgctgaa tttcagcggt    420
gaaaagcacc ttgaacacca tttgcgctat cagcgggcag aggaatttgt cgagattgta    480
aagggctttt gggattcatg ggaagaggac gcctttatcc gtaataaaga aacgggtgaa    540
ttctttgaca aagaaaaaat gcatgagctg aaccacaaag gagaatattt ctcggttcgc    600
ggacctctaa acgtttcaag aacccccgcag ggccagccgg tcattatcca ggcaggatca    660
tcaggagacg gaaaagcgct ggctgccaaa acagccgaag tgatcttcac agcacaaaac    720
cacctggaat cagctcaaga attttatcaa tccattaaag aacaggctgc ggaattcgga    780
cgtgatccag aaaaaattgc cattatgccg ggtattttcc caatcattgc cgatacagaa    840
gaagcagcgc aagccaaata caaggagctc caagatctga ttatcccatc tgtcggtctg    900
caaattctcc aaaattactt aggcggaatt gatttgtcgg catatccgct tgatgggccg    960
ctgccgaagc ttgacgccga agcttccaat gcggtgaaga gccgcttcaa gcttgttcag   1020
gagatggctg aacgtgacaa tatgacgata cgagagcttt acaaatacgt tgcaggctcc   1080
agaggccacc atatcttcgt cggcacgccg gagcagctcg ccgacaagat gcaggaatgg   1140
gtggatacga aagcgtgtga cgggtttaac atcatgcctc cgcttcttcc agaaggaatt   1200
gaagtgtttg ttgatcaagt ggttccgatt ttacaggagc gcggcgtgtt cagaaaagaa   1260
tatgaaggca caacattacg agagcacttc ggtttggaaa agccggtaaa ccgctatgca   1320
aagtaa                                                             1326
```

NATURAL PROMOTERS FOR GENE EXPRESSION AND METABOLIC MONITORING IN BACILLUS SPECIES

FIELD OF THE INVENTION

This application claims the benefit of U.S. Provisional Application No. 60/214,967, filed Jun. 29, 2000 and of U.S. Provisional Application No. 60/268,320, filed Feb. 13, 2001.

This invention is in the field of bacterial gene expression and fermentation monitoring. More specifically, the invention relates to the use of promoter regions isolated from a Bacillus sp. for regulated gene expression and process control monitoring of fermentation cultures.

BACKGROUND INFORMATION

The Bacillus bacteria are useful production hosts for a variety of biological materials including enzymes, antibiotics and other pharmaceutically active products. The use of Bacillus species for production of biomaterials is particularly advantageous as compared with other microbial production hosts, particularly gram negative organisms. For example, the most common gram negative organism used in industrial microbiology, *E. coli*, suffers from the presence of endotoxins which, being pathogenic in man, are undesirable products. Additionally, gram negative hosts often produce proteins in inactive or insoluble forms which necessitate expensive reactivation and purification schemes. In contrast, Bacillus has a highly develop secretory system for the expression and transport of active proteins to the growth medium, thereby facilitating purification and eliminating costly reactivation procedures. Thus Bacillus is a production host of choice for many industrial applications. Methods to enhance gene expression or monitor culture health and biomass production for these organisms are desirable.

The Bacillus sp. and particularly *Bacillus subtilis* is well-known for its stationary metabolism (Stragier, P. and Losick, R. 1996. *Annu. Rev. Genet.* 30:297–341, Lazazzera, B. A. 2000. *Curr. Opin. Microbiol.*3:177–182, Msadek, T. 1999. *Trends Microbiol.* 7:201–207). A wide variety of genes, such as those involved in catabolism, amino acid biosynthesis, antibiotic production, cell to cell communication, competence, and sporulation, are induced at stationary phase. *Bacillus subtilis* is also a facultative bacterium capable of growing in the presence or absence of oxygen. In the absence of oxygen, *Bacillus subtilis* uses nitrate or nitrite as the alternative electron acceptor or grows in the presence of pyruvate (Nakano et al., 1998. *Annu. Rev. Microbiol.* 52:165–190). It has been shown that promoters that control the expression of genes involved in nitrate and nitrite respiration are under the control of the two-component signal transduction system ResDE (Sun et al., 1996. *J. Bacteriol.* 178:1374–1385).

In general, prokaryotic promoters can play an important role in biotechnology particularly in expressing those genes whose products can be made in their active forms and in large quantities in prokaryotic hosts. Identification of the promoters regulated during stationary phase growth when the cells reach a certain density is valuable when *Bacillus subtilis* is used as a production host. Similarly, promoters induced by oxygen-limiting conditions are very applicable in industrial settings since oxygen level can adjusted easily.

Investigation of promoter activity in *Bacillus subtilis* or any other bacterium often employs Northern or Southern blots, enzymatic assays, or reporting genes. These methods permit monitoring of the effect of environmental changes on gene expression by comparing expression levels of a limited number of genes. Furthermore, they often enable investigation of one or a subset of the physiological events and fail to monitor the comprehensive responses of a preponderance of individual genes in the genome of an organism in reliable and useful manner.

With the advances in genomic research, a powerful way to identify promoters is the use of DNA microarray. DNA microarray is a technology used to explore gene expression profiles in a genome-wide scale (DeRisi, J. L., V. R. Iyer, and P. O. Brown. 1997. *Science.* 278:680–686). It allows for the identification of genes that are expressed in different growth stages or environmental conditions. This is especially valuable for industrial environments where the conditions for promoter induction have to be convenient, cost effective and compatible with a specific bio-manufacturing process. A significant advance in the art would be a process which would allow for analysis of the timing and extent of induction of most of the genes involved in production and provide inclusive information on the state of the biomass and cell response to growth conditions.

The problem to be solved therefore is to identify genes within the Bacillus genome that are regulated by metabolic conditions or growth cycle changes, and to apply these genes for gene expression and bioreactor monitoring in Bacillus sp. cultures. Applicants have solved the stated problem by using microarray technology to identify genes which are responsive to oxygen depletion, the presence of nitrite, or are sensitive to various stages of the stationary growth phase.

SUMMARY OF THE INVENTION

The present invention provides a method for the expression of a coding region of interest in a Bacillus sp comprising: a) providing a transformed Bacillus sp cell containing a chimeric gene comprising a nucleic acid fragment consisting of the promoter region of a Bacillus gene operably linked to a coding region of interest expressible in a Bacillus sp, wherein the nucleic acid fragment comprising the promoter region of a Bacillus gene is selected from the group consisting of narGHJI, csn, yncM, yvyD, yvaWXY, ydjL, sunA, and yolIJK and homologues thereof; and b) growing the transformed Bacillus sp cell of step (a) in the absence of oxygen wherein the chimeric gene of step (a) is expressed.

Optionally cells may be grown in the presence of oxygen to increase the cell biomass and the oxygen level then decreased to allow for induction and expression for the chimeric gene. Subsequently oxygen levels may be restored to permit bioconversion utilizing the product of the expressed coding region.

Similarly the invention provides a method for the expression of a coding region of interest in a Bacillus sp comprising: a) providing a transformed Bacillus sp cell containing a chimeric gene comprising a nucleic acid fragment consisting of the promoter region of a Bacillus gene operably linked to a coding region of interest expressible in a Bacillus sp, wherein the nucleic acid fragment comprising the promoter region of a Bacillus gene is selected from the group consisting of feuABC, ykuNOP, and dhbABC, and homologues thereof; and b) growing the transformed Bacillus sp cell of step (a) in the absence of oxygen and in the presence of nitrite wherein the chimeric gene of step (a) is expressed.

In another embodiment the invention provides a method for the expression of a coding region of interest in a Bacillus sp comprising: a) providing a transformed Bacillus sp cell containing a chimeric gene comprising a nucleic acid fragment consisting of the promoter region of a Bacillus gene operably linked to a coding region of interest expressible in a Bacillus sp, wherein the nucleic acid fragment comprising the promoter region of a Bacillus gene is selected from the group consisting of ycgMN, dhaS rapF, rapG, rapH, rapK, yqhIJ, yveKLMNOPQST, yhfRSTUV, csn, yncM, yvyD, yvaWXY, ydjL, sunA, and yolIJK, and homologues thereof; and b) growing the transformed Bacillus sp cell of step (a) in the presence of oxygen until the cell reaches about T0 of the stationary phase_wherein the chimeric gene of step (a) is expressed.

In an alternate embodiment the invention provides a method for the expression of a coding region of interest in a Bacillus sp comprising: a) providing a transformed Bacillus sp cell containing a chimeric gene comprising a nucleic acid fragment consisting of the promoter region of a Bacillus gene operably linked to a coding region of interest expressible in a Bacillus sp, wherein the nucleic acid fragment comprising the promoter region of a Bacillus gene is selected from the group consisting of acoABCL, and glvAC, and homologues thereof; and b) growing the transformed Bacillus sp cell of step (a) in the presence of oxygen until the cell reaches about T1 of the stationary phase_wherein the chimeric gene of step (a) is expressed.

In yet another embodiment the invention provides a method for the expression of a coding region of interest in a Bacillus sp comprising: a) providing a transformed Bacillus sp cell containing a chimeric gene comprising a nucleic acid fragment consisting of the promoter region of a Bacillus gene operably linked to a coding region of interest expressible in a Bacillus sp, wherein the nucleic acid fragment comprising the promoter region of a Bacillus gene is selected from the group consisting of yxjCDEF, yngEFGHI, yjmCDEFG, ykFABCD, and yodOPRST; and homologues thereof; and b) growing the transformed Bacillus sp cell of step (a) in the presence of oxygen until the cell reaches about T3 of the stationary phase wherein the chimeric gene of step (a) is expressed.

Within the context of the present invention the Bacillus sp. cell is selected from the species consisting of *Bacillus subtillus, Bacillus thuringiensis, Bacillus anthracis, Bacillus cereus, Bacillus brevis, Bacillus megaterium, Bacillus intermedius, Bacillus thermoamyloliquefaciens, Bacillus amyloliquefaciens, Bacillus circulars, Bacillus licheniformis, Bacillus macerans, Bacillus sphaericus, Bacillus stearothermophilus, Bacillus laterosporus, Bacillus acidocaldarius, Bacillus pumilus,* and *Bacillus pseudofirmus.*

Additionally within the context of the present invention the coding region of interest is selected from the group consisting of crtE crtB, pds, crtD, crtL, crtZ, crtX crtO, phaC, phaE, efe, pdc, adh, genes encoding limonene synthase, pinene synthase, bornyl synthase, phellandrene synthase, cineole synthase, sabinene synthase, and taxadiene synthase.

Additionally the present invention provides a method for monitoring the state of the cell metabolism of a Bacillus sp. culture comprising: a) providing a culture of actively growing Bacillus sp. cells; and b) measuring the expression levels of a pool of genes isolated from the Bacillus cells of step (a), the pool of genes comprising narGHJI, feuABC, ykuNOP, dhbABC, ydjL, sunA, yolIJK, csn, yncM, yvyD, yvaWXY, yhJRSTUV, yveKLMNOPQST, dhaS, rapF, rapG, rapH, rapK, ycgMN, yqhIJ, glvAC, acoABCL, yxjCDEF, yngEFGHIyjmCDEFG, yTfABCD, yodOPRST, alsT, and yxeKLMN, and homologues thereof.

In a preferred embodiment the invention provides a monitoring method wherein an actively growing culture is grown in the absence of oxygen and the expression of genes narGHJI, ydjL, sunA, yolIJK, csn,yncM, yvyD, and yvaWXY are up-regulated in the log phase.

In another preferred embodiment the invention provides a monitoring method wherein the actively growing culture is grown in the absence of oxygen and in the presenece of nitrite and the expression of genes feuABC, ykuNOP, and dhbABC are up-regulated in the log phase.

Similarly the invention provides a monitoring method wherein the expression of genes narGHJI is down-regulated at about T0 of the stationary phase.

Additionally the invention provides a monitoring method wherein the actively growing culture is grown in the presence of oxygen and the expression of genes ycgMN, yqhIJ, ydjL, sunA, yolIJK, csn, yncM, yvyD, yvaWXY, yhfRSTUV, yveKLMNOPQST, dhaS, rapF, rapG, rapH, rapK, are up-regulated at about T0 of the stationary phase.

Similarly the invention provides a monitoring method wherein the actively growing culture is grown in the presence of oxygen and the expression of genes, acoABCL and glvAC are up-regulated at about T1 of the stationary phase.

In an alternate embodiment the invention provides a monitoring method wherein the actively growing culture is grown in the presence of oxygen and the expression of genes, yxjCDEF, yngEFGHI yjmCDEFG, ykABCD, and yodOPRST are up-regulated at about T3 of the stationary phase.

In another embodiment the invention provides a monitoring method wherein the actively growing culture is grown in the presence of oxygen and the expression of genes, alsT and yxeKLMN are down-regulated at stationary phase or under nutrient-limiting conditions.

BRIEF DESCRIPTION OF THE SEQUENCES

The invention can be more fully understood from the following detailed description and the accompanying sequence descriptions which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

| Description | SEQ ID Nucleic acid |
|---|---|
| Nucleotide sequence of a narG gene | 1 |
| Nucleotide sequence of a narH gene | 2 |
| Nucleotide sequence of a narJ gene | 3 |
| Nucleotide sequence of a narI gene | 4 |
| Nucleotide sequence of a csn gene | 5 |
| Nucleotide sequence of a | 6 |

| Description | SEQ ID Nucleic acid |
|---|---|
| yncM gene Nucleotide sequence of a yvyD gene | 7 |
| Nucleotide sequence of a yvaW gene | 8 |
| Nucleotide sequence of a yvaX gene | 9 |
| Nucleotide sequence of a yvaY gene | 10 |
| Nucleotide sequence of a ydjL gene | 11 |
| Nucleotide sequence of a sunA gene | 12 |
| Nucleotide sequence of a yolI gene | 13 |
| Nucleotide sequence of a yolJ gene | 14 |
| Nucleotide sequence of a yolK gene | 15 |
| Nucleotide sequence of a feuA gene | 16 |
| Nucleotide sequence of a feuB gene | 17 |
| Nucleotide sequence of a feuC gene | 18 |
| Nucleotide sequence of a ykuN gene | 19 |
| Nucleotide sequence of a ykuO gene | 20 |
| Nucleotide sequence of a ykuP gene | 21 |
| Nucleotide sequence of a dhbA gene | 22 |
| Nucleotide sequence of a dhbB gene | 23 |
| Nucleotide sequence of a dhbC gene | 24 |
| Nucleotide sequence of a dhaS gene | 25 |
| Nucleotide sequence of a rapF gene | 26 |
| Nucleotide sequence of a rapG gene | 27 |
| Nucleotide sequence of a rapH gene | 28 |
| Nucleotide sequence of a rapK gene | 29 |
| Nucleotide sequence of a yqhI gene | 30 |
| Nucleotide sequence of a yqhJ gene | 31 |
| Nucleotide sequence of a yveK gene | 32 |
| Nucleotide sequence of a yveL gene | 33 |
| Nucleotide sequence of a yveM gene | 34 |
| Nucleotide sequence of a yveN gene | 35 |
| Nucleotide sequence of a yveO gene | 36 |
| Nucleotide sequence of a yveP gene | 37 |
| Nucleotide sequence of a yveQ gene | 38 |
| Nucleotide sequence of a yveS gene | 39 |
| Nucleotide sequence of a yveT gene | 40 |
| Nucleotide sequence of a acoA gene | 41 |
| Nucleotide sequence of a acoB gene | 42 |
| Nucleotide sequence of a acoC gene | 43 |
| Nucleotide sequence of a | 44 |
| acoL gene Nucleotide sequence of a yhfR gene | 45 |
| Nucleotide sequence of a yhfS gene | 46 |
| Nucleotide sequence of a yhfT gene | 47 |
| Nucleotide sequence of a yhfU gene | 48 |
| Nucleotide sequence of a yhfV gene | 49 |
| Nucleotide sequence of a glvA gene | 50 |
| Nucleotide sequence of a glvC gene | 51 |
| Nucleotide sequence of a yxjC gene | 52 |
| Nucleotide sequence of a yxjD gene | 53 |
| Nucleotide sequence of a yxjE gene | 54 |
| Nucleotide sequence of a yxjF gene | 55 |
| Nucleotide sequence of a yngE gene | 56 |
| Nucleotide sequence of a yngF gene | 57 |
| Nucleotide sequence of a yngG gene | 58 |
| Nucleotide sequence of a yngH gene | 59 |
| Nucleotide sequence of a yngI gene | 60 |
| Nucleotide sequence of a yjmC gene | 61 |
| Nucleotide sequence of a yjmD gene | 62 |
| Nucleotide sequence of a yjmE gene | 63 |
| Nucleotide sequence of a yjmF gene | 64 |
| Nucleotide sequence of a yjmG gene | 65 |
| Nucleotide sequence of a ykfA gene | 66 |
| Nucleotide sequence of a ykfB gene | 67 |
| Nucleotide sequence of a ykfC gene | 68 |
| Nucleotide sequence of a ykfD gene | 69 |
| Nucleotide sequence of a yodO gene | 70 |
| Nucleotide sequence of a yodP gene | 71 |
| Nucleotide sequence of a yodR gene | 72 |
| Nucleotide sequence of a yodS gene | 73 |
| Nucleotide sequence of a yodT gene | 74 |
| Nucleotide sequence of a ycgM gene | 75 |
| Nucleotide sequence of a ycgN gene | 76 |
| Nucleotide sequence of a alsT gene | 77 |
| Nucleotide sequence of a yxeN gene | 78 |
| Nucleotide sequence of a yxeM gene | 79 |
| Nucleotide sequence of a yxeL gene | 80 |
| Nucleotide sequence of a yxeK gene | 81 |

DETAILED DESCRIPTION OF THE INVENTION

The present invention advances the art by providing:

(i) the first instance of a comprehensive survey of endogenous promoters and metabolic markers with a microarray comprising greater than 75% of all open reading frames from a *Bacillus subtilis*, overcoming the problems of high concentration of endogenous RNAase and ribosomal RNA;

(ii) A method for the expression of a coding region of interest in a Bacillus sp during the anaerobic growth or induced by oxygen-limiting conditions.

(iii) A method for the expression of a coding region of interest in a Bacillus sp during the stationary growth phase.

(iv) A method for monitoring the metabolic state of Bacillus sp with gene expression patterns generated by DNA microarray.

The present invention has utility in many different fields. Gene expression profiles can be used to detect genotypic alterations among strains. The present invention enables the monitoring of expression profiles when changes in growth conditions occur. The genes of the present invention may be used in a modeling system to test perturbations in fermentation process conditions which will determine the requirements for the high yield of bioprocess production. Additionally, many discovery compounds can be screened by comparing a gene expression profile to a known compound that affects the desirable target gene products.

In this disclosure, a number of terms and abbreviations are used. The following definitions are provided.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

As used herein, the term "oligotucleotide" refers to a nucleic acid, generally of at least 18 nucleotides, that is hybridizable to a genomic DNA molecule, a cDNA molecule, or an mRNA molecule. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid according to the invention. In another embodiment, oligonucleotides (one or both of which may be labeled) can be used as PCR primers, either for cloning full length or a fragment of a nucleic acid of the invention, or to detect the presence of nucleic acids according to the invention. In a farther embodiment, an oligonucleotide of the invention can form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "gene" refers to an assembly of nucleotides that encode a polypeptide, and includes cDNA and genomic DNA nucleic acids. "Gene" also refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise an inducible promoter operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "inducible gene" means any Bacillus gene whose expression is up-regulated in response to a specific stress or stimulus. Inducible genes of the present invention include the genes identified as narGHJI, feuABC, ykuNOP, dhbABC, ydjL, sunA, yolIJK, csn ,yncM, yvyD, yvaWXY, yhjRSTUV, yveKLMNOPQST, dhaS, rapF, rapG, rapH, rapK, yqhIJ, ycgMN, gIvAC, acoABCL, yxjCDEF, yngEFGHI, yjmCDEFG, ykABCD, yodOPRST, alsT, and yxeKLMN.

"Coding sequence" or "open reading frame" (ORF) refers to a DNA sequence that codes for a specific amino acid sequence. A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence. The term "coding region of interest" refers to any coding region or open reading frame that is expressible in a desired host and may be regulated by the promoter of the present inducible genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. "Inducible promoter" mean any promoter that is responsive to a particular stimulus. Inducible promoters of the present invention will typically be derived from the "inducible genes" and will be responsive to various metabolic conditions (oxygen input, nutrient composition, environmental stress such as pH and temperature changes, or overproduction of a particular product or expression of a foreign gene product) or stages in the cell growth cycle.

The term "expression", as used herein, refers to the transcription and stable accumulation of sense (mRNA) or antisense RNA derived from the nucleic acid fragment of the invention. Expression may also refer to translation of mRNA into a polypeptide.

The term "up-regulated" as applied to gene expression means the mRNA transcriptional level of a particular gene or region in the test condition is increased as compared to the control condition.

The term "down-regulated" as applied to gene expression means the mRNA transcriptional level of a particular gene or region in the test condition is decreased as compared to the control condition.

The term "homologue" as applied to a gene means any gene derived from the same or a different microbe having the same function and may have significant sequence similarity.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "genomic DNA" refers to total DNA from an organism.

The term "total RNA" refers to non-fractionated RNA from an organism.

The term "probe" refers to a single-stranded nucleic acid molecule that can base pair with a complementary single stranded target nucleic acid to form a double-stranded molecule.

The term "label" will refer to any conventional molecule which can be readily attached to mRNA or DNA and which can produce a detectable signal, the intensity of which indicates the relative amount of hybridization of the labeled probe to the DNA fragment. Preferred labels are fluorescent molecules or radioactive molecules. A variety of well-known labels can be used.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "growth cycle" as applied to a cell refers to the metabolic cycle through which a cell moves in culture conditions. The cycle may be divided into various stages known as the exponential phase, the end of exponential, and the stationary phase.

The term "exponential growth", "exponential phase growth", "log phase" or "log phase growth" refer to the rate at which microorganisms are growing and dividing. When growing in log phase microorganisms are growing at the maximal rate possible given their genetic potential, the nature of the medium, and the conditions under which they are grown. Microorganism rate of growth is constant during exponential phase and the microorganism divides and doubles in number at regular intervals. Cells that are "actively growing" are those that are growing in log phase.

The term "stationary phase" refers to the growth cycle phase where cell growth in a culture slows or even ceases. In *Bacillus subtilis,* T0 represents the end of the exponential growth phase or the beginning of the stationary phase. T1 means one hour after T0 or one hour into the stationary phase. T3 means three hours from T0 or three hours into the stationary phase.

The term "growth-altering environment" refers to energy, chemicals, or living things that have the capacity to either inhibit cell growth or kill cells. Inhibitory agents may include but are not limited to mutagens, antibiotics, UV light, gamma-rays, x-rays, extreme temperature, phage, macrophages, organic chemicals and inorganic chemicals.

"State of the cell" refers to metabolic state of the organism when grown under different conditions.

The term "alkyl" will mean a univalent group derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively.

The term "alkenyl" will mean an acyclic branched or unbranched hydrocarbon having one carbon-carbon double bond and the general formula $C_nH_{2n}$. Acyclic branched or unbranched hydrocarbons having more than one double bond are alkadienes, alkatrienes, etc.

The term "alkylidene" will mean the divalent groups formed from alkanes by removal of two hydrogen atoms from the same carbon atom, the free valencies of which are part of a double bond (e.g. $(CH_3)_2C$=propan-2-ylidene).

The term "DNA microarray" or "DNA chip" means the assembling of PCR products of a group of genes or all genes within a genome on a solid surface in a high density format or array. General methods for array construction and use are available (see Schena M., Shalon D., Davis R. W., Brown P. O., Quantitative monitoring of gene expression patterns with a complementary DNA microarray. *Science.* Oct. 20, 1995; 270(5235). A DNA microarray allows for the analysis of gene expression patterns or profiles of many genes to be performed simultaneously by hybridizing the DNA microarray comprising these genes or PCR products of these genes with cDNA probes prepared from the sample to be analyzed. DNA microarray or "chip" technology permits examination of gene expression on a genomic scale, allowing transcription levels of many genes to be measured simultaneously. Briefly, DNA microarray or chip technology comprises arraying microscopic amounts of DNA complementary to genes of interest or open reading frames on a solid surface at defined positions. This solid surface is generally a glass slide, or a membrane (such as nylon membrane). The DNA sequences may be arrayed by spotting or by photolithography. Two separate fluorescently-labeled probe mixes prepared from the two sample(s) to be compared are hybridized to the microarray and the presence and amount of the bound probes are detected by fluorescence following laser excitation using a scanning confocal microscope and quantitated using a laser scanner and appropriate array analysis software packages. Cy3 (green) and Cy5 (red) fluorescent labels are routinely used in the art, however, other similar fluorescent labels may also be employed. To obtain and quantitate a gene expression profile or pattern between the two compared samples, the ratio between the signals in the two channels (red:green) is calculated with the relative intensity of Cy5/Cy3 probes taken as a reliable measure of the relative abundance of specific mRNAs in each sample. Materials for the construction of DNA microarrays are commercially available (Affymetrix (Santa Clara Calif.) Sigma Chemical Company (St. Louis, Mo.) Genosys (The Woodlands, Tex.) Clontech (Palo Alto Calif.) and Corning (Corning N.Y.). In addition, custom DNA microarrays can be prepared by commercial vendors such as Affymetrix, Clontech, and Corning.

The term "expression profile" refers to the expression of groups of genes under a given conditions.

The term "gene expression profile" refers to the expression of an individual gene and of suites of individual genes.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Austibel, F. M. et al., *Current Protocols in Molecular Biology*, published by Greene Publishing Assoc. and Wiley-Interscience (1987).

The present invention identifies a number of genes contained within the *Bacillus subtilis* genome that are responsive to various metabolic conditions or growth cycle conditions. The discovery that these genes are regulated in response to these conditions allows for their use in gene expression and in the monitoring and regulating of bioreactor health.

Generation of Microarrays

The invention identifies a number of genes known in the art as being responsive to various conditions not heretofore appreciated. The identification of these new inducing conditions was made by means of the application of DNA mircoarray technology to the *Bacillus subitilis* genome. Any Bacillus species may be used, however *Bacillus subtillis* strain, obtained from Bacillus Genetic Stock Center (Ohio State University, Columbus, Ohio) is preferred.

The generation of DNA microarrays is common and well known in the art (see for example Brown et al., U.S. Pat. No. 6,110,426). Typically generation of a microarry begins with providing a nucleic acid sample comprising mRNA transcript(s) of the gene or genes, or nucleic acids derived from the mRNA transcript(s) to be included in the array. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

Typically the genes are amplified by methods of primer directed amplification such as polymerase chain reaction (PCR) (U.S. Pat. No. 4,683,202 (1987, Mullis, et al.) and U.S. Pat. No. 4,683,195 (1986, Mullis, et al.), ligase chain reaction (LCR) (Tabor et al., *Proc. Acad. Sci. U.S.A.*, 82, 1074–1078 (1985)) or strand displacement amplification (Walker et al., *Proc. Natl. Acad. Sci. U.S.A.*, 89, 392, (1992)) for example.

Amplified ORF's are then spotted on slides comprised of glass or some other solid substrate by methods well known in the art to form a micro-array. Methods of forming high density arrays of oligonucleotides, with a minimal number of synthetic steps are known (see for example Brown et al., U.S. Pat. No. 6,110,426). The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using, for example, light-directed synthesis techniques. See also, Fodor et al., *Science*, 251, 767–77 (1991).

The ORF's are arrayed in high density on at least one glass microscope slide. Once all the genes of ORF's from the genome are amplified, isolated and arrayed, a set of probes, bearing a signal generating label are synthesized. Probes may be randomly generated or may be synthesized based on the sequence of specific open reading frames. Probes are typically single stranded nucleic acid sequences which are complementary to the nucleic acid sequences to be detected. Probes are "hybridizable" to the ORF's. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Signal generating labels that may be incorporated into the probes are well known in the art. For example labels may include but are not limited to fluorescent moieties, chemiluminescent moieties, particles, enzymes, radioactive tags, or light emitting moieties or molecules, where fluorescent moieties are preferred. Most preferred are fluorescent dyes capable of attaching to nucleic acids and emitting a fluorescent signal. A variety of dyes are known in the art such as fluorescein, texas red, and rhodamine. Preferred are the mono reactive dyes cy3 (146368-16-3) and cy5 (146368-14-1) both available commercially (i.e. Amersham Pharmacia Biotech, Arlington Heights, Ill.). Suitable dyes are discussed in U.S. Pat. No. 5,814,454 hereby incorporated by reference.

Labels may be incorporated by any of a number of means well known to those of skill in the art. However, in a preferred embodiment, the label is simultaneously incorporated during the amplification step in the preparation of the probe nucleic acids. Thus, for example, polymerase chain reaction (PCR) with labeled primers or labeled nucleotides will provide a labeled amplification product. In a preferred embodiment, reverse transcription or replication, using a labeled nucleotide (e.g. dye-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the synthesis is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Following incorporation of the label into the probe the probes are then hybridized to the micro-array using standard conditions where hybridization results in a double stranded nucleic acid, generating a detectable signal from the label at the site of capture reagent attachment to the surface. Typically the probe and array must be mixed with each other under conditions which will permit nucleic acid hybridization. This involves contacting the probe and array in the presence of an inorganic or organic salt under the proper concentration and temperature conditions. The probe and array nucleic acids must be in contact for a long enough time that any possible hybridization between the probe and sample nucleic acid may occur. The concentration of probe or array in the mixture will determine the time necessary for hybridization to occur. The higher the probe or array concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate. Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)) and Maniatis, supra.

Identification of Responsive Genes

The basis of gene expression profiling via micro-array technology relies on comparing an organism under a variety of conditions that result in alteration of the genes expressed. Within the context of the present invention a single population of cells was exposed to a variety of stresses that resulted in the alteration of gene expression. The stresses or induction conditions analyzed included 1) oxygen deprivation 2) the combination of oxygen deprivation and presence of nitrite and 3) reaching the stationary growth phase. Non-stressed cells are used for generation of "control" arrays and stressed cells are used to generate an "experimental", "stressed" or "induced" arrays.

Using the above described method of DNA microarray technology and comparing induced vs. non-induced cultures it was determined that the genes narGHJI, csn, yncM, yvyD, yvaWXY, ydjL, sunA, and yolIJK are induced in the absence of oxygen in the log or exponential phase of the Bacillus cell cycle. Similarly it was determined that absence of oxygen combined with the presence of nitrite was sufficient to upregulate or induce the genesfeuABC, ykuNOP, and dhbABC. Typically the concentration of nitrite is from about 1 mM to about 10 mM in the medium. In these instances the necessary elements for induction include both the lack of oxygen and growth in the log phase. Either the addition of oxygen or reaching the stationary growth phase resulted in the down regulation of these genes.

Additionally it was discovered that a number of genes were highly induced at various times in the stationary phase of the cell growth cycle. For example, reaching T0 of the stationary phase under aerobic conditions was sufficient to upregulate the genes ycgMN, dhaS rapF, rapG, rapH, rapK, yqhIJ yveKLMNOPQST, yhfRSTUV, csn, yncM, yvyD, yvaWXY, ydjL, sunA, and yolIJK. Similarly reaching T1 of the stationary phase under aerobic conditions was sufficient to upregulate the genes acoABCL, and glvAC. Reaching T3 of the stationary phase under aerobic conditions was sufficient to upregulate the genes yxjCDEF, yngEFGHI, yjmCDEFG, ykfACD, and yodOPRST In addition to the discovery of the induction conditions for the above mentioned genes, it was further discovered that a number of genes were down regulated at very specific times during the growth cycle. For example, alsT and yxeKLMN regions are down-regulated upon entering the stationary phase, It will be appreciated by the skilled person that the genes of the present invention have homologues in a variety of Bacillus species and the use of the genes for heterologus gene expression and the monitoring of bioreactor health and production are not limited to those genes derived from *Bacillus subitillis* but extend to homologues in any Bacillus species if they are present. For example the invention encompasses homologues derived from species including, but not limited to *Bacillus subtillus, Bacillus thuringiensis, Bacillus anthracis, Bacillus cereus, Bacillus brevis, Bacillus megaterium, Bacillus intermedius, Bacillus thermoamyloliquefaciens, Bacillus amyloliquefaciens, Bacillus circulans, Bacillus licheniformis, Bacillus macerans, Bacillus sphaericus, Bacillus stearothermophilus, Bacillus laterosporus, Bacillus acidocaldarius, Bacillus pumilus,* and *Bacillus pseudofirmus*. Although all of the genes of the present invention have been identified in the *Bacillus subtilis* genome (Kunst et al., *Nature* 390 (6657), 249–256 (1997) homologs of csn for example have been identified in *Bacillus circulans,* and *Bacillus ehimensis* (Shimosaka et al., *Appl. Microbiol. Biotechnol.* (2000), 54(3), 354–360; Masson et al., *Gene* (1994), 140(1), 103–7 and in *Bacillus amyloliquefaciens* (Seki et., *Adv. Chitin Sci.* (1997), 2, 284–289.

The function of the instant genes and the conditions under which they are up-regulated or down-regulated are given in Table 1 below.

TABLE 1

| Gene or Gene Cluster Name* | Function | Up-regulated | Down-regulated |
| --- | --- | --- | --- |
| NarGHJI | Nitrate reduction | in Log Phase under oxygen-limiting conditions | Stationary Phase under oxygen-limitation conditions |
| csn | chitosanase | O2 depletion in Log Phase or +O2 in stationary Phase in the | |
| yncM | Unknown | O2 depletion in Log Phase or +O2 in | |

TABLE 1-continued

| Gene or Gene Cluster Name* | Function | Up-regulated | Down-regulated |
| --- | --- | --- | --- |
| | | stationary Phase | |
| yvyD | | O2 depletion in Log Phase or +O2 in stationary Phase | |
| yvaWXY | | O2 depletion in Log Phase or +O2 in stationary Phase | |
| ydjL | | O2 depletion in Log Phase or +O2 in stationary Phase | Stationary Phase |
| sunA | Sublancin lantibiotic | O2 depletion in Log Phase or +O2 in stationary Phase (T0 & T1) | |
| yolIJK | Modification of SunA | O2 depletion in Log Phase or +O2 in stationary Phase (T0 & T1) | |
| feuABC | Fe transport | O2 limiting-condition and in the presence of nitrite | |
| ykuNOP | Unknown | O2 limiting-condition and in the presence of nitrite | |
| dhbABC | Fe uptake | O2 limiting-condition and in the presence of nitrite | |
| dhaS | aldehyde dehydrogenase | Aerobic, stationary (T0, T1, T3) | |
| rapF | response regulator aspartate phosphatase | Aerobic, stationary (T0, T1, T3) | |
| rapG | response regulator aspartate phosphatase | Aerobic, stationary (T0, T1, T3) | |
| rapH | response regulator aspartate phosphatase | Aerobic, stationary (T1, T1, T3) | |
| rapK | response regulator aspartate phosphatase | Aerobic, stationary (T0, T1, T3) | |
| yqhIJ | Possibly involved in amino acide biosynthesis | Aerobic, stationary (T0, T1, T3) | |
| yveKLMNOPQST, | Polysaccharide biosythesis | Aerobic, stationary (T0, T1) | |

TABLE 1-continued

| Gene or Gene Cluster Name* | Function | Up-regulated | Down-regulated |
|---|---|---|---|
| yhfRSTUV | unknown | Aerobic, stationary (T0) | |
| acoABCL, | Acetoin metablism | Aerobic, stationary (T1, T3) | |
| glvAC | glvA 6-phospho-alpha-glucosidase | Aerobic, stationary (T1) | |
| yxjCDEF | unknown | Aerobic, stationary (T3) | |
| yngEFGHI | unknown | Aerobic, stationary (T3) | |
| yjmCDEFG | unknown | Aerobic, stationary (T3) | |
| ykfABCD | unknown | Aerobic, stationary (T3) | |
| yodOPRST | .YodO, lysine 2,3-aminomutase Rest unknown | Aerobic, stationary (T3) | |
| ycgMN | Possible proline biosynthesis | Aerobic stationary (T1, T0, T3) | |
| alsT | sodium/proton-dependent alanine carrier (alsT) | | Aerobic stationary |
| yxeKLMN | Similar to amino acid transporter or monooxygenase | | Aerobic stationary |

*All genes have been identified in the complete sequence of the *Bacillus subtilis* genome
(Kunst et al., Nature 390 (6657), 249–256 (1997)

Although narGHJI and acoABCL have been previously characterized using DNA microarray technology, Applicants have been able to compare the relative fold induction of the genes with more than 4,000 other genes in the genome to derive new functional information. For example it was seen that the narGHJI was the highest induced region under anaerobic conditions in the log phase. The acoABCL is the highest induced region after one hour into the stationary phase. These findings demonstrate that the promoter regions from these genes may be used to regulate gene expression or they may function as diagnostic markers.

Expression Profiles to Monitor Biomass

The genes of the present invention may be used in a variety of formats for the monitoring of the state of biomass in a reactor.

A gene expression profile is a reflection of the environmental conditions within which a cell is growing at anyone particular time. As a result, these profiles or patterns can be used as markers to describe the metabolic state of the cells. For example, an increase in mRNA levels for ycgMN, rapF, rapK, rapH, rapG, yvyD, yvaWXY, sunA, yncM, ydjL, yhfRSTUV genes and a reduction in alsT and yxeKLMN will indicate the cell is experiencing nutrient limitation since their expression levels start to change at the end of exponential phase. If the DNA regions yjmCDEFG, ykfABCD, yngEFGHI, and yxjDDEF show increased mRNA levels, that will suggest a more severe state of nutrient limitation since they are normally expressed three hours into the stationary phase. Similarly an increase in transcription for sunA, yolIJK, yvaWXY, ydjL, yvyD, csn, and yncM, but not other stationary phase genes, will indicate a limitation in oxygen supply to the cell.

Formats for using these genes for biomass monitoring will vary depending on the type of fermentation to be monitored and will include but is not limited to DNA microarry analysis, northern blots [Krumlauf, Robb, *Methods Mol. Biol.* (Totowa, N.J.) (1991), 7 (Gene Transfer Expression Protocols), 307–23,] primer extension, and nuclease protection assays [Walmsley et al., *Methods Mol. Biol.* (Totowa, N.J.) (1991), 7 (Gene Transfer Expression Protocols), 271–81] or other mRNA quantification procedures. Methods of gene expression monitoring with DNA microarrays typically involve (1) construction of DNA microarray for *Bacillus subtilis* (2) RNA isolation, labeling and slide hybridization of a nucleic acid target sample to a high density array of nucleic acid probes, and (3) detecting and quantifying the amount of target nucleic acid hybridized to each probe in the array and calculating a relative expression. Hybridization with these arrays permits simultaneous monitoring of the various members of a gene family and subsequently allows one to optimize production yield in a bioreactor by monitoring the state of the biomass.

Furthermore, the expression monitoring method of the present invention allows for the development of "dynamic" gene database that defines a gene's function and its interaction with other genes. The identified genes can be used to study the genes responsible for the inactivation and expression analysis of the unanalyzed genes in different regions of *Bacillus subtilis* genome. The results of this kind of analysis provides valuable information about the necessity of the inactivated genes and their expression patterns during growth in different conditions.

Additionally, the genes which have been identified by the present invention can be employed as promoter candidates and diagnostic markers for the metabolic state of the organism and potential stress factors or limitations of nutrients during growth. For example,.an optimized process for the production of a specific bio-based material can be developed with the promoters and gene expression patterns in the present invention. Such a process could involve culture media change, oxygen input, nutrient composition, environmental stress (such as pH and temperature changes), overproduction of a particular product or expression of a foreign gene product. Accordingly, through the use of such methods, the present invention may be-used to monitor global expression profiles which reflect the state of the cell.

Regulated Gene Expression

The genes of the present invention may be used to effect the regulated expression of chimeric genes in various Bacillus sp. under specific induction conditions or at a specific point in the cell growth cycle. Useful chimeric genes will include the promoter region of any one of the inducible genes defined herein, operably linked to a coding region of interest to be expressed in a Bacillus host. Any host that is capable of accommodating the promoter region is suitable including but not limited to *Bacillus subtillus, Bacillus thuringiensis, Bacillus anthracis, Bacillus cereus, Bacillus brevis, Bacillus megaterium, Bacillus intermedius, Bacillus thermoamyloliquefaciens, Bacillus amyloliquefaciens, Bacillus circulans, Bacillus licheniformis, Bacillus macerans, Bacillus sphaericus, Bacillus stearothermophilus, Bacillus laterosporus, Bacillus acidocaldarius, Bacillus pumilus,* and *Bacillus pseudofirmus.*

Coding regions of interest to be expressed in the recombinant Bacillus host may be either endogenous to the host or heterologous and must be compatible with the host organism. Genes encoding proteins of commercial value are particularly suitable for expression. For example, coding regions of interest may include, but are not limited to those encoding viral, bacterial, fungal, plant, insect, or vertebrate, including mammalian polypeptides and may be, for example, structural proteins, enzymes, or peptides. A particularly preferred, but non-limiting list include, genes encoding enzymes involved in the production of isoprenoid molecules, genes encoding polyhydroxyalkanoic acid (PHA) synthases (phaE; Genbank Accession No. GI 1652508, phaC; Genbank Accession No. GI 1652509) from Synechocystis or other bacteria, genes encoding carotenoid pathway genes such as phytoene synthase (crtB; Genbank Accession No. GI 1652930), phytoene desaturase (crtD; Genbank Accession No. GI 1652929), beta-carotene ketolase (crtO; Genbank Accession No. GI 1001724); and the like, ethylene forming enzyme (efe) for ethylene production, pyruvate decarboxylase (pdc), alcohol dehydrogenase (adh), cyclic terpenoid syntahses (i.e. limonene synthase, pinene synthase, bornyl synthase, phellandrene synthase, cineole synthase, and sabinene synthase) for the production of terpenoids, and taxadiene synthase for the production of taxol, and the like. Genes encoding enzymes involved in the production of isoprenoid molecules include for example, geranylgeranyl pyrophosphate synthase (crtE; Genbank Accession No. GI 1651762), solanesyl diphosphate synthase (sds; Genbank Accession No. GI 1651651), which can be expressed in Bacillus to exploit the high flux for the isoprenoid pathway in this organism. Genes encoding polyhydroxyalkanoic acid (PHA) synthases (phaE, phac) may be used for the production of biodegradable plastics.

The initiation regions or promoters for construction of the chimera to be expressed will be derived from the inducible genes identified herein. The promoter regions may be identified from the sequence of the inducible genes and their homologues (see Table 1) and isolated according to common methods (Maniatis supra). Once the promoter regions are identified and isolated they may be operably linked to a coding region of interest to be expressed in suitable expression vectors.

Examples of sequence-dependent protocols for homologue identification include, but are not limited to, methods of nucleic acid hybridization, and methods of DNA and RNA amplification as exemplified by various uses of nucleic acid amplification technologies [e.g., polymerase chain reaction, Mullis et al., U.S. Pat. No. 4,683,202; ligase chain reaction,(LCR), Tabor, S. et al., *Proc. Acad. Sci. USA* 82, 1074, (1985)] or strand displacement amplification [SDA, Walker, et al., *Proc. Natl. Acad. Sci. U.S.A.*, 89, 392, (1992)].

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively the instant sequences may be employed as hybridization reagents for the identification of homologues. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected.

Vectors or cassettes useful for the transformation of suitable Bacillus host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Termination control regions may also be derived from various genes native to the preferred hosts. Optionally, a termination site may be unnecessary, however, it is most preferred if included.

Application of integration vectors for genetic manipulation is very well established and widely used in *Bacillus subtilis* (M. Perego, 1993, In *Bacillus subtilis* and Other Gram-Positive Bacteria, p.615–624.). Alternatively, the promoters to be used can be cloned into a plasmid which is capable of transforming and replicating itself in *Bacillus subtilis* (L. Janniere, et al, In *Bacillus subtilis* and Other Gram-Positive Bacteria, p. 625–644; Nagarajan et al, 1987, U.S. Pat. No. 4,801,537). The gene to be expressed can then be cloned downstream from the promoter. Once the recombinant Bacillus sp. is established, gene expression can be accomplished by the conditions such as oxygen-limitation, nitrite addition and others.

Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

The meaning of abbreviations is as follows: "hr" means hour(s), "mim" means minute(s), "sec" means second(s), "d" means day(s), "mL" means milliliter(s), "$\mu$L" means microliter(s), "nL" means nanoliter(s), "$\mu$g" means microgram(s), "ng" means nanogram(s), "mM" means millimole(s), "$\mu$M" means micromole(s).

Media and Culture Conditions

Materials and methods suitable for the maintenance and growth of bacterial cultures were found in *Experiments in Molecular Genetics* (Jeffrey H. Miller), Cold spring Harbor Laboratory Press (1972), *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210–213, American Society for Microbiology, Washington, D.C. or Thomas D. Brock in *Biotechnology: A Textbook of Industrial Microbiology,* Second Edition (1989) Sinauer Associates, Inc., Sunderland Mass. All reagents and materials used for the growth and maintenance of bacterial cells were obtained from Aldrich Chemicals (Milwaukee, Wis.), DIFCO Laboraoties (Detroit, Mich.), Gibco/BRL (Gaithersburg, Md.), or Sigma Chemical Company (St. Louis, Mo.) unless otherwise specified.

Molecular Biology Techniques

Methods for agarose gel electrophoresis were performed as described in Sambrook, J., et al., *Molecular Cloning: A Laboratory Manual,* Second Edition, Cold Spring Harbor Laboratory Press (1989). Polymerase Chain Reactions (PCR) techniques were found in White, B., *PCR Protocols: Current Methods and Applications,* Volume 15(1993) Humana Press Inc.

Example 1

Application of DNA Microarray Technology in *Bacillus subtilis*

Example 1 describes a procedure for the use of DNA microarray in *Bacillus subtilis* following growth of the cells in different growth medium. The signal intensity of each spots in the array was used to determine genome-wide gene expression patterns of this organism.

*Bacillus subtilis* Strain and Culture Media

*Bacillus subtilis* strain 168 (a derivative JH642) was obtained from Bacillus Genetic Stock Center (Ohio State University, Columbus, Ohio). Cells were routinely grown at 37° C. in the following media: 2xYT medium (Gibco BRL, Gaithersburg, Md.) or Schaeffer's sporulation medium. One liter of the Schaeffer's medium contains the following ingredient: 8 g Bacto-nutrient broth, 1 g of KCl, 0.12 g of $MgSO_4.7H_2O$, 0.5 ml of 1.0 MNaOH, 1 ml of 1.0 M $Ca(NO_3)_4$, 1 ml of 0.01 M $MnCl_2$, and 1 ml of 1.0 mM $FeSO_4$.

Construction of DNA Microarray for *Bacillus subtilis*

The oligonucleotides for all 4,100 ORFs of the *Bacillus subtilis* genome were purchased from Genosys (Woodlands, Tex.). The HotStart PCR kit from Qiagen (Valencia, Calif.) was used for all PCR reactions. The cycling conditions were as follows: 30 seconds of annealing at 55° C., 2 minutes of elongation at 72° C., and 30 seconds of denaturing at 95° C. The PCR products were purified with the QIAquick Multi-well PCR purification kit from Qiagen and the quality of the PCR reactions was checked by electrophoresis on an agarose gel (1%). Each image was stored in a database and the observed sizes of PCR products were automatically compared to the expected value. This information was also used as a reference to check the quality of hybridization at a later stage. After two rounds of PCR reactions, about 95% of the PCR reactions were successful and the remaining ORFs were amplified with another set of oligonucleotides. If an ORF was larger than 3 kb, only a portion of the gene (2 kb or less) was amplified. A total of 4,020 PCR products were obtained. These PCR products were spotted onto sodium thiocyanate optimized Type 6 slides (Amersham Pharmacia Biotech, Piscataway, N.J.) with the Molecular Dynamics Generation III spotter (Sunnyvale, Calif.). Each of the 4,020 PCR products was spotted in duplicate on a single slide.

Each array slide also contained 10 different internal controls consisting different 1.0 kb lambda DNA fragments. The PCR product of each control was spotted in three different locations in the array. Every control fragment also contained a T7 promoter generated by PCR reaction. PCR products were directly used to generate RNAs with the in vitro transcription kit (Ambion, Austin, Tex.). An equal amount of control mRNA mixture was spiked into the two total RNA samples before each labeling.

RNA Isolation, Labeling and Slide Hybridization

Total RNA was isolated from *Bacillus subtilis* with the Qiagen RNeasy Mini kit. The cell culture was harvested by centrifugation with a Bechman table top centifuge (Beckman Instruments, Fullerton, Calif.). The speed of centrifuge was brought up to 9,000 rpm and then stop immediately. Cells were suspended directly in RLT buffer and placed in a 2 ml tube with ceramic beads from the FastRNA kit (Bio101, Vista, Calif.). The tube was shaken for 40 seconds at the speed setting of 4.0 in a bead beater (FP120 FastPrep cell disrupter, Savant Instruments, Inc., Holbrook, N.Y.). Residue DNA was removed on-column with Qiagen RNase-free DNase. To generate cDNA probes with reverse transcriptase, 10 to 15 ug of RNA was used for each labeling reaction. The protocol for labeling was similar to the one previously described for yeast (DeRisi, J. L., V. R. Iyer, and P. O. Brown, 1997, Exploring the metabolic and genetic control of gene expression on a genomic scale, Science. 278:680–686). For this work, random hexamers (Gibco BRL) were used for priming and the fluorophor Cy3-dCTP or Cy5-dCTP (Amersham Pharmacia Biotech) was used for labeling. After labeling, RNA was removed by NaOH treatment and cDNA was immediately purified with a Qiagen PCR Mini kit. The efficiency of labeling was routinely monitored by the absorbance at 260 run (for DNA concentration), 550 nm (for Cy5), and 650 nm (for Cy3).

Each total RNA preparation was labeled with both Cy3-dCTP and Cy5-dCTP. To hybridize a single glass slide, the Cy3-labeled probe from one growth condition was mixed with the Cy5-labeled probe from another and vice versa. As a result, each experiment required two slides. An equal amount of Cy3- and Cy5-labeled probes based on the incorporated dye concentration was applied to each slide. The amount of cy3- and Cy5-labeled probe was determined by the extinction coefficient at 550 nm (for Cy5 dye) and 650 nm (Cy3). The hybridization was carried out at 37° C. overnight with Microarray Hybridization Buffer containing formamide (Amersham Pharmacia Biotech). Slides were washed at 15 min intervals, once with a solution containing 2×SSC and 0.1% SDS at 37° C. and three times with a solution containing 0.1×SSC and 0.1% SDS at room temperature. The slides were then rinsed with 0.1×SSC and dH$_2$O. After drying under a stream of N$_2$, the slides were scanned for fluorescent intensity of both Cy5 and Cy3 fluors. The signal from each spot in the array was quantified using ArrayVision software from Molecular Dynamics.

Data Analysis and Presentation. There are two ways to calculate the signal intensity of each spot. One is the normalized density x area (nDxA), which is the fluorescence units (after background subtraction) divided by the reference. The reference is the mean DxA-background of all elements in the array. The second signal intensity is the DxA after background subtraction. Normalization was carried out with internal controls. The purpose of normalization in the first case is to correct the errors generated due to slide and slide variation and difference in the efficiency of Cy5 and Cy3 incorporation so that data generated within the slide and from different slides can be compared directly. This method is based on total mRNA signals in the array and assumed that less than 10% of the population changed between the two conditions. The purpose of using DxA and normalization with internal controls is to measure the changes in mRNA levels when more than 10% of the total population has been changed. This method is based on total RNA level.

The ratio of intensity for Cy-3/Cy-5 or Cy-5/Cy-3 from two slides of each dye swap hybridization was averaged as one independent experiment. Data were obtained from at least three independent experiments. The ratio of spot intensity represents the relative abundance of mRNA levels under the conditions studied. The levels of mRNA often reflects fold of induction or reduction of a particular DNA region.

Example 2

Identification of Anaerobically Induced DNA Region in Bacillus subtilis at Exponential Phase Using a Bacillus subtilis DNA microarray prepared according to the methods described in Example 1, applicants have identified promoters that can be employed for different level of gene expression in Bacillus subtilis and like organisms with oxygen-limiting environment as the induction conditions. This Example describes the identification of anaerobically induced genes and their corresponding promoters in Bacillus subtilis when grown in 2× YT medium. Cells grown at exponential were used.

Specifically, Bacillus subtilis strains were grown at 37° C. in 2×YT medium supplemented with 1% glucose and 20 mM K$_3$PO$_4$ (pH 7.0). For aerobic growth, 20 ml prewarmed medium was inoculated with 0.1 ml of overnight culture (1:200 dilution) in a 250 ml flask placed on a rotary platform at the speed of 250 rpm. For anaerobic growth, 120 ml prewarmed medium was placed in a 150 ml serum bottle. Three anaerobic growth conditions were tested: anaerobic growth with nitrate as the alternative electron acceptor, anaerobic growth with nitrite as the alternative electron acceptor, and fermentative growth without the presence of nitrate or nitrite. Potassium nitrate at a concentration of 5 mM or potassium nitrite at a concentration 2.5 mM was added if used. To create an anaerobic environment, the serum bottle was capped with a Teflon coated stopper and the gas phase was flushed and filled with argon gas.

To isolate RNA from the exponential cultures, samples were taken at 0.4 O.D. at 600 nm for aerobic cultures, 0.25 O.D. for cultures grown on nitrate, 0. 15 O.D. for cultures grown on nitrite, 0.12 O.D. for cultures grown with no amendments and 0.3 O.D. if pyruvate was added during fermentative growth. Total RNA was isolated and labeled with fluorescent dyes as described in Example 1. Each hybridization consisted of aerobic and one of the various anaerobic probes, containing either nitrate, nitrite or no amendment. If the ratio between anaerobic and aerobic samples was high, it indicated that a particular gene or DNA region was induced under anaerobic conditions. With this DNA microarray technology, the highest induced region in all anaerobic conditions was narGHJI after all the expression patterns of 4,020 genes were examined. The narGHJI region has been shown to be induced under anaerobic conditions, but only with the DNA microarray techniques that the level of induction relative to all other genes can be determined. The new anaerobic genes identified by this technique were ydjL, csn, yvyD, yvaW, yvax, and yvaY. These genes have not been characterized and many of them are unknown. Surprisingly, there were three DNA regions that were specifically induced changes in growth conditions when nitrite was used as the electron acceptor. They include dhb, ykuNOP, and feu regions. This unique characteristic of gene induction by nitrite can be used as a mean to design expression vectors.

TABLE 2

Fold induction for genes or gene clusters involved in nitrate and nitrite respiration in Bacillus subtilis JH642 when grown under anaerobic conditions.

| Gene | Description | Nitrate* | Nitrite* | No Amendment* |
|---|---|---|---|---|
| narGHJI | nitrate reductase | 112–600 | 102–743 | 61–430 |
| ydjL | similar to 2,3-butanediol or sorbitol dehydrogenase | 7.7 | 11.6 | 23.2 |
| csn | chitosanase | 13.3 | 11.4 | 27.4 |
| yncM | unknown | 4.0 | 6.4 | 21.5 |
| yvyD | unknown | 3.8 | 5.6 | 6.4 |
| yvaWXY | unknown | 5–9 | 7.0–8 | 4.5–5 |
| feuABC | Fe transport | | 10–15 | |
| dhbABC | Fe uptake | | 39–50 | |
| ykuNOP | Unknown | | 18–19 | |

*Units in fold induction vs control

Example 3

Identification of DNA Regions Induced at Stationary Phase with Cells Grown in the Presence of Oxygen Using a Bacillus subtilis DNA microarray prepared according to the methods described in Example 1, applicants have identified herein promoters that can be employed for gene expression in Bacillus subtilis and like organisms when the cells reached stationary phase in the presence of oxygen. This example describes the identification of genes and their corresponding promoters induced at different stages of stationary phase when the culture was grown in the presence of oxygen in Schaeffer's, medium supplemented with 0.1% glucose and 20 mM K$_3$PO$_4$ (pH 7.0).

Specifically, Bacillus subtilis strains were grown at 37° C. An aliquot of 20 ml prewarmed medium was inoculated with overnight culture to give an O.D. of 0.03 to 0.04 in a 250 ml flask placed on a rotary platform at the speed of 250 rpm. The exponential culture for RNA preparation was harvested at mid log. Cells collected at the end of exponential growth, one hour and three hours into the stationary phase were considered as T0, T1 and T3 samples, respectively. RNA isolation, labeling, and slide hybridization were carried out as described in Example 1. For hybridization, each slide contained two probes, mid-log sample and one of the stationary samples (T0, T1, or T3).

To identify genes induced at stationary phase in the presence of oxygen, the mRNA signals between exponential (log) and one of the stationary samples (T0, T1, or T3) were compared. If the ratio between stationary and log samples was high, it indicated that a particular gene or DNA region was up-regulated at stationary phase. With this DNA microarray technology, many genes were found to have an increased level of mRNA in different stages as shown in Table 3. Genes such as ycgMN, csn, yvaW, yvaX, yvaY yncM, yvyD, and yqhIJ were all induced in all three stages. Gene such as yolI, yolJ, yolK and ydjL were mostly induced at stage T0 and T2. Expression patterns of these genes at stationary phase had not been studied before. The aco regions involved in metabolism of acetoin at stationary phase have been previously studied, but only with the DNA microarray technology that they were found to be the highest induced region at T1 stage under this growth conditions. There were quite a few clusters of genes, which were uncharacterized, that showed higher levels of mRNA three hours into the stationary phase. They included ykfABCD, yjmCDEFG, and yodLPORST. In contrast, DNA regions such as alsT and yxeKLMN showed a reduction in mRNA levels upon entering stationary phase. This data is summaried in Table 3. Table 3 describes a selection of genes or gene clusters that showed an induction or reduction (in paranthesis) in mRNA transcriptional levels at stationary phase of *Bacillus subtilis* when grown in Schaeffer's medium supplemented with 0.1% glucose in the presence of oxygen.

TABLE 3

| Gene | Description | T0/log* | T1/log* | T3/log* |
|---|---|---|---|---|
| csn | | 4.2 | 21.3 | 10.6 |
| vaW | unknown | 4–11 | 19–38 | 3–21 |
| yncM | unknown | 6.61 | 28.65 | 8.71 |
| yvyD | | 8.09 | 6.73 | 10.57 |
| sunA | | 18.08 | 35.65 | |
| yolIJK | | 7–13 | 12–27 | |
| ydjL | | 14.9 | 11.4 | |
| yqhIJ | | 15–36 | 16–38 | 2–4 |
| ycgMN | | 150–300 | 15–18 | 4–6 |
| yhfRSTUV | | 8–12 | | |
| acoABCL | | | 155–358 | 19–46 |
| glvAC | | | 43–134 | |
| yfkABCD | | | | 14–26 |
| yngEFGHI | | | | 13–24 |
| yjmCDEFG | | | | 14–23 |
| yodLPORST | | | | 15–26 |
| alsT | | (15) | (29) | (41) |
| yxeKLMN | | (9–12) | (40–64) | (40–80) |

*Units in fold induction vs control

What is claimed is:

1. A method for the expression of a coding region of interest in a Bacillus sp comprising:

a) providing a transformed Bacillus sp cell having a chimeric gene comprising a nucleic acid fragment comprising the promoter region of a Bacillus gene operably linked to a coding region of interest expressible in a Bacillus sp, wherein the nucleic acid fragment comprising the promoter region of a Bacillus gene is narGHJI; and b) growing the transformed Bacillus sp cell of step (a) in the absence of oxygen wherein the chimeric gene of step (a) is expressed.

2. A method for the expression of a coding region of interest in a Bacillus sp comprising:

a) providing a transformed Bacillus sp cell having a chimeric gene comprising a nucleic acid fragment comprising the promoter region of a Bacillus gene operably linked to a coding region of interest expressible in a Bacillus sp, wherein the nucleic acid fragment comprising the promoter region of a Bacillus gene is narGHJI,;

b) growing the transformed Bacillus sp. cell of step (a) in the presence of oxygen whereby the cell density is increased; and c) removing oxygen from the transformed Bacillus sp. cell or step (b) whereby the chimeric gene is expressed.

3. A method according to claim 2 wherein after step (c) oxygen is re-supplied to the transformed Bacillus sp. cell.

4. A method according to either of claims 1 or 2 wherein the nucleic acid fragment comprising the promoter region of a Bacillus gene is selected from the group consisting of SEQ ID NOs: 1–4.

5. A method according to any of claims 1, 2 or 3 wherein the expression of the chimeric gene is down-regulated at the stationary phase.

6. A method according to any one of claims 1, 2, or 3, wherein the Bacillus sp. cell is selected from the species consisting of *Bacillus subtillus, Bacillus thuringiensis, Bacillus anthracis, Bacillus cereus, Bacillus brevis, Bacillus megaterium, Bacillus intermedius, Bacillus thermoamyloliquefaciens, Bacillus amyloliquefaciens, Bacillus circulans, Bacillus licheniformis, Bacillus macerans, Bacillus sphaericus, Bacillus stearothermophilus, Bacillus laterosporus, Bacillus acidocaldarius, Bacillus pumilus,* and *Bacillus pseudofirmus.*

7. A method according to any one of claims 1, 2, or 3, wherein the coding region of interest is selected from the group consisting of crtE crtB, pds, crtD, crtL, crtZ, crtX crtO, phaC, phaE, efe, pdc, adh, genes encoding limonene synthase, pinene synthase, bornyl synthase, phellandrene synthase, cineole synthase, sabinene synthase, and taxadiene synthase.

* * * * *